(12) United States Patent
Aslanian et al.

(10) Patent No.: US 7,846,946 B2
(45) Date of Patent: Dec. 7, 2010

(54) HETEROATOM-LINKED SUBSTITUTED PIPERIDINES AND DERIVATIVES THEREOF USEFUL AS HISTAMINE $H_3$ ANTAGONISTS

(75) Inventors: Robert G. Aslanian, Rockaway, NJ (US); Michael Y. Berlin, Flemington, NJ (US); Christopher W. Boyce, Flemington, NJ (US); Jianhua Chao, Pompton Lakes, NJ (US); Manuel de Lera Ruiz, Branchburg, NJ (US); Pietro Mangiaracina, Monsey, NY (US); Kevin D. McCormick, Basking Ridge, NJ (US); Mwangi W. Mutahi, Nyeri (KE); Stuart B. Rosenblum, West Orange, NJ (US); Neng-Yang Shih, Warren, NJ (US); Daniel M. Solomon, Edison, NJ (US); Wing C. Tom, Cedar Grove, NJ (US); Henry A. Vaccaro, South Plainfield, NJ (US); Junying Zheng, Bridgewater, NJ (US); Xiaohong Zhu, Edison, NJ (US)

(73) Assignee: Schering Plough Corporation, Kenilworth, NJ (US)

( * ) Notice: Subject to any disclaimer, the term of this patent is extended or adjusted under 35 U.S.C. 154(b) by 0 days.

(21) Appl. No.: 12/507,563

(22) Filed: Jul. 22, 2009

(65) Prior Publication Data

US 2009/0286830 A1 Nov. 19, 2009

Related U.S. Application Data

(62) Division of application No. 11/455,625, filed on Jun. 19, 2006, now Pat. No. 7,635,705.

(60) Provisional application No. 60/692,110, filed on Jun. 20, 2005.

(51) Int. Cl.
*A61K 31/4545* (2006.01)
*C07D 401/14* (2006.01)

(52) U.S. Cl. ........................... 514/318; 546/187
(58) Field of Classification Search ................ 514/318; 546/187

See application file for complete search history.

(56) References Cited

U.S. PATENT DOCUMENTS

| | | | |
|---|---|---|---|
| 4,983,597 | A | 1/1991 | Yang et al. |
| 5,306,817 | A | 4/1994 | Thiruvengadam et al. |
| 5,561,227 | A | 10/1996 | Thiruvengadam et al. |
| 5,618,707 | A | 4/1997 | Homann et al. |
| 5,624,920 | A | 4/1997 | McKittrick et al. |
| 5,627,176 | A | 5/1997 | Kirkup et al. |
| 5,631,365 | A | 5/1997 | Rosenblum et al. |

(Continued)

FOREIGN PATENT DOCUMENTS

WO WO 98/06394 2/1998

(Continued)

OTHER PUBLICATIONS

Alzheimer's Treatment. Retrieved online Oct. 2, 2010, URL: http://www.nlm.nih.gov/medlineplus/attentiondeficithyperactivitydisorder.html.*
Attention deficit hyperactivity Disorder. Retrieved online Oct. 2, 2010, URL: http://www.nlm.nih.gov/medlineplus/attentiondeficithyperactivitydisorder.html.*

(Continued)

*Primary Examiner*—Kamal A Saeed
*Assistant Examiner*—Samantha L Shterengarts
(74) *Attorney, Agent, or Firm*—J. Eric Thies; Gerard M. Devlin

(57) ABSTRACT

Disclosed are novel compounds of the formula

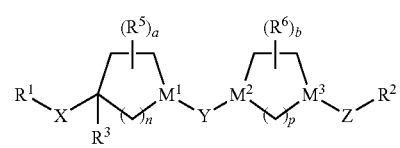

or a pharmaceutically acceptable salt thereof, wherein:
$M^1$ and $M^3$ are CH or N;
$M^2$ is CH, CF or N;
Y is —C(=O)—, —C(=S)—, —(CH$_2$)$_q$—, —C(=NOR$^7$)— or —SO$_{1-2}$—;
Z is a bond or optionally substituted alkylene or alkenylene;
$R^1$ is H, or alkyl, cycloalkyl, aryl, heteroaryl, heterocycloalkyl, all optionally substituted, or a group of the formula:

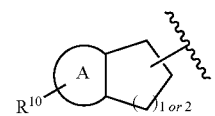

where ring A is a heteroaryl ring;
$R^2$ is optionally substituted alkyl, alkenyl, aryl, heteroaryl, cycloalkyl or heterocycloalkyl;
$R^3$ is H, —C(O)NH$_2$, or alkyl, aryl, cycloalkyl, heterocycloalkyl or heteroaryl, all optionally substituted;
and the remaining variables are as defined in the specification; compositions and methods of treating allergy-induced airway responses, congestion, obesity, metabolic syndrome, alcoholic fatty liver disease, hepatic steatosis, nonalcoholic steatohepatitis, cirrhosis, hepatacellular carcinoma and cognition deficit disorders using said compounds, alone or in combination with other agents.

2 Claims, No Drawings

U.S. PATENT DOCUMENTS

| | | | |
|---|---|---|---|
| 5,633,246 | A | 5/1997 | McKittrick et al. |
| 5,656,624 | A | 8/1997 | Vaccaro et al. |
| 5,661,145 | A | 8/1997 | Davis |
| 5,688,785 | A | 11/1997 | Vaccaro |
| 5,688,787 | A | 11/1997 | Burnett et al. |
| 5,688,990 | A | 11/1997 | Shankar |
| 5,698,548 | A | 12/1997 | Dugar et al. |
| 5,728,827 | A | 3/1998 | Thiruvengadam et al. |
| 5,739,321 | A | 4/1998 | Wu et al. |
| 5,744,467 | A | 4/1998 | McKittrick et al. |
| 5,756,470 | A | 5/1998 | Yumibe et al. |
| 5,767,115 | A | 6/1998 | Rosenblum et al. |
| 5,846,966 | A | 12/1998 | Rosenblum et al. |
| 5,856,473 | A | 1/1999 | Shankar |
| 5,869,479 | A | 2/1999 | Kreutner et al. |
| 5,886,171 | A | 3/1999 | Wu et al. |
| 5,919,672 | A | 7/1999 | Homann et al. |
| 6,093,812 | A | 7/2000 | Thiruvengadam et al. |
| 6,096,883 | A | 8/2000 | Wu et al. |
| 6,133,001 | A | 10/2000 | Homann et al. |
| 6,207,822 | B1 | 3/2001 | Thiruvengadam et al. |
| RE37,721 | E | 5/2002 | Rosenblum et al. |
| 6,627,757 | B2 | 9/2003 | Fu et al. |
| 6,632,933 | B2 | 10/2003 | Altmann et al. |
| 6,720,328 | B2 | 4/2004 | Aslanian et al. |
| 6,720,378 | B2 | 4/2004 | Maruyama et al. |
| 6,849,621 | B2 | 2/2005 | Rosenblum et al. |
| 2002/0039774 | A1 | 4/2002 | Kramer et al. |
| 2002/0128252 | A1 | 9/2002 | Glombik et al. |
| 2002/0128253 | A1 | 9/2002 | Glombik et al. |
| 2002/0137689 | A1 | 9/2002 | Glombik et al. |
| 2003/0105028 | A1 | 6/2003 | Ghosal et al. |
| 2004/0019099 | A1 | 1/2004 | Aslanian et al. |
| 2004/0048843 | A1 | 3/2004 | Ting et al. |
| 2004/0097483 | A1 | 5/2004 | Zeng et al. |
| 2004/0180860 | A1 | 9/2004 | Burnett et al. |
| 2004/0180861 | A1 | 9/2004 | Burnett et al. |
| 2004/0198700 | A1 | 10/2004 | Burnett et al. |
| 2004/0198743 | A1 | 10/2004 | Hey et al. |
| 2004/0224953 | A1 | 11/2004 | Cowart et al. |

FOREIGN PATENT DOCUMENTS

| | | |
|---|---|---|
| WO | WO 99/65867 | 12/1999 |
| WO | WO 01/58891 A2 | 8/2001 |
| WO | WO 02/32893 | 4/2002 |
| WO | WO 02/066464 | 8/2002 |
| WO | WO 02/072570 A2 | 9/2002 |
| WO | WO 03/088967 | 10/2003 |
| WO | WO 03/103669 | 12/2003 |
| WO | WO 04/000831 A1 | 12/2003 |
| WO | WO 2004/005247 | 1/2004 |
| WO | WO 2004/014947 | 2/2004 |
| WO | WO 2004/087655 | 10/2004 |
| WO | WO 2004/089373 | 10/2004 |
| WO | WO 2004/101546 | 11/2004 |
| WO | WO 2004/000803 | 12/2004 |
| WO | WO 2004/000804 | 12/2004 |
| WO | WO 2004/000805 | 12/2004 |
| WO | WO 2005/000353 | 1/2005 |
| WO | WO 2005/002897 | 1/2005 |
| WO | WO 2005/009955 | 2/2005 |
| WO | WO 2005/021495 | 3/2005 |
| WO | WO 2005/021497 | 3/2005 |
| WO | WO 2005/023305 | 3/2005 |
| WO | WO 2005/030225 | 4/2005 |
| WO | WO 2005/033100 | 4/2005 |
| WO | WO 2005/042692 | 5/2005 |
| WO | WO 2005/044256 | 5/2005 |
| WO | WO 2005/046662 | 5/2005 |
| WO | WO 2005/047248 | 5/2005 |
| WO | WO 2005/061451 | 7/2005 |
| WO | WO 2005/061452 | 7/2005 |
| WO | WO 2005/062824 | 7/2005 |

OTHER PUBLICATIONS

Anderson et al., *The Practice of Medicinal Chemistry*, Academic Press, New York, 739-754,(1996).

Berge et al., *Journal of Pharmaceutical Sciences*, 66(1) 1-19 (1977).

Bingham et al., Over one hundred solvates of sulfathiazole, *Chem, Commun.*, 603-604 (2001).

Caira et al., Preparation and Crystal Characterization of a Polymorph, a Monohydrate, and an Ethyl Acetate Solvate of the Antifungal Fluconazole, *J. Pharmaceutical Sci.*, 93(3), 601-611 (2004).

Gould, Salt selection for basic drugs, *International J. of Pharmaceutics* 33 201-217 (1986).

Greene et al., Protective Groups in organic Synthesis, Wiley, New York (1991).

Grundy et al., Definition of Metabolic Syndrome, *Circulation*, 109:433-438 (2004).

Leurs et al., The Histamine $H_3$ Receptor: From Gene Cloning to $H_3$ Receptor Drugs, *Nature Reviews, Drug Discovery*, 4:107(2005).

McLeod et al., Pharmacological Characterization of the Novel Histamine $H_3$-Receptor Antagonists *N*-(3,5-Dichlorophenyl)-*N*'-[[4-(1H-imidazol-4-ylmethyl)phenyl]-methyl]-urea (SCH 79687), *The Journal of Pharmacology and Experimental Therapeutics*, 305:3, 1037-1044 (2003).

Ram et al., Potential hypolipidemic agents: Part V—Synthesis and biological activity of new ethyl 4-(2-oxoazetidin-4-yl)phenoxyalkanoates, *Indian J. Chem.*, 29:B, 1134-1137 (1990).

Rizzo et al., Pharmacological characterization of histamine $H_3$ receptors in isolated guinea pig pulmonary artery and ileum, *Eur. J. Pharmacol.*, vol. 294, 329-335 (1995).

Roche, Bioreversible Carriers in Drug Design, American Pharmaceutical Association and Pergamon Press, (1987).

Stahl, et al, *Handbook of Pharmaceutical Salts. Properties, Selection and Use*, (2002).

van Tonder et al., Preparation and Physicochemical Characterization of 5 Niclosamide Solvates and 1 Hemisolvate, *AAPS PharmSciTech.*, 5(1), article 12 (2004).

Witkin, Selective histamine $H_3$ receptor antagonists for treatment of cognitive deficiencies and other disorders of the central nervous system, *Pharmacology and Therapeutics*, 103, 1-20 (2004).

Written Opinion of the International Search Authority—6 Pages.

* cited by examiner

HETEROATOM-LINKED SUBSTITUTED PIPERIDINES AND DERIVATIVES THEREOF USEFUL AS HISTAMINE H₃ ANTAGONISTS

RELATED APPLICATIONS

This application is a divisional application of application U.S. Ser. No. 11/455,625, filed on Jun. 19, 2006 and now allowed, which in turn claims priority to provisional application 60/692,110, filed Jun. 20, 2005, herein incorporated by reference.

FIELD OF THE INVENTION

The present invention relates to heteroatom-linked substituted piperidines and derivatives thereof useful as histamine H₃ antagonists. The invention also relates to pharmaceutical compositions comprising said compounds and their use in treating inflammatory diseases, allergic conditions, obesity, metabolic syndrome, cognition deficit disorders, cardiovascular and central nervous system disorders. The invention also relates to the use of a combination of histamine H₃ antagonists of this invention with histamine H₁ compounds for the treatment of inflammatory diseases and allergic conditions, as well to the use of a combination of an histamine H₃ antagonist of this invention with other actives useful for treating obesity, metabolic syndrome or cognition deficit disorders. Pharmaceutical compositions comprising a combination of one or more novel histamine H₃ antagonist compounds of the invention with one or more histamine H₁ compounds or one or more compounds useful for treating obesity, metabolic syndrome or cognition deficit disorders are also contemplated.

BACKGROUND OF THE INVENTION

The histamine receptors, $H_1$, $H_2$, $H_3$ and $H_4$ have been characterized by their pharmacological behavior. The $H_1$ receptors are those that mediate the response antagonized by conventional antihistamines. $H_1$ receptors are present, for example, in the ileum, the skin, and the bronchial smooth muscle of humans and other mammals. The most prominent $H_2$ receptor-mediated responses are the secretion of gastric acid in mammals and the chronotropic effect in isolated mammalian atria. $H_4$ receptors are expressed primarily on eosinophils and mast cells and have been shown to be involved in the chemotaxis of both cell types.

In the periphery, $H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation. In addition, in rodents, peripheral $H_3$ receptors are expressed in brown adipose tissue, suggesting that they may be involved in thermogenesis regulation.

$H_3$ receptors are also present in the CNS. $H_3$ receptor expression is observed in cerebral cortex, hippocampal formation, hypothalamus and other parts of the human and animal brain. $H_3$ receptors are expressed on histaminergic neurons and, as heteroreceptors, on neurons involved in other neurotransmitter systems, where $H_3$ receptor activation results in presynaptic inhibition of neurotransmitter release. In the particular case of histaminergic neurons, $H_3$ receptors have been implicated in the regulation of histamine hypothalamic tone, which in turn has been associated with the modulation of sleeping, feeding and cognitive processes in the human brain (see, for example, Leurs et al., *Nature Reviews, Drug Discovery*, 4, (2005), 107).

It is also known and has been described in the literature that histamine is involved in regulation of cognitive and memory processes in the human brain (see, for example, *Life Sciences*, 72, (2002), 409-414). Consequently, indirect modulation of histaminergic brain function through the central $H_3$ receptors may be a means to modulate these processes. Different classes of $H_3$ receptor ligands have been described and their use for neurological and psychiatric diseases has been suggested (see, e.g., US 20040224953, WO2004089373, WO2004101546). $H_3$ receptor antagonists may be useful in treating various neuropsychiatric conditions, where cognitive deficits are an integral part of the disease, specifically ADHD, schizophrenia and Alzheimer's disease (see, for example, Hancock, A.; Fox, G. in *Drug Therapy* (ed. Buccafusco, J. J.). (Birkhauser, Basel, 2003).

Imidazole $H_3$ receptor antagonists are well known in the art. More recently, non-imidazole $H_3$ receptor antagonists have been disclosed in U.S. Pat. Nos. 6,720,328 and 6,849,621 and in and 2004/0019099. WO 2003/103669 and WO 2003/088967 (US Published Applications 2004/0097483 and 2004/0048843) disclose 1-(4-piperidinyl)-benzimidazolone and 1-(4-piperidinyl)benzimidazole derivatives. All these patents or publications are incorporated by reference.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides novel compounds of formula I:

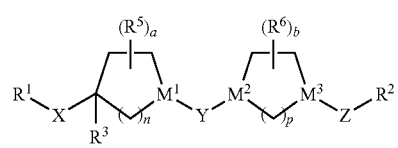

or a pharmaceutically acceptable salt thereof, wherein:
a is 0, 1 or 2;
b is 0, 1 or 2;
n is 1, 2 or 3;
p is 1, 2 or 3;
$M^1$ is CH or N;
$M^2$ is CH, CF or N;
$M^3$ is CH or N
with the proviso that when $M^2$ and $M^3$ are each N, p is 2 or 3;
Y is —C(=O), —C(=S)—, —(CH₂)$_q$—, —C(=NOR⁷)— or —SO$_{1\text{-}2}$—;
q is 1, 2, 3, 4 or 5, provided that when $M^1$ and $M^2$ are both N, q is 2, 3, 4 or 5;
X is —N(R⁴)—, —N(R⁴)—CH(R¹⁹)—, —CH(R¹⁹)N(R⁴)—, —(CH₂), —C(O)—N(R⁴)—, —O—(CH₂)₂—C(O)N(R⁴)—, —CH₂—O—(CH₂)₃—C(O)—N(R⁴)—, —CH(R¹⁹)CH(R¹⁹)N(R⁴)—, —(CH₂)$_r$—N(R⁴)—C(O)—, —C(O)—N(R⁴)—CH₂—, —(CH₂)$_r$—N(R¹⁹)C(O)N(R¹⁹)—, —N(R¹⁹)C(O)N(R¹⁹)—(CH₂)$_r$—, —(CH₂)$_r$—OC(O)N(R¹⁹)—, —N(R¹⁹)C(O)O—, —O—, —OCH₂—, —CH₂O—, —OC(O)—, —C(O)O—, OCH(R¹⁹)—, —CH(R¹⁹)O—, —S—, —S(O)— or —SO₂—;

r is 0, 1, 2 or 3;

t is 0 or 1;

Z is a bond, —[C(R$^8$)(R$^{8'}$)]$_n$—, —CH(R$^{20}$)—CH(R$^{20}$)—O—, —CH(R$^{20}$)—CH(R$^{20}$)—N—, —CH(R$^{20}$)—[C(R$^{23}$)(R$^{23'}$)]$_{1-5}$—, —CH(R$^{20}$)—C(R$^{20}$)=C(R$^{20}$)—, —CH(R$^{20}$)—C(R$^{20}$)=C(R$^{20}$)—[C(R$^{23}$)(R$^{23'}$)]$_{1-3}$— or —[C(R$^8$)(R$^{8'}$)]$_n$—, wherein at least one C(R$^8$)(R$^{8'}$) is interrupted by a cycloalkylene or heterocycloalkylene group, provided that when M$^3$ is N and Z is —[C(R$^8$)(R$^{8'}$)]$_n$— interrupted by a heterocycloalkylene group bonded through a ring nitrogen, the alkylene portion of the Z group has 2-4 carbon atoms between M$^3$ and said nitrogen;

n' is an integer from 1 to 6;

R$^1$ is H, R$^{10}$-alkyl, R$^{10}$-cycloalkyl, R$^{10}$-aryl, R$^{10}$-monoheteroaryl, R$^{10}$-heterocycloalkyl or a group of the formula:

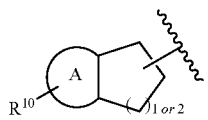

where ring A is a monoheteroaryl ring, said monoheteroaryl or monoheteroaryl ring is a monocyclic ring having 1 to 4 heteroatoms selected from O, S, and N, said heteroatoms interrupting an aromatic carbocyclic ring structure having from 1 to 6 carbon atoms, provided that there are no adjacent oxygen and/or sulfur atoms present with monoheteroaryl rings, such as isothiazole, isoxazole, oxazole, triazole, tetrazole, thiazole, thiophene, furane, pyrrole, pyrazole, pyrane, pyrimidine, pyrazine, furaranyl, pyridazine, and pyridine (including pyridine N-oxide) being preferred;

R$^2$ is R$^{16}$-alkyl, R$^{16}$-alkenyl, R$^{16}$-aryl, R$^{16}$-heteroaryl, R$^{16}$-cycloalkyl or R$^{16}$-heterocycloalkyl;

R$^3$ is H, alkyl, R$^{21}$-aryl, R$^{22}$-cycloalkyl, R$^{22}$-heterocycloalkyl, R$^{21}$-heteroaryl or —C(O)NH$_2$;

R$^4$ is H, alkyl, haloalkyl, R$^{18}$-aryl, R$^{18}$-heteroaryl, R$^{18}$-arylalkyl, —C(O)R$^{12}$ or —SO$_2$R$^{13}$;

R$^5$ and R$^6$ are each independently selected from the group consisting of halo, alkyl, —OH, alkoxy, haloalkyl, preferably —CF$_3$ and —CN; or two R$^5$ substituents on the same carbon atom or two R$^6$ substituents on the same carbon atom form =O;

R$^7$ is H, alkyl, haloalkyl, R$^{10}$-aryl or R$^{10}$-heteroaryl;

R$^8$ and R$^{8'}$ independently are 1, 2 or 3 substituents independently selected from the group consisting of H, R$^{10}$-cycloalkyl, R$^{10}$-heterocycloalkyl, R$^{10}$-aryl, R$^{10}$-heteroaryl and haloalkyl, preferably —CF$_3$;

each R$^9$ is independently selected from the group consisting of H and alkyl;

R$^{10}$ is 1, 2, 3 or 4 substituents independently selected from the group consisting of H, halo, alkyl, R$^{10'}$-cycloalkyl, —OH, alkoxy, R$^{10'}$-aryl, R$^{10'}$-arylalkyl, R$^{10'}$-heteroaryl, R$^{10'}$-heteroarylalkyl, R$^{10'}$-aryloxy, haloalkyl, haloalkoxy, —NO$_2$, —C(O)-alkyl, —C(O)heterocycloalkyl, —CO$_2$R$^{11}$, —N(R$^{11}$)$_2$, —CON(R$^{11}$)$_2$, —NHC(O)R$^{11}$, —NHC(O)-alkoxyalkyl-, —NHC(O)—CH$_2$—NHC(O)CH$_3$, —NHSO$_2$R$^{11}$, —CH(=NOR$^{19}$), —SO$_2$N(R$^{11}$)$_2$, —SO$_2$CF$_3$ and —CN;

each R$^{10'}$ is 1, 2, 3 or 4 substituents independently selected from the group consisting of H, halo, alkyl, cycloalkyl, —OH, alkoxy, aryl, arylalkyl, heteroaryl, heteroarylalkyl, aryloxy, haloalkyl, haloalkoxy, —NO$_2$, —C(O)-alkyl, —C(O)-heterocycloalkyl, —CO$_2$R$^{11}$, —N(R$^{11}$)$_2$, —CON(R$^{11}$)$_2$, —NHC(O)R$^{11}$, —NHC(O)-alkoxyalkyl-, —NHC(O)CH$_2$—NHC(O)CH$_3$, —NHSO$_2$R$^{11}$, —CH(=NOR$^{19}$), —SO$_2$N(R$^{11}$)$_2$, —SO$_2$CF$_3$ and —CN;

each R$^{11}$ is independently selected from the group consisting of H, alkyl, haloalkyl, R$^{18}$-aryl, R$^{18}$-heteroaryl, R$^{18}$-arylalkyl, R$^{18}$-cycloalkyl and R$^{18}$-heterocycloalkyl;

R$^{12}$ is alkyl, R$^{18}$-cycloalkyl, R$^{18}$-aryl, R$^{18}$-heteroaryl or R$^{18}$-heterocycloalkyl;

R$^{13}$ is alkyl, aryl or alkylsulfonylalkyl;

R$^{16}$ is 1, 2 or 3 substituents independently selected from the group consisting of H, halo, alkyl, R$^{10}$-cycloalkyl, —OH, alkoxy, hydroxyalkyl, R$^{10}$-aryl, R$^{10}$-heteroaryl, R$^{10}$-heterocycloalkyl, R$^{10}$-aryloxy, haloalkyl, preferably —CF$_3$, haloalkoxy, preferably —OCF$_3$, —NO$_2$, —CO$_2$R$^{17}$, —N(R$^{17}$)$_2$, -alkylene-N(R$^{17}$)$_2$, —CON(R$^{17}$)$_2$, —NHC(O)R$^{17}$, —NHC(O)OR$^{17}$, —NHSO$_2$R$^{17}$, —SO$_2$N(R$^{17}$)$_2$ and —CN;

each R$^{17}$ is independently selected from the group consisting of H, alkyl, haloalkyl, aryl, heteroaryl, cycloalkyl and heterocycloalkyl;

R$^{18}$ is 1, 2 or 3 substituents independently selected from the group consisting of H, alkyl, halo, alkoxy, haloalkyl, preferably —CF$_3$, —NO$_2$, —CN and -alkylene-N(R$^{17'}$)$_2$;

each R$^{17'}$ is independently selected from the group consisting of H, alkyl, haloalkyl, aryl, heteroaryl, cycloalkyl and heterocycloalkyl R$^{19}$ is independently selected from the group consisting of H and alkyl;

R$^{20}$ is independently selected from the group consisting of H and alkyl;

R$^{21}$ is 1, 2, 3 or 4 substituents independently selected from the group consisting of H, halo, alkyl, —OH, alkoxy, haloalkyl, preferably —CF$_3$, or —CHF$_2$, haloalkoxy, preferably —OCF$_3$, —NO$_2$, —CN, —C(O)N(R$^{19}$)$_2$ and —N(R$^{19}$)$_2$;

R$^{22}$ is 1, 2 or 3 substituents independently selected from the group consisting of halo, alkyl, —OH, alkoxy, haloalkyl, preferably —CF$_3$, —NO$_2$ and —CN; and R$^{23}$ is independently 1, 2 or 3 substituents independently selected from the group consisting of H, R$^{10}$-cycloalkyl, R$^{10}$-heterocycloalkyl, R$^{10}$-aryl, heteroaryl, haloalkyl, preferably —CF$_3$, halo, —CN, —OH, alkoxy, haloalkoxy, preferably —OCF$_3$, —NO$_2$, and —N(R$^9$)$_2$.

R$^{23'}$ is independently 1, 2 or 3 substituents independently selected from the group consisting of H, R$^{10}$-cycloalkyl, R$^{10}$-heterocycloalkyl, R$^{10}$-aryl, heteroaryl, haloalkyl, preferably —CF$_3$, —OH, alkoxy, haloalkoxy, preferably —OCF$_3$, —NO$_2$, and —N(R$^9$)$_2$.

This invention also provides a pharmaceutical composition comprising an effective amount of at least one compound of formula I and a pharmaceutically acceptable carrier.

This invention further provides a method of treating: allergy, allergy-induced airway (e.g., upper airway) responses (e.g., pruritis, sneezing, rhinorrhea, mucosal inflammation; see, for example, McLeod, JPET, 305 (2003) 1037), congestion (e.g., nasal congestion), hypotension, cardiovascular disease, diseases of the GI tract, hyper- and hypo-motility and acidic secretion of the gastro-intestinal tract, metabolic syndrome, obesity, sleeping disorders (e.g., hypersomnia, somnolence, and narcolepsy), hypo- and hyperactivity of the central nervous system (for example, agitation and depression), cognition deficit disorders (such as attention deficit hyperactivity disorder (ADHD), Alzheimer's Disease (AD) and schizophrenia) nonalcoholic fatty liver disease (NAFLD), hepatic steatosis, nonalcoholic steatohepatitis (NASH), cirrhosis, hepatocellular carcinoma and/or other CNS disorders (such as migraine) comprising administering to a patient in need of such treatment an effective amount of at least one compound of formula I.

"Patient" means a mammal, typically a human, although veterinary use is also contemplated.

In particular, compounds of this invention are useful for treating congestion, metabolic syndrome, obesity and cognition deficit disorders.

This invention further provides a pharmaceutical composition comprising an effective amount of a combination of at least one compound of formula I and at least one $H_1$ receptor antagonist in combination with a pharmaceutically acceptable carrier.

This invention further provides a method of treating allergy, allergy-induced airway responses, and/or congestion comprising administering to a patient in need of such treatment an effective amount of a combination of at least one compound of formula I and at least one $H_1$ receptor antagonist.

This invention further provides a pharmaceutical composition comprising an effective amount of a combination of at least one compound of formula I and at least one other compound useful in treating obesity, metabolic syndrome, cognition deficit disorders, NAFLD, hepatic steatosis, NASH, cirrhosis, or hepatacellular carcinoma in combination with a pharmaceutically acceptable carrier.

This invention further provides a method of treating obesity, metabolic syndrome or cognition deficit disorders comprising administering to a patient in need of such treatment an effective amount of a combination of at least one compound of formula I and at least one other compound useful in treating obesity, metabolic syndrome, cognition deficit disorders, NAFLD, hepatic steatosis, NASH, cirrhosis, or hepatacellular carcinoma.

Kits comprising a compound of formula I in a pharmaceutical composition, and a separate $H_1$ receptor antagonist in a pharmaceutical composition in a single package are also contemplated, as are kits comprising a compound of formula I in a pharmaceutical composition, and at least one separate compound useful in treating obesity, metabolic syndrome, cognition deficit disorders, NAFLD, hepatic steatosis, NASH, cirrhosis or hepatacellular carcinoma in a pharmaceutical composition in a single package.

DETAILED DESCRIPTION OF THE INVENTION

Preferred definitions of the variables in the structure of formula I are as follows:

$R^1$ is preferably $R^{10}$-aryl or $R^{10}$-heteroaryl. More preferably, $R^1$ is $R^{10}$-phenyl or $R^{10}$-heteroaryl wherein heteroaryl is a 6-membered ring, especially $R^{10}$-pyridyl. $R^{10}$ is preferably 1, 2 or 3 substituents independently selected from H, alkyl, halo, —$CF_3$, —$CHF_2$ and —CN. Other preferred groups for $R^1$ include:

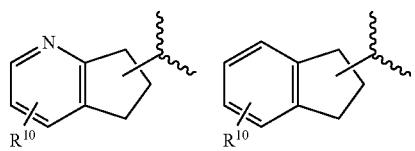

where ⸾ is the rest of the compound of formula I and the aryl or heteroaryl ring is attached through X.

$M^1$ is preferably N. $M^2$ is preferably CH or CF, more preferably CF. $M^3$ is preferably N.

Variables n and p are preferably each 2.
Variables a and b are preferably each independently 0 or 1, more preferably 0.

Y is preferably —C(=O)—.

Z is preferably $C_1$-$C_3$ alkylene, —CH($R^{20}$)—($R^{23}$—$C_1$-$C_5$ alkylene)-, —CH($R^{20}$)—C($R^{20}$)=C($R^{20}$)—, —(CH$_2$)$_2$—O— or $C_1$-$C_3$ alkylene interrupted by a cycloalkylene group, wherein $R^{20}$ is preferably H and $R^{23}$ is halo. More preferably, Z is one of the following: —CH$_2$—, —(CH$_2$)$_3$—, —CH$_2$—CH=CH—, —(CH$_2$)$_2$—CH(F)—, —CH$_2$—CH(F)—CH$_2$—, —(CH$_2$)$_2$—O— or

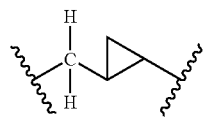

$R^2$ is preferably $R^{16}$-heteroaryl or $R^{16}$-heterocycloalkyl, more preferably a 5 or 6 membered $R^{16}$-heteroaryl or a 4, 5 or 6-membered $R^{16}$-heterocycloalkyl. More preferred $R^2$ groups are $R^{16}$-pyridyl, $R^{16}$-pyrimidyl, $R^{16}$-pyradazinyl, $R^{16}$-tetrahydropyranyl, $R^{16}$-azetidinyl, $R^{16}$-oxazolyl and $R^{16}$-thiazolyl. When $R^2$ is $R^{16}$-pyridyl, $R^{16}$-pyrimidyl, $R^{16}$-pyradazinyl, $R^{16}$-oxazolyl or $R^{16}$-thiazolyl, $R^{16}$ preferably 1 or 2 substituents independently selected from H, —CH$_3$, —NH$_2$ and —NHCH$_3$. When $R^2$ is $R^{16}$-tetrahydropyranyl or $R^{16}$-azetidinyl, $R^{16}$ is preferably 1 or 2 substituents independently selected from H and —CH$_3$. Especially preferred are 2-amino pyridyl, 2-amino oxazolyl, 2-amino thiazolyl, 1-methyl-azetidinyl and tetrahydropyranyl, with 2-amino pyridyl being most preferred.

$R^3$ is preferably H, $R^{22}$-aryl, wherein $R^{22}$ is H, or —C(O)NH$_2$, most preferably H.

X is preferably —NR$^4$—, —NR$^4$CH$_2$—, —O—, —OCH$_2$—, —NR$^4$C(O)—, —C(O)NR$^4$—, —S— or —SO$^2$—, more preferably —O—, —NR$^4$— or —S—. $R^4$ is preferably H, alkyl or —C(O)R$^{12}$, more preferably H or alkyl. $R^{12}$ is preferably alkyl or aryl, more preferably alkyl or phenyl.

$R^5$ and $R^6$ are independently preferably selected from H, alkyl, OH or fluoro.

Preferred compounds among those exemplified below are examples 11, 15, 24, 26N, 30, 31, 33, 34, 35, 36, 80, 81, 88, 195, 202, 219, 220, 225, 227, 230, 237, 256, 257, 259, 260, 265, 274, 280, 290, 294, 295, 298, 299, 300, 301, 308, 309 and 310.

More preferred compounds of this invention are selected from examples 15, 26N, 33, 34, 35, 36, 80, 81, 219, 237, 257, 265, 274, 298, 299, 300 and 301.

As used herein, the following terms have the following meanings, unless indicated otherwise:

the left side of all divalent radicals is attached to the left portion of formula I and the right side of all divalent radicals is attached the right side of the formula based upon where the variable is in formula I; e.g; when X is —CH$_2$—O—(CH$_2$)$_3$—C(O)—N(R$^4$)—, R$^1$ is attached to the left or "—CH$_2$—O" side of the variable and the right or "N(R$^4$)—" side is attached to the left hand ring along with the $R^3$ substituent.

alkyl (including, for example, the alkyl portions of arylalkyl and alkoxy) represents straight and branched carbon chains and contains from one to six carbon atoms;

alkylene represents a divalent straight or branched alkyl chain, e.g., ethylene (—CH$_2$—) or propylene (—CH$_2$CH$_2$CH$_2$—);

haloalkyl or haloalkoxy represent alkyl or alkoxy chains as defined above wherein one or more hydrogen atoms are replaced by halogen atoms, e.g., —CF$_3$, CF$_3$CH$_2$CH$_2$—, CF$_3$CF$_2$— or CF$_3$O—;

aryl (including the aryl portion of arylalkyl) represents a monocyclic or multicyclic carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment;

arylalkyl represents an aryl group, as defined above, bound to an alkyl group, as defined above, wherein said alkyl group is the point of attachment;

cycloalkyl represents a non-aromatic mono- or multicyclic ring system comprising about 3 to about 10 carbon atoms, preferably about 5 to about 10 carbon atoms. Preferred cycloalkyl rings contain about 3 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

halogen (halo) represents fluoro, chloro, bromo and iodo;

heteroaryl represents cyclic groups having 1 to 4 heteroatoms selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms. The rings do not contain adjacent oxygen and/or sulfur atoms. Examples include but are not limited to isothiazolyl, isoxazolyl, oxazolyl, furazanyl, triazolyl, tetrazolyl, thiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoquinolinyl, quinolinyl, naphthyridinyl; all available substitutable carbon and nitrogen atoms can be substituted as defined.

heterocycloalkyl represents a saturated carbocylic ring containing from 3 to 15 carbon atoms, preferably from 4 to 6 carbon atoms, which carbocyclic ring is interrupted by 1 to 3 hetero atoms selected from —O—, —S—, —SO—, —SO$_2$ or —NR$^{40}$— wherein R$^{40}$ represents H, C$_1$ to C$_6$ alkyl, arylalkyl, —C(O)R$^{20}$, —C(O)OR$^{20}$, or —C(O)N(R$^{20}$)$_2$ (wherein each R$^{20}$ is independently selected from the group consisting of H, alkyl, phenyl and benzyl); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

Also, as used herein, "upper airway" usually means the upper respiratory system—i.e., the nose, throat, and associated structures.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

A line drawn into a ring means that the indicated bond may be attached to any of the substitutable ring carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When the term "—NR$^4$—" appears, it means that the R$^4$ substituent is attached to a nitrogen atom in a chain, i.e.,

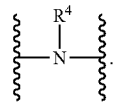

Claim 1 does not include compounds known by the skilled artisan to be unstable.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g. a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of formula I contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)-ethyl, 1-methyl-1-(($C_1-C_6$)alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O) $(OH)_2$, —P(O)(O$(C_1-C_6)$alkyl)$_2$ or glycosyl (the radical resulting from the removal of a hydroxyl group of the hemiacetal form of a carbohydrate), and the like.

If a compound of formula I incorporates an amine functional group, a prodrug can be formed by the replacement of a hydrogen atom in the amine group with a group such as, for example, R"-carbonyl, R"O-carbonyl, NR"R'"-carbonyl where R" and R'" are each independently $(C_1-C_{10})$alkyl, $(C_3-C_7)$cycloalkyl, benzyl, or R"-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy$(C_1-C_6)$alkyl, amino $(C_1-C_4)$alkyl or mono-N- or di-N,N-$(C_1-C_6)$alkylaminoalkyl, C(Y$^4$)Y$^5$ wherein Y$^4$ is H or methyl and Y$^5$ is mono-N- or di-N,N-$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

The compounds of this invention can be combined with an $H_1$ receptor antagonist (i.e., the compounds of this invention can be combined with an $H_1$ receptor antagonist in a pharmaceutical composition, or the compounds of this invention can be administered with an $H_1$ receptor antagonist).

Numerous chemical substances are known to have histamine $H_1$ receptor antagonist activity and can therefore be used in the methods of this invention. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole. More preferably, said H, antagonist is selected from loratadine, descarboethoxyloratadine, fexofenadine or cetirizine.

Preferably, in the above combinations of $H_3$ and $H_1$ antagonists, nasal congestion is treated.

The term "metabolic syndrome" refers to a combination of risk factors for cardiovascular disease (CVD) identified in the National Cholesterol Education Program's Adult Treatment Panel III report. See for example the discussion by Grundy et al in *Circulation*, 109 (2004), 433-438. The components of metabolic syndrome are: 1) abdominal obesity; 2) atherogenic dyslipidemia; 3) raised blood pressure; 4) insulin resistance; 5) proinflammatory state; and 6) prothrombotic state.

Weight loss drugs include appetite suppressants, metabolic rate enhancers and nutrient absorption inhibitors. Appetite suppressant agents useful for treating obesity or metabolic syndrome include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3-[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagons-like peptide 1 (GLP-1) agonists; topiramate; and phytopharm compound 57. Metabolic rate enhancers include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxyl steroid dehydrogenase type 1 (11β HSD-1) inhibitors; melanocortin-3 receptor (Mc3r) agonists; and stearoyl-CoA desaturase-1 (SCD-1) compounds. Nutrient absorption inhibitors include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Specific compounds for use in the combination for treating obesity and metabolic syndrome include rimonabant, 2-methyl-6-(phenylethynyl)-pyridine, 3-[(2-methyl-1,4-thiazol-4-yl)ethynyl]pyridine, Melanotan-II, dexfenfluramine, fluoxetine, paroxetine, fluoxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

Preferred compounds for use in the combination for treating obesity and metabolic syndrome include rimonabant, dexfenfluramine, fenfluramine, phentermine, leptin, nalmefene, axokine, sibutramine, topiramate, phytopharm compound 57, oleoyl-estrone and orlistat.

Also preferred are combinations of one or more compounds of formula I and one or more HMG-CoA reductase inhibitors and/or one or more cholesterol absorption inhibitors, such as one or more substituted azetidinone or substituted β-lactam sterol absorption inhibitors, and/or other cholesterol related drugs that decrease LDL and increase HDL for treating metaolic syndrome nonalcoholic fatty liver disease (NAFLD), hepatic steatosis, nonalcoholic steatohepatitis (NASH), cirrhosis, hepatacellular carcinoma or obesity.

Typical HMG-CoA reductase inhibitors include statins such as lovastatin, simvastatin, pravastatin, atorvastatin, fluvastatin, resuvastatin, cerivastatin, rivastatin and pitavastatin.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

Non-limiting examples of suitable substituted azetidinones and methods of making the same include those disclosed in U.S. Pat. Nos. RE 37,721, 5,306,817, 5,561,227, 5,618,707, 5,624,920, 5,631,365, 5,656,624, 5,627,176, 5,633,246, 5,661,145, 5,688,785, 5,688,787, 5,688,990, 5,698,548, 5,728,827, 5,739,321, 5,744,467, 5,756,470, 5,767,115, 5,846,966, 5,856,473, 5,886,171, 5,919,672, 6,093,812, 6,096,883, 6,133,001, 6,207,822, 6,627,757, 6,632,933, U.S. Patent Publication Nos. 2003/0105028, 2004/0180860, 2004/0180861, and 2004/0198700, N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, and diphenyl azetidinones and derivatives disclosed in U.S. Patent Publication Nos. 2002/0039774, 2002/0128252, 2002/0128253 and 2002/0137689, and PCT Published Application Nos. WO 2002/066464, WO 04/000805, WO 04/005247, WO 04/000804, WO 04/000803, WO 04/014947, WO 04/087655, WO 05/009955, WO 05/023305, WO 05/021495, WO 05/021497, WO 05/044256, WO 05/042692, WO 05/033100, WO 05/030225, WO 05/047248, WO 05/046662, WO 05/061451, WO 05/061452, WO 05/062824, WO 05/02897, WO 05/000353, each of which is incorporated by reference herein.

An example of a suitable substituted azetidinone compound is represented by Formula (A) (ezetimibe) below:

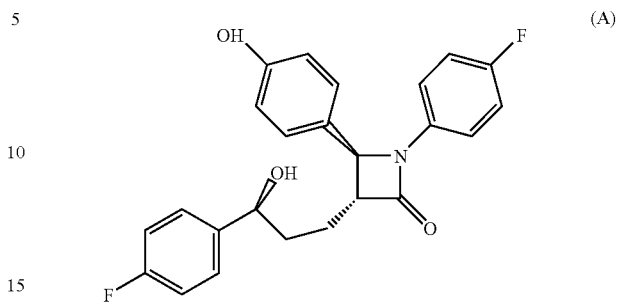

(A)

or pharmaceutically acceptable salts or solvates of the compound of Formula (A). The compound of Formula (A) can be in anhydrous or hydrated form. A product containing ezetimibe compound is commercially available as ZETIA® ezetimibe formulation from MSP Pharmaceuticals.

Typical compounds for use in combination with an $H_3$ antagonist of this invention for the treatment of cognition deficit disorders are atomoxetine and dexmethylphenidate for the treatment of ADHD, olanzapine, risperidone or aripiprazole for treatment of schizophrenia, and donepezil, heptylphysostigmine, tacrine, rivastigmine or galantamine for the treatment of Alzheimer's Disease.

In the methods of this invention wherein a combination of an $H_3$ antagonist of this invention is administered with an $H_1$ antagonist or another compound useful for treating obesity, metabolic syndrome or cognition deficit disorders, the $H_3$ antagonist and other compound can be administered simultaneously (at the same time, in a single dosage form or in separate dosage forms) or sequentially (first one and then the other over a period of time).

The preparation of compounds of Formula I can be realized in many ways known to those skilled in the art. Following are typical procedures for preparing various compounds; other procedures may also be applicable and the procedures may be modified to prepare other compounds within the scope of Formula I. One skilled in the art will recognize that one route will be optimal depending on the choice of appendage substituents. Additionally, one skilled in the art will recognize that in some cases the order of steps has to be controlled to avoid functional group incompatibilities.

The compounds of this invention can be prepared through one of the four general approaches outlined in Schemes 1 through 4. Scheme 1 shows a convergent synthesis in which AB and CD portions of the molecule are joined together: AB+CD=ABCD.

Scheme 1

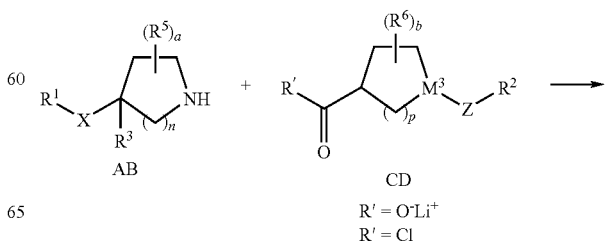

R' = O⁻Li⁺
R' = Cl

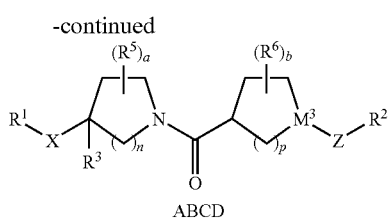

Alternatively, Scheme 2 shows a linear synthesis by assembling the ABC portion through the coupling of AB and C parts, and then adding on the D fragment: AB+C=ABC; ABC+D=ABCD.

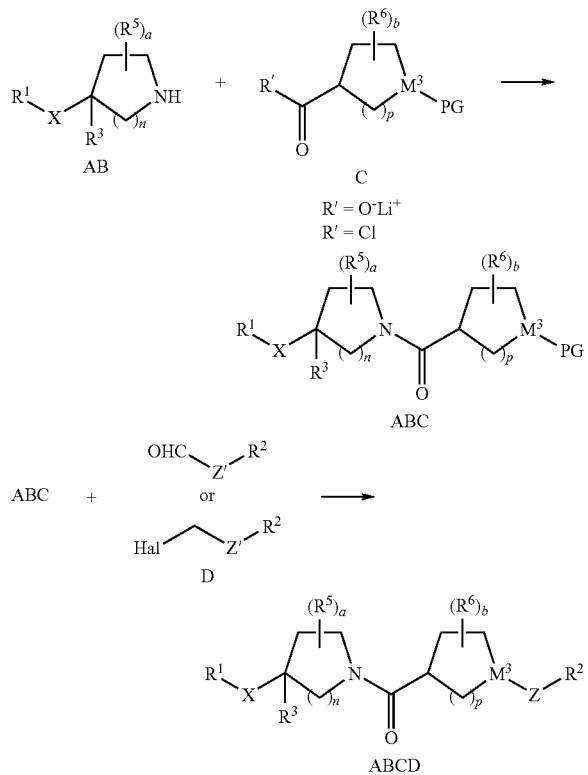

In particular, specific examples of these approaches wherein $M^1$-Y constitutes an amide fragment include amide coupling between a secondary amine, representative of the AB fragment, and carboxylic acid lithium salt, representative of the CD or C fragment, respectively. Alternatively, a carboxylic acid lithium salt is converted into the corresponding acid chloride and then coupled with the amine. In the scheme, PG is a protecting group. Conversion of the ABC intermediate into a compound of formula I is accomplished, for example, in the particular case when $M^3$ represents N, through deprotection of the secondary amine, followed by its reaction with an electrophilic D fragment, which most typically is an aldehyde (reductive amination) or a halide (alkylation) (Scheme 2), but also can be represented by an epoxide or other electrophile. Depending on the nature of groups in $R^1$, $R^2$ and $R^3$, the last step in either synthetic sequence involves cleavage of the protecting groups present in the molecule to yield final compounds.

In cases, where $M^1$-Y-$M^2$ constitutes a ketone (i.e., $M^1$ is CH, Y is —C(O)— and $M^2$ is CH), connection between B and C fragments may be established through the reaction of appropriate B ring-based carbon nucleophile (e.g., Grignard reagent or a transition metal-based reagent (Zn, Pd, Sn)), derived from the corresponding B-ring cycloalkyl halide, with a C ring-based Weinreb amide or aldehyde, generated from an acid (see Scheme 2), or any other suitable electrophile, such as, for example, a vinyl halide. Those skilled in the art will recognize that this approach may need to be followed by well-known synthetic procedures to finish elaboration of the ketone functionality, such as oxidation of an alcohol, or ozonolysis of an alkene.

Various examples of C and D fragments, as well as the methods employed in the synthesis of the CD portion, C and D parts separately, and the addition of C and then D fragments onto the initial AB fragment have been previously described in detail (e.g., U.S. Pat. No. 6,720,378 and US 2004/0097483). In the most simple case, D-electrophiles are a one-carbon aldehyde or alkyl halide attached to an $R^2$ group (Z' is a bond). Longer-chain D-electrophiles are synthesized through chain extension of one-carbon starting D-aldehydes (previously described or commercially available) by various methods known to those skilled in the art. Those methods include, but are not limited to, the reactions of starting aldehydes with alkylmetal reagents, carbon-phosphorus reagents (known as Wittig reactions and Horner-Emmons reactions), and reactions with other carbon nucleophiles, followed by appropriate functional elaboration, to obtain compounds where Z' is an appropriately substituted $C_1$ to $C_5$ alkyl or alkenyl group. Alternatively, in the particular case when $R^2$ is an aryl or heteroaryl, the corresponding D fragment with the elongated Z' is prepared by coupling an aryl halide with an appropriate alkyl or alkenyl metal (e.g., Li or MgHal) reagent, optionally in the presence of an appropriate transition metal catalyst (e.g, Cu, Ni). Some specific examples of these preparations are included below.

Assembly of the AB portion of the molecule is achieved through one of the two major approaches. In the first approach, the A fragment contains a nucleophilic functional group, which is reacted with an electrophilic functional group that is part of the B fragment. Examples of this approach include, but are not limited to those illustrated in Scheme 3; in particular, reactions comprise reductive amination of an aldehyde or a ketone, nucleophilic aliphatic substitution or an amide coupling or an esterification.

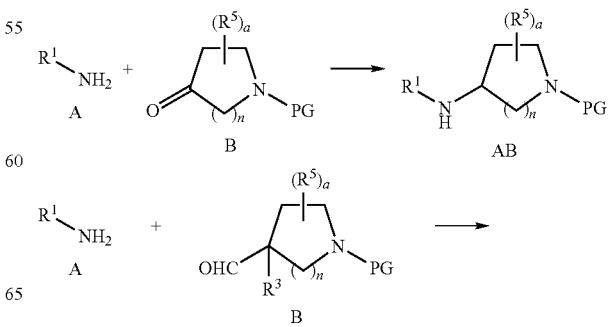

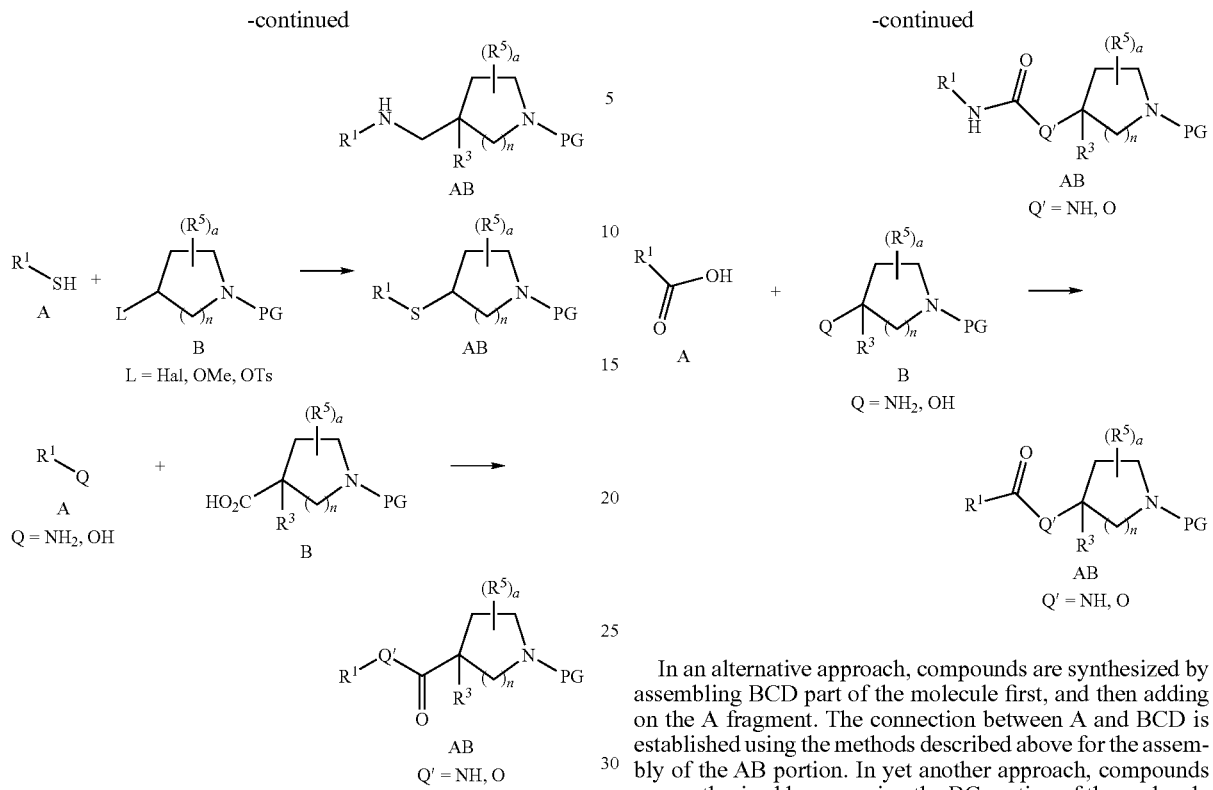

In a complementary approach, fragment A contains an electrophilic functionality, which reacts with a nucleophilic functional group on fragment B. Examples of this approach include, but are not limited to those illustrated in Scheme 4, in particular nucleophilic aromatic substitution or transition metal-mediated (e.g., Pd) coupling with a nitrogen or oxygen nucleophile (in the particular case when $R^1$ is a heteroaryl), nucleophilic addition to an N=C bond (e.g., isocyanate), reaction with a sulfonyl halide, an amide coupling or an esterification.

Scheme 4

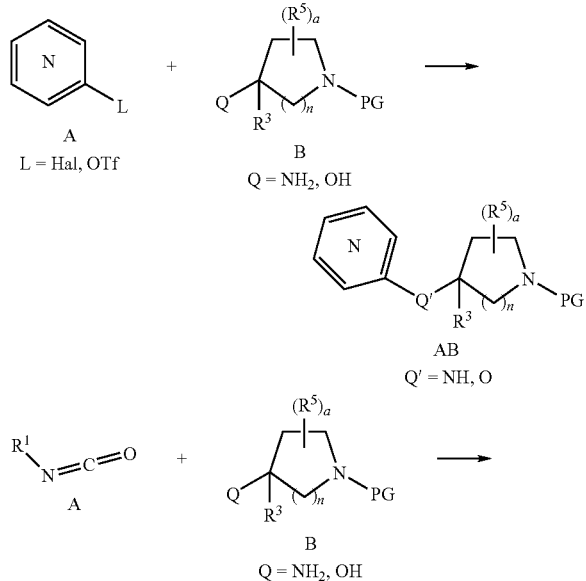

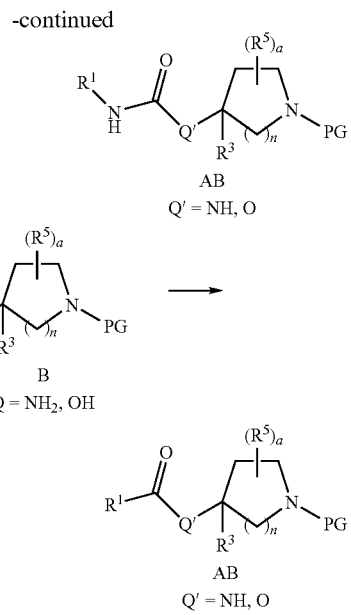

In an alternative approach, compounds are synthesized by assembling BCD part of the molecule first, and then adding on the A fragment. The connection between A and BCD is established using the methods described above for the assembly of the AB portion. In yet another approach, compounds are synthesized by preparing the BC portion of the molecule first, then adding on the A or D fragment, then following the approaches described above. One skilled in the art will recognize that most fragments will contain more than one functional group and that selective protection-deprotection may be an integral part of the above mentioned transformations. Examples of actual procedures employed in the syntheses of the corresponding compounds are described below.

The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formula I can be prepared by the general methods outlined above. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

Unless otherwise stated, the following abbreviations have the stated meanings in the Examples below:

Me=methyl; Et=ethyl; Bu=butyl; Pr=propyl; Ph=phenyl; t-BOC=tert-butoxycarbonyl; Ac=acetyl; DCC=dicyclohexylcarbodiimide; DCE=dichloroethane; DCM=dichloro-methane; DEAD=diethyl azodicarboxylate; DIPEA=N,N-diisopropylethylamine (Hunig's base); DMAP=4-dimethylaminopyridine; DMF=dimethylformamide; EDCI=1-(3-dimethylaminopropyl)-3-ethylcarbodiimide; FMOC=N-(9-fluorenylmethoxycarbonyl); HOBT=1-hydroxybenzotriazole; NaBH(OAc)$_3$= sodium triacetyboro-hydride; RT=room temperature; TFA=trifluoroacetic acid; THF=tetrahydrofuran; TEMPO=2, 2,6,6-tetramethyl-1-piperidinyloxy, free radical; TLC=thin layer chromatography; TMSI=1-(trimethylsilyl)imidazole; HRMS=High Resolution Mass Spectrometry; LRMS=Low Resolution Mass Spectrometry; nM=nanomolar;

Ki=Dissociation Constant for substrate/receptor complex; pA2=−logEC$_{50}$, as defined by J. Hey, *Eur. J. Pharmacol.*, (1995), Vol. 294, 329-335; Ci/mmol=Curie/mmol (a measure of specific activity)

Example 1

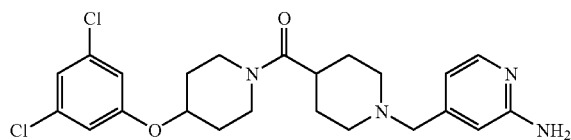

Step 1:

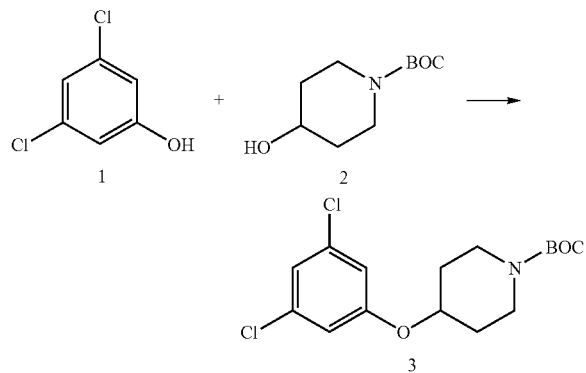

To a solution of 3,5-dichlorophenol 1 (1.54 g, 9.46 mmol), 1-Boc-4-hydroxypiperidine 2 (2.00 g, 9.94 mmol), and triphenylphosphine (3.30 g, 12.43 mmol) in anhydrous THF (75 ml) was added DEAD (1.96 ml, 12.43 mmol) dropwise at 0° C. The reaction mixture was then warmed up to RT and stirred for 36 h. The solvent was removed by reduced pressure. Et$_2$O was added to the resulting residue and white solid came out of the ether solution. The mixture was filtered, and the filtrate was concentrated in vacuo. The crude residue was purified by flash chromatography (silica gel, elution with 12.5% EtOAc in hexanes) to give 2.10 g (64%) of the desired product 3 as a white solid.

Step 2:

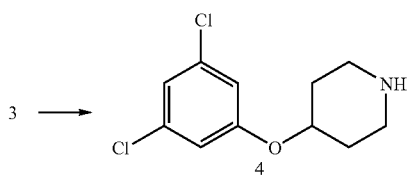

To a solution of 3 (2.10 g, 6.07 mmol) in 1,4-dioxane (15 ml) was added HCl (4.0 M in 1,4-dioxane, 15.0 ml, 60.0 mmol) at RT. The reaction mixture was heated at 50° C. for 10 min., and then stirred at RT for 12 h. The solvent was removed by reduced pressure, followed by addition of CH$_2$Cl$_2$ and 1.0 M aqueous NaOH solution. The organic layer was separated, dried over MgSO$_4$, and concentrated in vacuo. 1.06 g of crude residue 4 (71%) was obtained as a colorless oil and used in the next reaction without further purification.

Step 3:

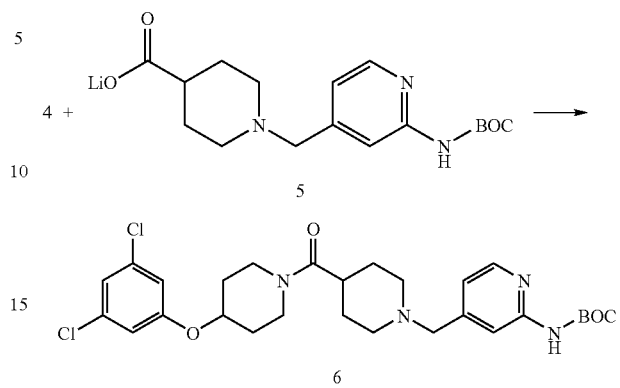

Compound 5 was prepared as described in WO 2002/032893 (herein incorporated by reference), steps 1-5 or Example 1.

To a solution of piperidine 4 (300 mg, 1.22 mmol) and lithium salt 5 (416 mg, 1.22 mmol) in a solution of DMF (4.0 ml) and CH$_2$Cl$_2$ (4.0 ml) was added DIPEA (0.42 ml, 1.53 mmol) and HOBT (207 mg, 1.53 mmol). The reaction mixture was stirred at RT for 5 min. followed by addition of EDCI (292 mg, 1.53 mmol). The reaction mixture was then heated at 80° C. for 9 h. CH$_2$Cl$_2$ and 1.0 M aqueous NaHCO$_3$ solution were added. The organic layer was washed with H$_2$O twice, dried over MgSO$_4$, filtered, and concentrated in vacuo. The crude residue was purified by flash chromatography (silica gel, elution with 50% EtOAc in hexanes and 5% MeOH in CH$_2$Cl$_2$) to give 385 mg (58%) of the desired product 6 as a white solid.

Step 4:

To a solution of 6 (370 mg, 0.68 mmol) in CH$_2$Cl$_2$ was added TFA (3.7 ml, 48 mmol). The reaction mixture was stirred at RT for 12 h. The reaction solution was diluted with CH$_2$Cl$_2$ and then washed with 1.0 M aqueous NaOH solution. The organic layer was separated and concentrated in vacuo. The crude residue was purified by preparative thin-layer silica gel chromatography (10% MeOH in CH$_2$Cl$_2$) to give 205 mg (60%) of the title compound as a white solid, which was converted to mono-HCl salt. MS: (M+1) 463.

Example 2

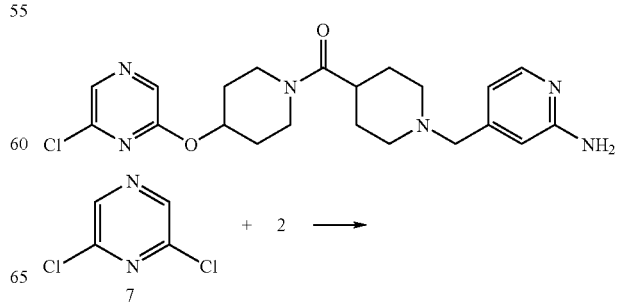

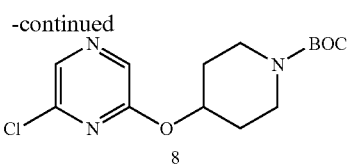

To a solution of 2 (900 mg, 4.47 mmol) in DMF (15 ml) was added NaH (108 mg, 4.47 mmol) at RT. The reaction mixture was stirred for 5 min, and 2,6-dichloropyrazine 7 (555 mg, 3.73 mmol) was added. The reaction mixture was then stirred at RT for 12 h. The reaction was diluted with EtOAc, and then washed with 10% aqueous $Na_2CO_3$ solution and brine. The organic layer was separated, dried over $MgSO_4$, and concentrated in vacuo. The crude residue was purified by flash chromatography (silica gel, elution with 20% EtOAc in hexanes) to give 1.1 g (79%) of the desired product 8 as a white solid.

Following procedures similar to those in Steps 2-4 of Example 1, the title compound was prepared. MS: (M+1) 431.

Example 3

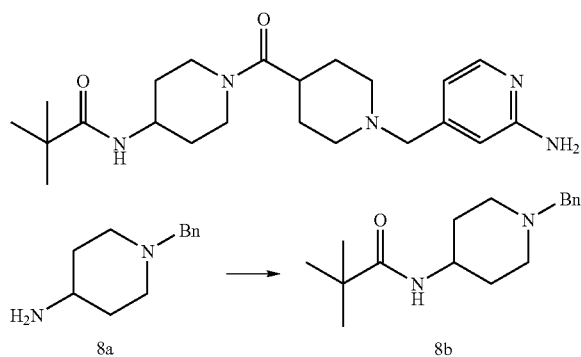

Step 1:

To a solution of amine 8a (10 g, 52.6 mmol) with $Et_3N$ (22 ml, 15.8 mmol) in $CH_2Cl_2$ (175 ml) at 5° C. was added pivaloyl chloride (6.3 g, 52.6 mmol). The reaction mixture was stirred at RT for 2 h, then filtered. The filtrate was washed with 1N aqueous NaOH solution and water, dried over $MgSO_4$, filtered, and concentrated in vacuo to give 15 g of the desired product 8b (100%) as a white solid.

Step 2:

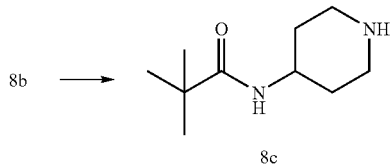

To a solution of 8b (14 g, 51 mmol) in MeOH (120 ml) in a 500 ml Parr flask was added palladium hydroxide (20 weight % Pd on carbon, wet). The reaction mixture was hydrogenated (50 psi) at RT for 4 days. The mixture was filtered, and the filtrate was concentrated to give 9.2 g (98%) of the desired product 8c as an off-white solid.

Steps 3-4: Compound 8c was converted into the title compound using the procedures described in Steps 3 and 4 of Example 1. MS: (M+1) 402.

Example 4

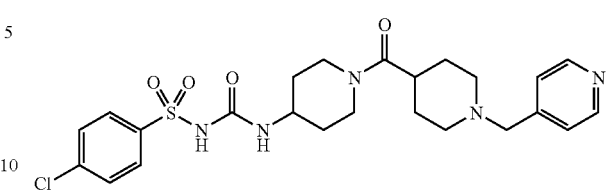

Step 1:

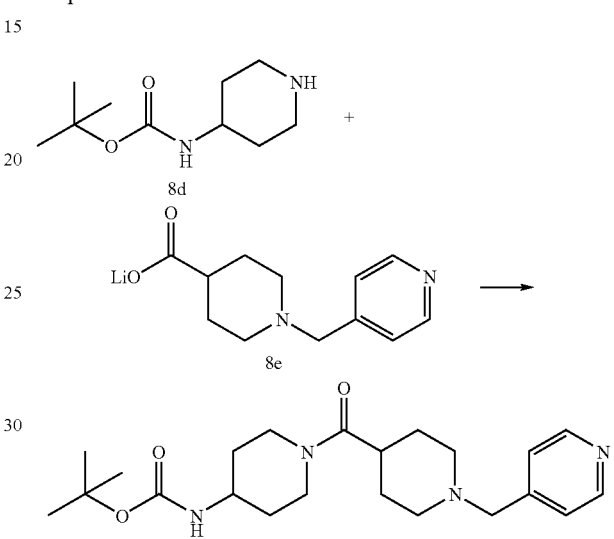

To a solution of Boc-(4-amino)-piperidine 8d (5.0 g, 21.1 mmol) and acid 8e (5.8 g, 26.4 mmol) (preparation described in U.S. Pat. No. 6,720,328) in DMF (70 ml) was added HATU (10.4 g, 27.4 mmol) and DMAP (5.67 g, 46.4 mmol). The reaction mixture was stirred at RT for 24 h. Water and EtOAc were then added. The organic layer was separated, washed with $H_2O$ and brine, dried over $MgSO_4$, filtered, and concentrated in vacuo. The crude residue was purified by flash chromatography (silica gel, elution with 5% MeOH in $CH_2Cl_2$) to give 2.6 g (31% yield) of the desired product 8f as a white solid.

Step 2:

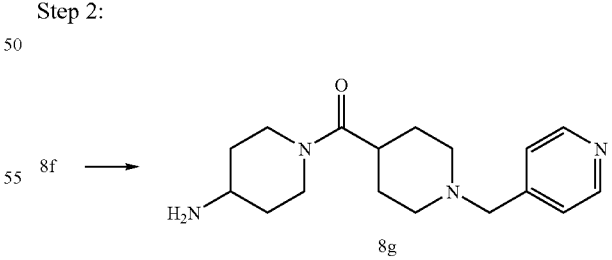

To a solution of 8f (1.5 g, 3.7 mmol) in $CH_2Cl_2$ (7.0 ml) was added TFA (2.9 ml, 37 mmol), and the reaction mixture was stirred at RT for 2 h. The reaction was diluted with $CH_2Cl_2$ and then washed with 1.0 M aqueous NaOH solution. The organic layer was separated and concentrated in vacuo. The crude residue was purified by flash chromatography (silica gel, 10% MeOH in $CH_2Cl_2$ with 2% $NH_4OH$) to give 0.8 g (73% yield) of the desired product 8 g as a white solid.

Step 3:

To a solution of amine 8 g (0.1 g, 0.33 mmol) in THF was added 4-chlorobenznesulfonyl isocynate (0.1 ml, 0.66 mmol). The reaction was stirred at RT overnight. A few drops of MeOH was added to quench the reaction, and the solvents were removed under reduced pressure. The crude residue was purified by flash chromatography (silica gel, 10% MeOH in CH$_2$Cl$_2$ with 2% NH$_4$OH) to give 0.085 g (50% yield) of the title compound as a white solid. MS: (M+1) 520.

Example 5

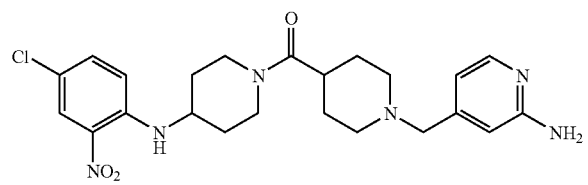

Step 1:

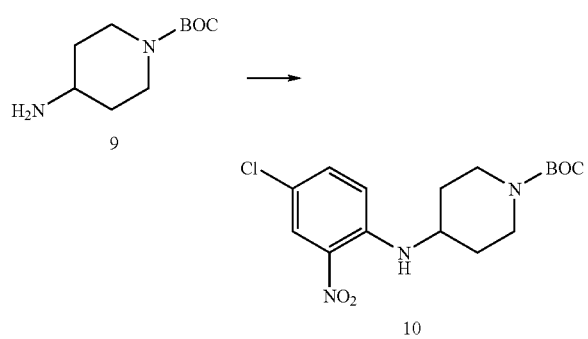

A mixture of 9 (10 g, 50 mmol), 2,5-dichloronitrobenzene (13 g, 70 mmol) and K$_2$CO$_3$ (9.7 g, 70 mmol) in dimethylacetamide (15 ml) was heated at 120° C. for 40 h. The mixture was concentrated to one-third volume, diluted with saturated aqueous NaHCO$_3$ and extracted with EtOAc. The organic layer was washed with saturated aqueous NaHCO$_3$, washed with brine, dried with Na$_2$SO$_4$ and concentrated. Recrystallation (EtOH) provided 10 as a bright yellow solid (13.8 g, 78%).

Step 2:

10 + 5 ⟶

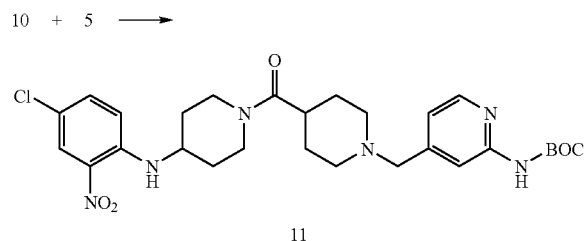

A solution of 10 (10 g, 28 mmol) in CH$_2$Cl$_2$ (70 ml) was treated with HCl (4M/dioxane, 70 ml). After stirring for 5 h at 20° C., the solvent was evaporated in vacuo. The resulting yellow residue was slurried in DMF (150 ml) and treated with 5 (11.8 g, 34 mmol), EDCI (13.5 g, 70 mmol), HOBT (1.5 g, 11 mmol), and DIPEA (20 ml, 115 mmol). After stirring for 2 days at 20° C., the reaction was concentrated to one-half volume, diluted with EtOAc, washed sequentially with saturated aqueous NaHCO$_3$ and brine, and concentrated. Recrystallation (EtOH) provided 11 as a bright yellow solid (10.8 g, 67%).

Step 3:

A solution of 11 (53 mg, 0.09 mmol) in CH$_2$Cl$_2$ (2 ml) was treated with TFA (2 ml), stirred for 2 h at 20° C. and concentrated. Chromatography (2-8% 7N NH$_3$-MeOH/CH$_2$Cl$_2$) provided the title compound as a bright yellow solid (37 mg, 84%). MS: (M+1) 473.

Example 6

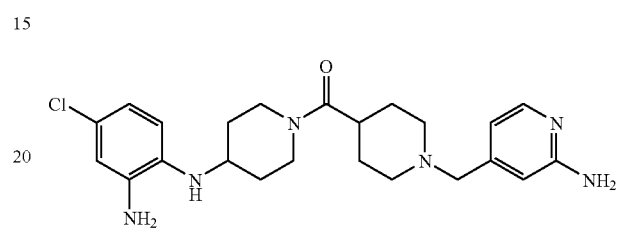

Step 1:

11 ⟶

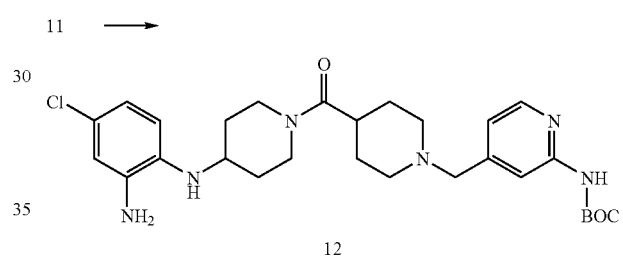

A solution of 11 (5.1 g, 8.7 mmol) in EtOH (22 ml) and THF (44 ml) was treated with Raney Nickel (~2 g) and hydrogenated at 35 psi H$_2$ overnight. The mixture was filtered through celite and concentrated. Chromatography (3-5% 7N NH$_3$-MeOH/CH$_2$Cl$_2$) provided 12 as a peach solid (4.5 g, 95%).

Step 2: Compound 12 was converted into the title compound using a procedure similar to that in Step 3 of Example 5. MS: (M+1) 443.

Examples 7 and 7A

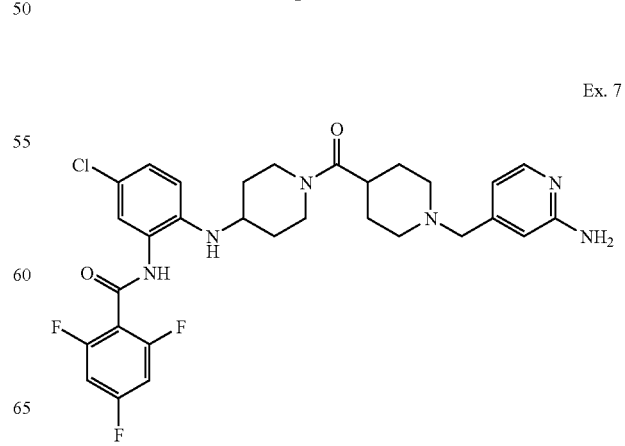

Ex. 7

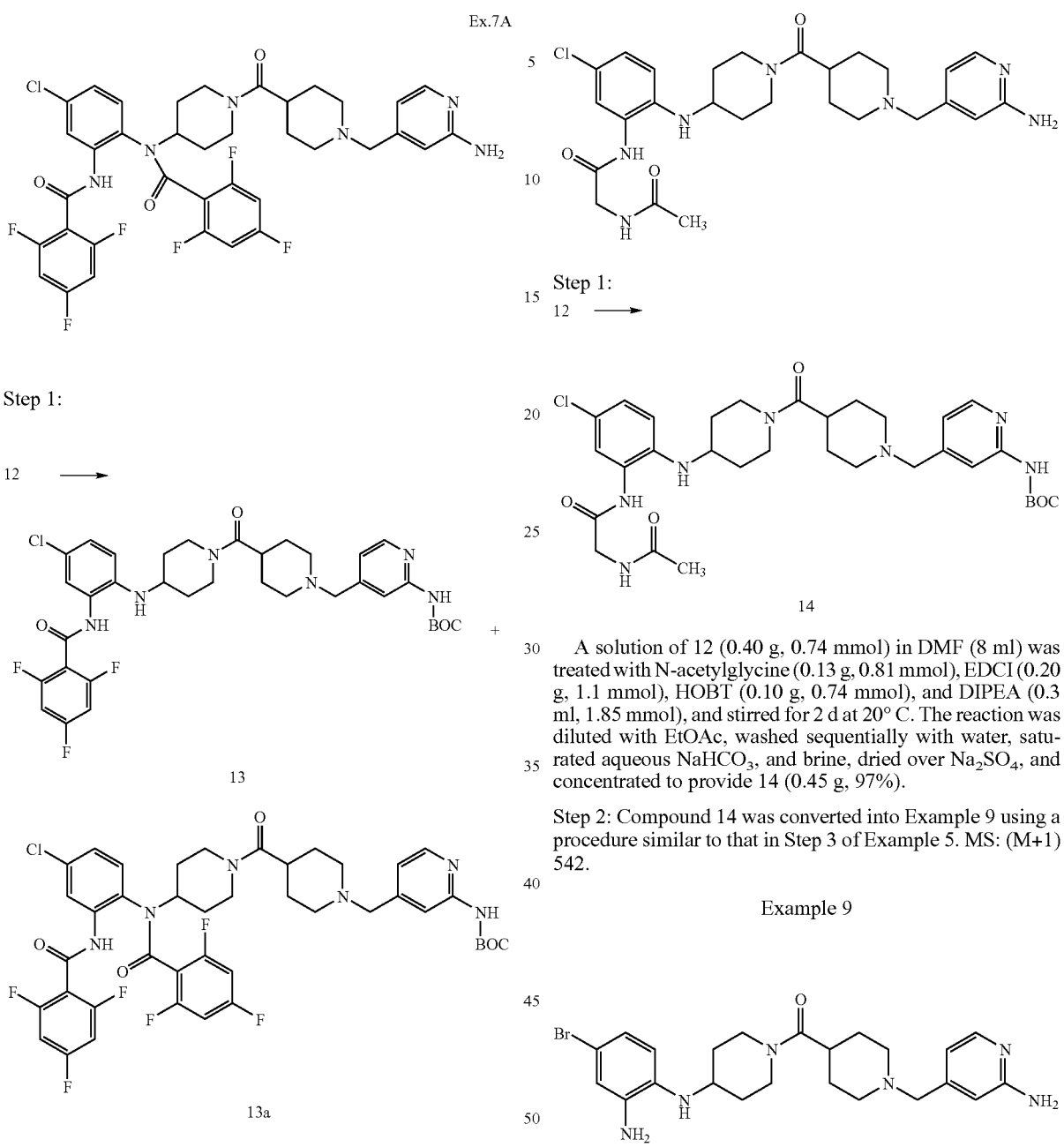

Example 8

Step 1:

12 →

A solution of 12 (0.40 g, 0.74 mmol) in DMF (8 ml) was treated with N-acetylglycine (0.13 g, 0.81 mmol), EDCI (0.20 g, 1.1 mmol), HOBT (0.10 g, 0.74 mmol), and DIPEA (0.3 ml, 1.85 mmol), and stirred for 2 d at 20° C. The reaction was diluted with EtOAc, washed sequentially with water, saturated aqueous NaHCO$_3$, and brine, dried over Na$_2$SO$_4$, and concentrated to provide 14 (0.45 g, 97%).

Step 2: Compound 14 was converted into Example 9 using a procedure similar to that in Step 3 of Example 5. MS: (M+1) 542.

Example 9

Steps 1-2:

9 →

A solution of 12 (0.40 g, 0.74 mmol) in CH$_2$Cl$_2$ (8 ml) was treated with 1,3,5-trifluorobenzoyl chloride (0.17 g, 0.89 mmol) and Et$_3$N (0.15 ml, 1.11 mmol) and stirred overnight at 20° C. The reaction mixture was poured into saturated aqueous NaHCO$_3$, extracted with CH$_2$Cl$_2$, washed with brine and concentrated. Chromatography (3% 7 N NH$_3$-MeOH/CH$_2$Cl$_2$) provided 13 (0.27 g, 51%) as a peach foam and 13a (0.10 g, 16%) as a tan film.

Step 2: Compound 13 was converted into Example 7 and compound 13a into Example 7A using a procedure similar to that in Step 3 of Example 5. Ex. 7: MS: (M+1) 601; Ex. 7A: MS: (M+1) 759.

Compound 15 was prepared using the procedures of Steps 1-2 of Example 5, substituting 5-bromo-2-fluoronitrobenzene for 2,5-dichloronitrobenzene in Step 1.

Step 3: A suspension of 15 (6.2 g, 10 mmol) in EtOH (20 ml) was treated with SnCl$_2$ (9.5 g, 50 mmol), heated to reflux for 3 h, and then stirred overnight at 20° C. The reaction mixture was poured on saturated aqueous NaHCO$_3$, extracted with CH$_2$Cl$_2$, dried over Na$_2$SO$_4$, and concentrated. Chromatography (5% 1 N NH$_3$-MeOH/EtOAc) provided the title compound (5.2 g, 52%) as a yellow solid. MS: (M+1) 487.

Example 10

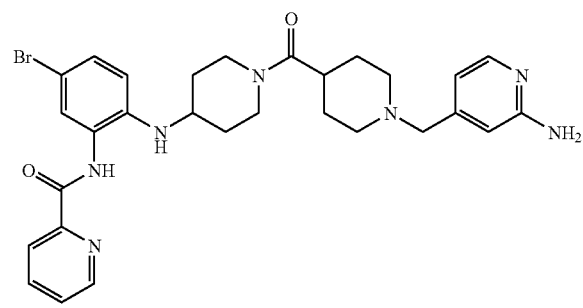

Example 9 was converted into the title compound as described in Example 8, Step 1. MS: (M+1) 594.

Example 11

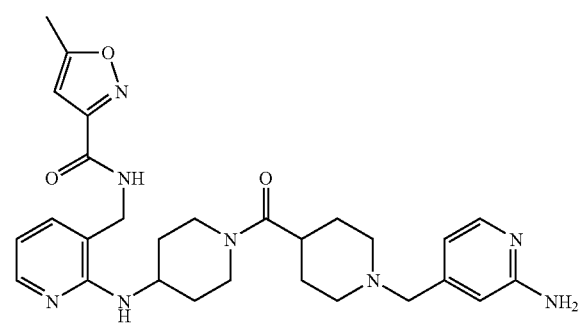

Step 1:

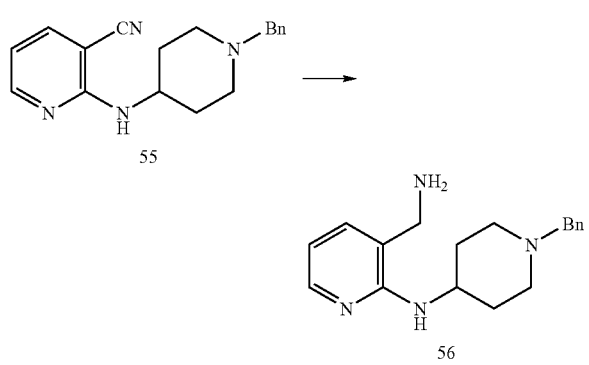

To a stirred suspension of LiAlH$_4$ (3.8 g; 0.10 mmol) in anhydrous ether (600 ml) was added portionwise compound 55 (10 g; 0.034 mmol) over 5 min. The resultant mixture was refluxed gently for 24 h. After cooling to RT, the stirred reaction mixture was treated successively and dropwise with water (4 ml), 20% aqueous NaOH (4 ml), followed by water (4 ml). The resultant mixture was stirred at RT for 2 h, then filtered. The filter cake was washed thoroughly with boiling CH$_2$Cl$_2$ (3×100 ml). The filtrate was concentrated under vacuum. The solid residue was treated with charcoal and purified by flash column chromatography (CH$_2$Cl$_2$-7N methanolic ammonia; 95:5). The desired fraction was triturated with isopropyl ether and filtered to obtain compound 56 as a solid (4.07 g; 46%).

Step 2:

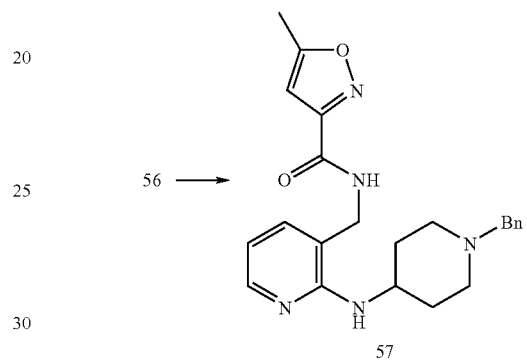

Compound 56 was converted into 57 as described for the conversion of compound 12 into 13 in Example 7.

Step 3:

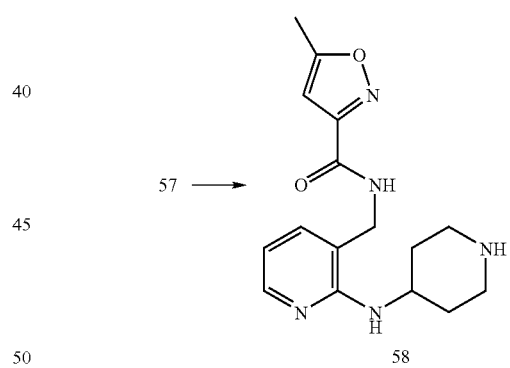

To a stirred solution of compound 57 (800 mg; 1.97 mmol) in dry CH$_2$Cl$_2$ (40 ml) maintained at 0° C. in an ice-water bath, was added dropwise 1-chloroethyl chloroformate (600 mg; 4.2 mmol). The cooling bath was removed and the reaction mixture was stirred at RT for 18 h before concentrating under vacuum. The residual viscous oil was dissolved in MeOH (60 ml) and refluxed for 1 h, then concentrated under vacuum. The residual solid was triturated with ether and filtration yielded the dihydrochloride salt form of compound 58 as solid (850 mg). This material was sufficiently pure for use in the next step.

Step 4: Compound 58 was converted into the title compound using procedures similar to those in Steps 3 and 4 of Example 1. MS: (M+1) 533.

Example 12

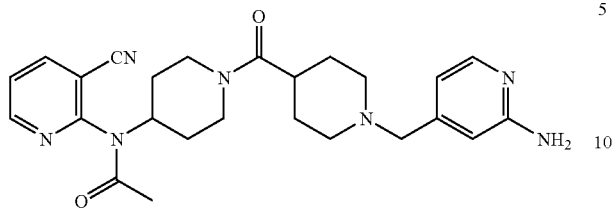

Step 1:

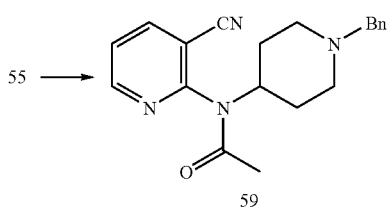

A mixture of compound 55 (5.84 g; 20 mmol) and acetic anhydride (80 ml) was refluxed for 18 h. The reaction mixture was allowed to cool and was then treated with ice-water and basified with concentrated NH₄OH. The resulting mixture, containing a gummy precipitate, was extracted with CH₂Cl₂. Combined extracts were dried over anhydrous MgSO₄, filtered, and the filtrate concentrated under reduced pressure. The residue was purified by flash column chromatography (EtOAc-MeOH; 97:3), to obtain compound 59 as a syrup (4.5 g, 67%).

Steps 2-3: Compound 59 was converted into the title compound using procedures similar to those described in Steps 3 and 4 of Example 11. MS: (M+1) 462.

Example 13

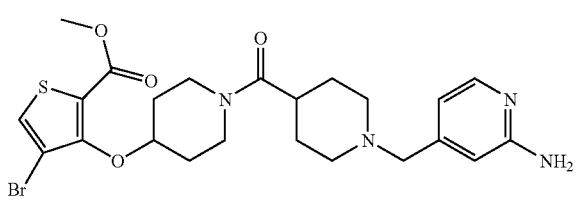

Step 1:

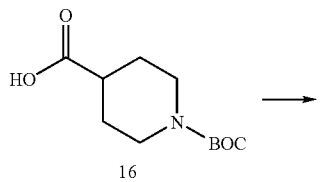

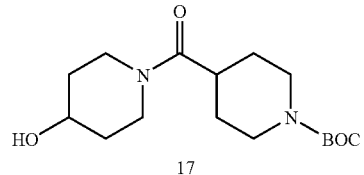

Oxalyl chloride (1.9 ml, 21.78 mmol) was added dropwise to a stirred solution of 1-Boc-isonipecotic acid 16 (4.5 g, 19.63 mmol) in CH₂Cl₂ (150 ml) at RT. A catalytic amount of DMF (40 μt) was added. The resulting mixture was stirred for 1 h 15 min. Et₃N (6.8 ml, 48.79 mmol) was added slowly to the mixture, followed by 4-hydroxypiperidine (2.68 g, 26.50 mmol). Reaction was continued for 2.5 d. The mixture was washed with H₂O (50 ml), a 1.0 M HCl aq. solution (50 ml), H₂O (50 ml), and brine (50 ml). The organic solution was dried with Na₂SO₄, filtered and concentrated in vacuo to give 4.62 g (75%) of the amide 17 as a near colorless solid.

Step 2:

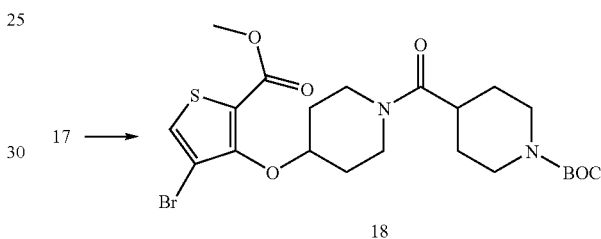

17 (1.0 g, 3.2 mmol) was dissolved in THF (10 ml). Triphenylphosphine (0.996 g, 3.80 mmol) and diisopropylazodicarboxylate (DIAD) (0.75 ml, 3.81 mmol) were added. The mixture was heated to reflux and continued overnight. The solvent was evaporated in vacuo, the dark brownish oily residue was dissolved in CH₂Cl₂ (50 ml), and filtered through a 1-in short silica gel pad, rinsing with CH₂Cl₂. The filtrate was discarded, further rinsed with CH₂Cl₂-MeOH (100:1, 50:1, v/v), and the filtrate was concentrated in vacuo to afford 1.56 g of the crude ether-linked product 18 as a light yellow oily solid.

Step 3:

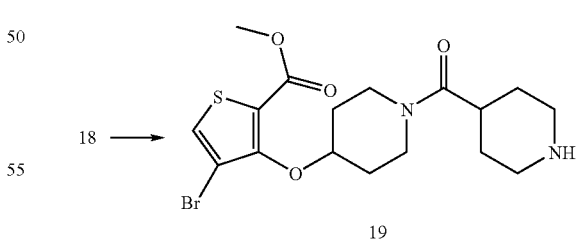

18 (1.56 g) was dissolved in CH₂Cl₂ (30 ml) and treated with TFA (5 ml). The mixture was stirred overnight and concentrated in vacuo to an oily residue. The residue was dissolved in CH₂Cl₂ (100 ml), washed with a sat. NaHCO₃ aqueous solution and brine. The organic solution was dried with Na₂SO₄ and concentrated in vacuo to oil. This crude product mixture was treated with a 1.0 M HCl aqueous solution, washed with CH₂Cl₂, basified to pH~12 using a 1.0 M NaOH aqueous solution, and extracted with CH$_2$Cl$_2$. The extracts were washed with brine, and dried with Na$_2$SO$_4$. Evaporation of solvent under reduced pressure yielded 0.53 g (41% over two steps) of the free piperidine product 19 as a colorless oil.

Step 4:

19 →

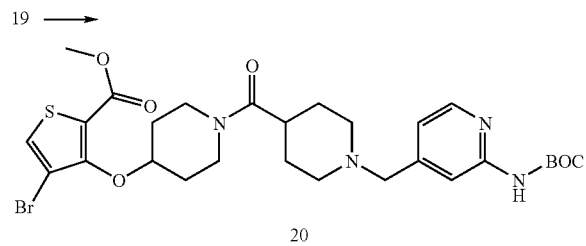

20

19 (0.52 g, 1.21 mmol) was dissolved in CH$_2$Cl$_2$ (15 ml). N-Boc-2-aminopyridine-4-carbaldehyde (0.43 g, 1.92 mmol), prepared as described in WO2002032893, NaBH(OAc)$_3$ (0.385 g, 1.82 mmol) and two drops of AcOH were added to the mixture. Reaction was continued overnight, then quenched by the addition of H$_2$O. The aqueous mixture was extracted with CH$_2$Cl$_2$ (50 ml×3). The organic extracts were washed with brine, dried over Na$_2$SO$_4$, and concentrated in vacuo to a light yellow solid, which was purified by preparative TLC(CH$_2$Cl$_2$-MeOH=25:1, v/v) to afford 0.61 g (71%) of the desired product 20 as a colorless solid.

Step 5: 20 (62 mg, 0.097 mmol) was dissolved in CH$_2$Cl$_2$ (1.5 ml) and stirred with TFA (0.5 ml) overnight. The solvent was evaporated in vacuo, the oily residue was dissolved in CH$_2$Cl$_2$ (60 ml), washed with sat NaHCO$_3$ and brine, and dried over Na$_2$SO$_4$. Evaporation of solvent gave an oily material, which was purified by preparative TLC(CH$_2$Cl$_2$-MeOH=25:1, v/v) to afford 35 mg (67%) of the title compound as a near colorless solid. MS: (M+1) 537.

Example 14

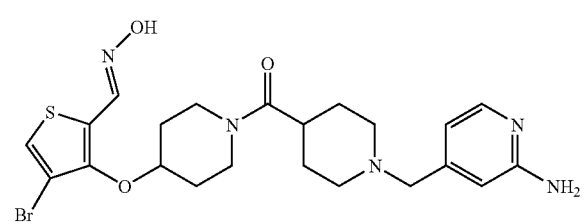

Step 1:

20 →

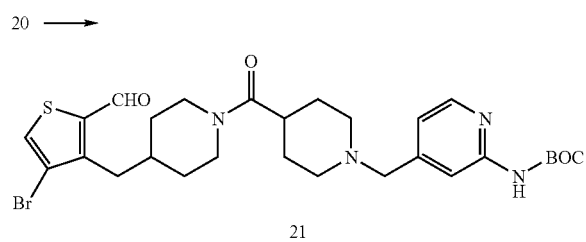

21

The thiophene ester 20 (305 mg, 0.48 mmol) was dissolved in THF (5 ml) and Et$_2$O (10 ml), cooled in an ice bath, and treated with a 1.0 M solution of LiALH$_4$ in ether (0.95 ml, 0.95 mmol). The mixture was stirred for 1.5 h at 0° C. and 10 min at RT. A small volume of H$_2$O and a 1.0 M NaOH aqueous solution were added alternately to the mixture. The mixture was diluted with EtOAc, stirred for an additional 1 h, and filtered through a 1-in silica gel pad, rinsing with EtOAc. The filtrate was concentrated in vacuo to an oil (200 mg).

The oil from above was dissolved in CH$_2$Cl$_2$ (5 ml), and N-methylmorpholino oxide (NMO) (96 mg, 0.82 mmol) was added, followed by a catalytic amount of tetrapropylamonium perruthenate (TPAP) (12 mg, 0.034 mmol). After 2 h, the mixture was quenched with H$_2$O and extracted with CH$_2$Cl$_2$. The organic extracts were washed with a 10% Na$_2$S$_2$O$_3$ aq. solution and brine, dried with Na$_2$SO$_4$, and filtered through a 1-in Celite pad. The filtrate was concentrated in vacuo to a brown oil, which was purified by preparative TLC(CH$_2$Cl$_2$-MeOH=30:1 v/v) to afford 70 mg of the desired aldehyde 21 as a colorless oil.

Step 2:

21 →

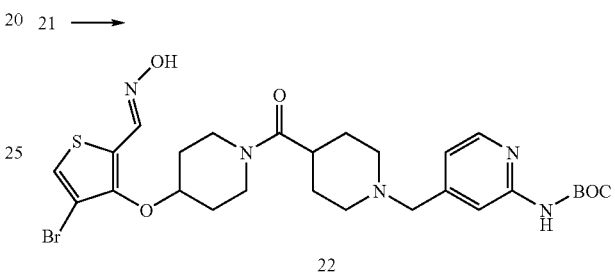

22

The aldehyde 21 (70 mg, 0.115 mmol) was dissolved in CH$_3$CN (2 ml). NaI (18 mg, 0.12 mmol) and hydroxyamine-hydrochloride (11 mg, 0.16 mmol) were added. The mixture was heated to reflux and continued overnight. Water and a 10% Na$_2$S$_2$O$_3$ aq. solution were added, and the aqueous mixture was extracted with CH$_2$Cl$_2$. The organic extracts were washed with H$_2$O and brine, dried by Na$_2$SO$_4$, and concentrated in vacuo to obtain crude 22, a colorless oil (66 mg).

Step 3: Compound 22 was converted into the title compound as described in Example 13, step 5. MS: (M+1) 522.

Example 15

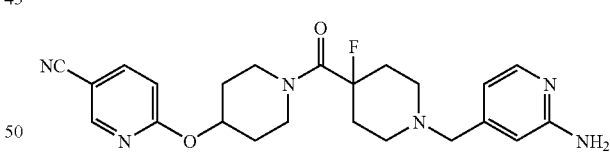

Step 1:

2 →

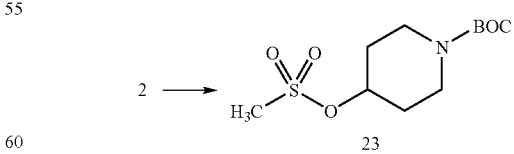

23

To a 0° C. solution of alcohol 2 (1.05 g, 5.0 mmol) in CH$_2$Cl$_2$ (50 ml) was added Et$_3$N (1.25 ml, 9.0 mmol) and CH$_3$SO$_2$Cl (542 µl, 7.0 mmol). The reaction mixture was allowed to warm to RT and was stirred for 24 h. The mixture was subjected to aqueous work-up —CH$_2$Cl$_2$ extraction. The organic phase was separated, dried over Na$_2$SO$_4$ and concentrated, and the residue was purified by flash chromatography (2-5% acetone/CH$_2$Cl$_2$) to produce 1.45 g of 23 as a white solid.

Step 2:

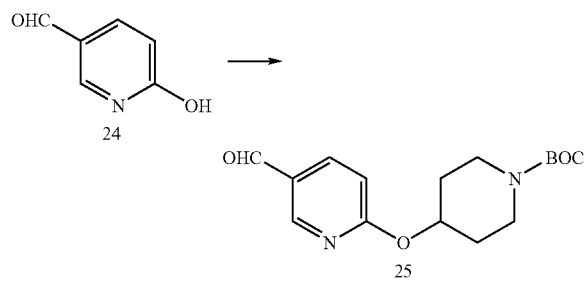

To the solution of hydroxypyridine 24 (0.29 g, 2.36 mmol) in DMF (20 ml) was added mesylate 23 (0.92 g, 3.30 mmol) and K$_2$CO$_3$ (0.71 g, 5.0 mmol). The mixture was stirred overnight at 75° C., at which point additional mesylate 23 (0.18 g, 0.65 mmol) was added, and stirring at 75° C. was continued for another 8 h. DMF was removed under vacuum, the residue was subjected to aqueous work-up —CH$_2$Cl$_2$ extraction. Organic phase was separated, dried over Na$_2$SO$_4$ and concentrated, and the residue was purified by flash chromatography (1-2% acetone/CH$_2$Cl$_2$) to produce 0.26 g of 25 as a white solid.

Step 3:

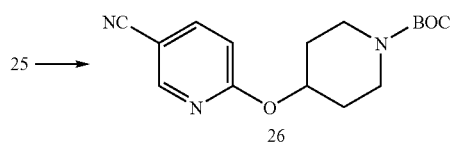

To the solution of aldehyde 25 (0.26 g, 0.85 mmol) in pyridine (10 ml) was added hydroxylamine hydrochloride (0.21 g, 3.0 mmol). The mixture was stirred overnight at 60° C. At that point, of acetic anhydride (566 µl, 6.0 mmol) was added, and the mixture was stirred for 20 h at 80° C. Pyridine was then removed under vacuum, the residue was subjected to aqueous work-up —CH$_2$Cl$_2$ extraction. The organic phase was separated, dried over Na$_2$SO$_4$ and concentrated to produce 0.26 g of crude 26 as a yellow solid.

Step 4: Compound 26 was converted into the title compound using the same procedures as in Steps 4 and 5, followed by Step 4 of Example 298. MS: (M+1) 439.

Example 16

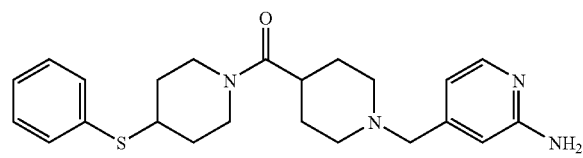

Step 1:

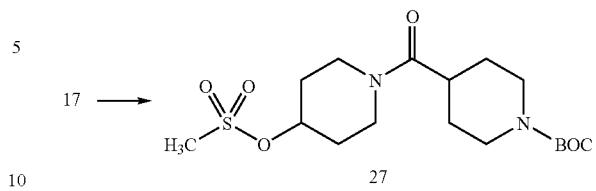

Compound 17 was converted into 27 using the procedure described in Step 1 of Example 15.

Step 2:

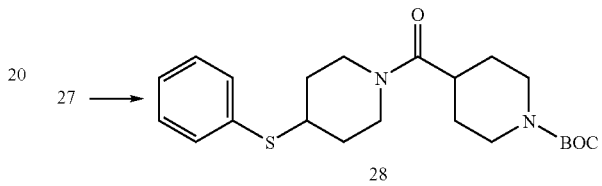

To a solution of the mesylate 27 (100 mg, 0.256 mmol) in dry MeCN was added dry K$_2$CO$_3$ (1.0 g) and PhSH (0.5 ml). The resulting mixture was heated to reflux for 17 h. The mixture was cooled to RT, filtered and concentrated in vacuo. Preparative TLC (EtOAc:Hexanes/1:1) gave the thioether 28 (60 mg) as a yellow oil.

Step 3: Compound 28 was converted into the title compound using the procedures described in Steps 3 to 5 of Example 13. MS: (M+1) 411.

Example 17

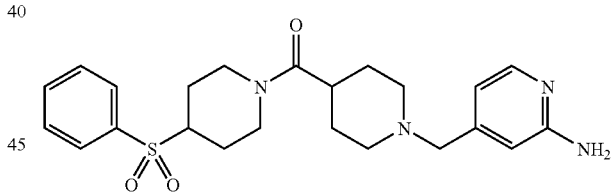

Step 1:

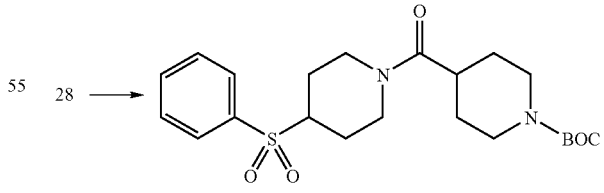

To a solution of the thioether 28 (60 mg, 0.148 mmol) in DCM (3 ml) was added mCPBA (127 mg, 0.743 mmol). The mixture was stirred at RT for 15 min and diluted with DCM. The organic phase was washed with 1N NaOH, brine, dried and concentrated in vacuo to afford the sulfone 29 (40 mg) as a yellow oil.

Step 2: Compound 29 was converted into the title compound using the procedures described in Steps 3 to 5 of Example 13. MS: (M+1) 443.

Example 18

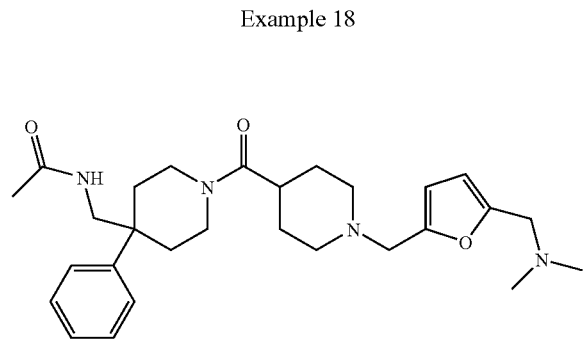

Step 1:

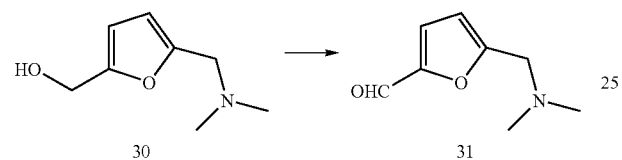

Compound 30 (5.4 g; 28.2 mmol) was dissolved in water (20 ml) topped with CH₂Cl₂ (50 ml). The mixture was made basic with 0.5N aqueous NaOH (60 ml) added in portions. Solid NaCl (10 g) was added and the organic layer separated. The aqueous layer was extracted with CH₂Cl₂ (6×50 ml). After drying with Na₂SO₄, the solvent was removed from the combined extract yielding 4.55 grams of colorless clear oil. This oil, dissolved in CH₂Cl₂ (50 ml), was stirred at RT with MnO₂ (10 g) for two days. After checking the reaction mixture, another 5 g, 3 g, and 5 g of reagent were added at 24 h intervals. The mixture was then filtered through a pad of celite, and the solid washed several times with CH₂Cl₂. Removal of the solvent using reduced pressure yielded 2.81 g of product 31 as a yellowish oil (65%).

Step 2:

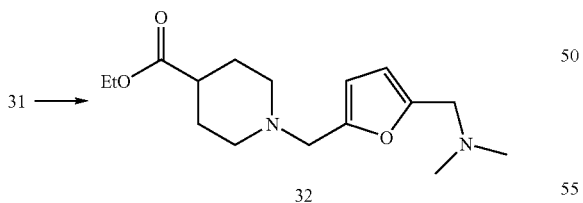

Ethyl isonipecotate (3.62 g.; 23 mmol) and 31 (1.73 g, 17.8 mmol) were stirred at RT in 15 ml of CH₂Cl₂ for 90 min. NaBH(OAc)₃ (4.24 g, 20 mmol) was then added, and the mixture stirred under N₂ for 20 h. The mixture was diluted with CH₂Cl₂, washed with saturated aqueous NaHCO₃, then with brine, and dried with anhydrous Na₂SO₄. After removing the solvent using reduced pressure, the reaction mixture was purified by flash chromatography using silica gel as the solid phase EtOAc:Hexanes:MeOH(NH3) (60:35:5) as eluent. Yield: 4.53 g (67%) of product 32.

Step 3:

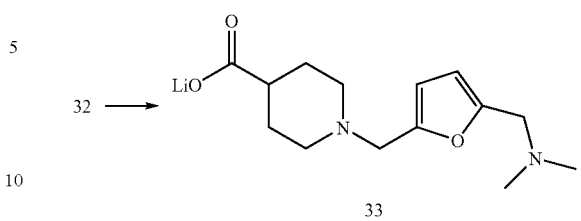

The product 32 (3.84 g; 13.04 mmol) and lithium hydroxide monohydrate (1.1 g; 26.1 mmol) were stirred at RT for 24 h in water (20 ml) and MeOH (20 ml). After filtering the solids, the solvents were removed using reduced pressure at a bath temperature of 55° C. Crude 33 (3.80 g) was used directly.

Step 4: Compound 33 was converted into the title compound using the procedures described in Steps 2 and 3 of Example 5. MS: (M+1) 481.

Example 19

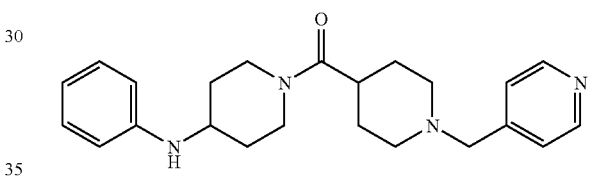

Step 1:

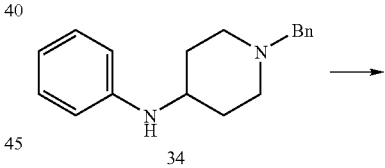

Compound 34 (10 g; 37.54 mmol) was dissolved in MeOH (100 ml) and treated with p-toluene sulfonic acid (7.48 g; 39.4 mmoles). After removing the solvent using reduced pressure, the resulting salt was dissolved in absolute EtOH (100 ml), Pd/C (4.0 g of 10%) was added, and the mixture hydrogenated at RT for 20 h. More catalyst was added (2.2 g), and the mixture was hydrogenated for another 6 h. The catalyst was then removed through a pad of celite and washed with absolute EtOH. Removal of the solvent using reduced pressure gave 13.34 g of pTSA salt of 35.

Step 2: Compound 35 was converted into the title compound using the procedures, described in Steps 3 and 4 of Example 1. MS: (M+1) 379.

Example 20

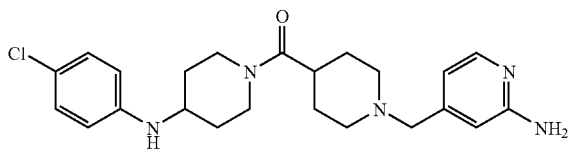

Step 1:

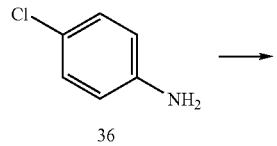

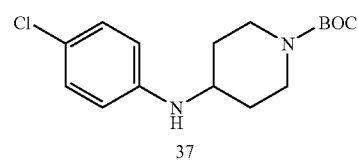

Compound 36 (1.91 g; 15 mmol) was added at RT to t-butyl 4-oxo-1-piperidine (2.0 g, 10 mmol) dissolved in dry CH$_2$Cl$_2$ (20 ml). After 4 h, NaBH(OAc)$_3$ (4.2 g, 19.8 mmol) was added in one portion. The mixture was stirred at RT for 19 h, then diluted with CH$_2$Cl$_2$ (100 ml), shaken with saturated aqueous NaHCO$_3$, washed with brine, and dried with anhydrous Na$_2$SO$_4$. The product was purified by flash chromatography (SiO$_2$) using 10% EtOAc/Hexanes as eluent to produce 1.16 g of 37.

Step 2: Compound 37 was converted into the title compound using the procedures described in Steps 24 of Example 1. MS: (M+1) 428.

Example 21

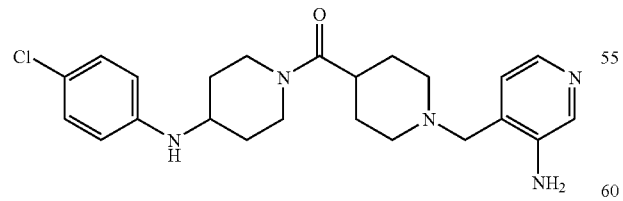

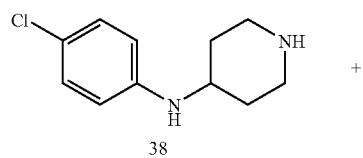

+

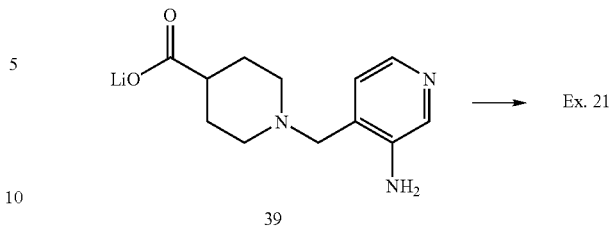

Compound 38 was prepared as described in Ex. 20. Preparation of compound 39 was described in U.S. Pat. No. 6,720,328. Preparation of the title compound from 38 and 39 was effected as described in Ex. 1, Steps 3 and 4. MS: (M+1) 428.

Example 22

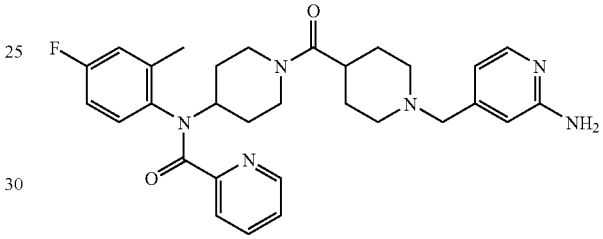

Step 1:

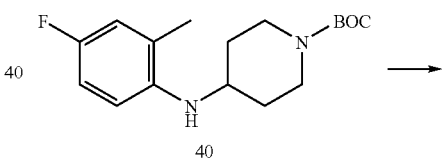

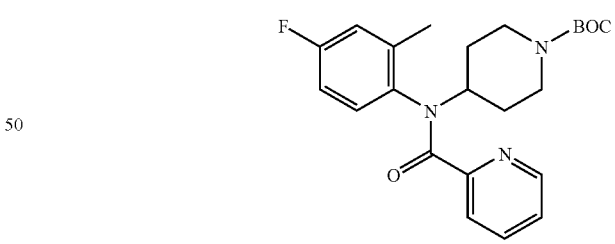

Compound 40 was prepared as described for compound 37 in Example 20.

Conversion of 40 into 41 was effected with 2-picolinic acid chloride and DIPEA using a procedure known in the art.

Step 2: Compound 41 was converted into the title compound using the procedures of Steps 2 to 4 of Example 1. MS: (M+1) 531.

Examples 23 and 23A

Example 24

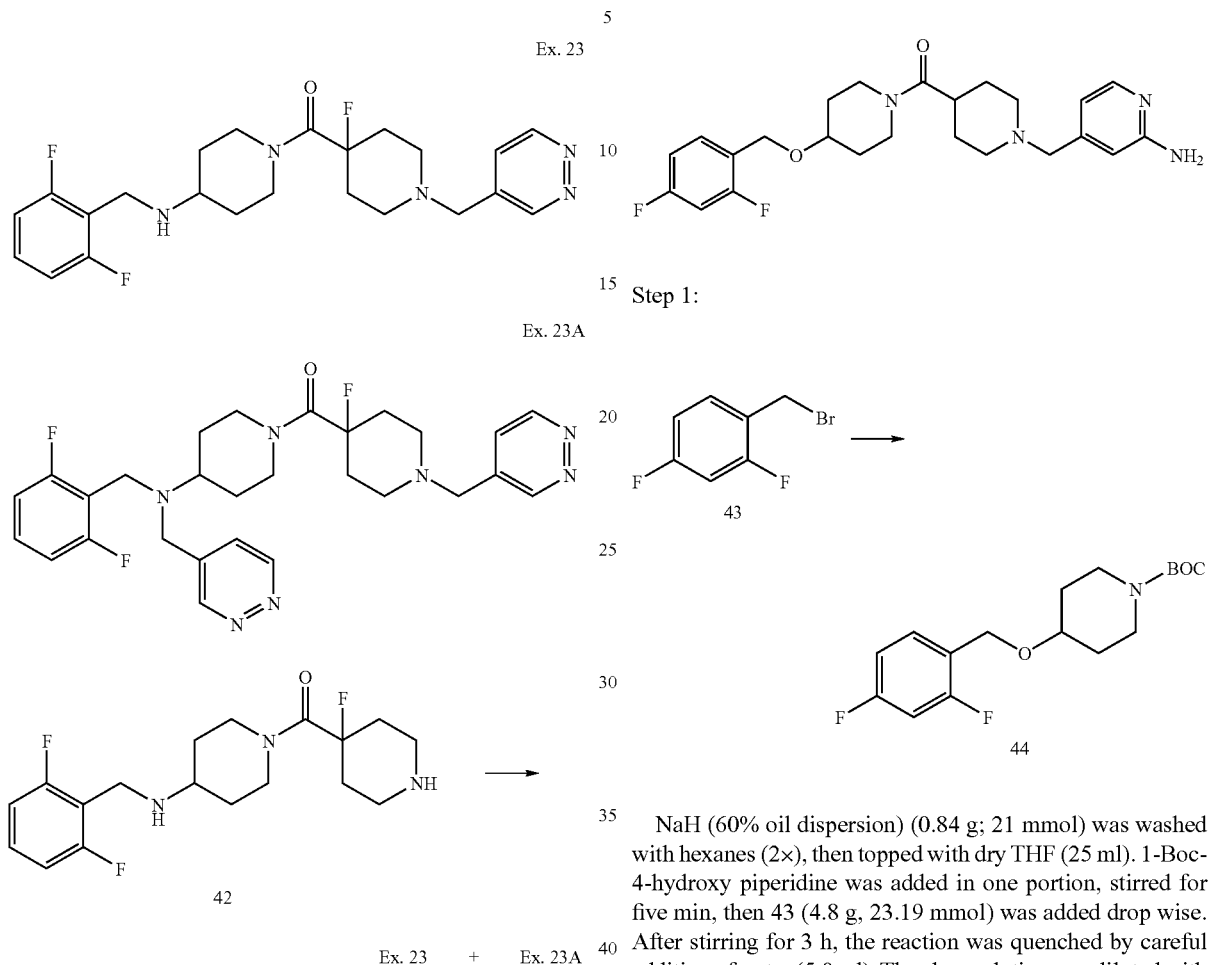

Step 1:

Compound 42 was prepared using the procedure described for preparing compound 37, followed by BOC deprotection as described in the conversion of 3 into 4 in Example 1, followed by EDC mediated coupling with N-BOC-α-fluoroisonipecotic acid, followed by BOC deprotection.

Compound 42 (0.41 g; 1.22 mmol) and pyridazine-4-carbaldehyde (0.2 g; 1.82 mmol) (prepared as described in U.S. Pat. No. 6,720,328) were stirred at RT in dry $CH_2Cl_2$ (14 ml) containing activated molecular sieves (5.0 g). After 4 h, NaBH(OAc)$_3$ (1.27 g; 6.0 mmol) was added in one portion, and the mixture stirred for 20 h. After diluting with 30 ml of $CH_2Cl_2$, the mixture was filtered, and the filtrate stirred with saturated aqueous NaHCO$_3$. The aqueous layer was extracted with $CH_2Cl_2$; the extracts were combined, washed with brine and dried over anhydrous Na$_2$SO$_4$. The reaction mixture was partially purified by flash chromatography on silica gel using first 100% $CH_2Cl_2$, then 2.5% MeOH(NH$_3$)/$CH_2Cl_2$, and 5% MeOH(NH$_3$)/$CH_2Cl_2$ as eluent. The components of the mixture were separated by preparative TLC on silica gel using 5% MeOH(NH$_3$)/$CH_2Cl_2$ as mobile phase. This gave 0.17 g of Example 23 and 0.054 g of Example 23A. 23: MS: (M+1) 430; 23A: MS: (M+1) 522.

NaH (60% oil dispersion) (0.84 g; 21 mmol) was washed with hexanes (2×), then topped with dry THF (25 ml). 1-Boc-4-hydroxy piperidine was added in one portion, stirred for five min, then 43 (4.8 g, 23.19 mmol) was added drop wise. After stirring for 3 h, the reaction was quenched by careful addition of water (5.0 ml). The clear solution was diluted with EtOAc, the aqueous layer was separated and extracted with EtOAc. The combined extracts were washed with brine, dried over anhydrous Na$_2$SO$_4$, then purified by flash chromatography on silica gel using 10% EtOAc/Hexanes as mobile phase to yield 4.79 g (73%) of 44 as a colorless oil.

Step 2: Compound 44 was converted into the title compound using the procedures described in Steps 2 to 4 of Example 1. MS: (M+1) 445.

Example 25

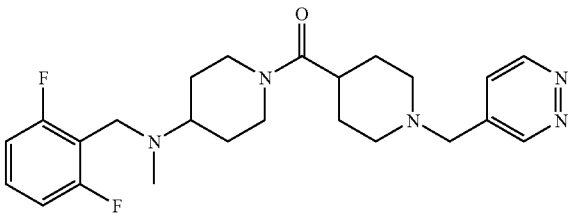

Step 1:

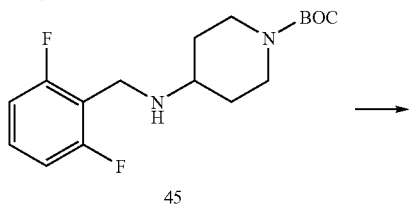

Compound 45 (3.56 g, 10.91 mmol) and anhydrous K₂CO₃ (4.52 g, 32.73 mmol) were treated at RT in dry DMF (15 ml) with CH₃I (0.88 ml, 14.18 mmol). After 4 days, water (50 ml) was added and the mixture was extracted with CH₂Cl₂. The combined extracts were washed with brine, and then dried over anhydrous Na₂SO₄. Purification by flash chromatography on silica gel using 5% MeOH(NH₃)/CH₂Cl₂ as eluent gave 2.2 g of product 46.

Step 2: Compound 46 was converted into the title compound using the procedures described in Steps 2 to 4 of Example 1. MS: (M+1) 444.

Example 26

General Scheme

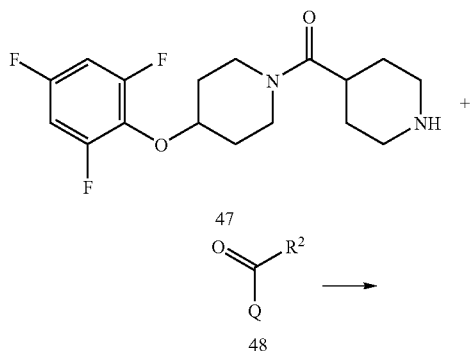

-continued

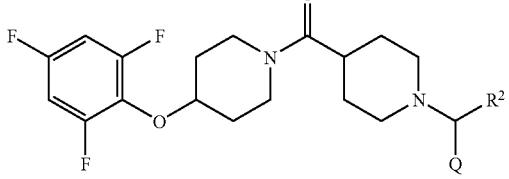

Q = H, R'

A stock solution of 47 (1 ml, 0.024 mmol) (prepared by using procedures as described for the synthesis of compound 4 in Example 1, followed by procedures similar to those used in the synthesis of compound 42 in Example 23) in DCE containing 1% AcOH was added to 96-wells of a deep well polypropylene microtiter plate. A 1 M stock solution of each of the individual aldehydes (Q=H) and ketones (Q=R') in DCE (0.117 ml, 0.117 mmol) were then added to the wells, followed by a MeCN solution of tetramethylammonium-triacetoxyborohydride (18 mg, 0.0846 mmol). The microtiter plate was then sealed and shaken at 25° C. for 20 h. The solutions were filtered through a polypropylene frit into a second microtiter plate containing MP-TsOH resin (~100 mg). After the top plate was washed with MeCN (0.5 ml), the plate was removed, the bottom microtiter plate sealed and shaken at 25° C. for 2 h. The solutions were filtered through a polypropylene frit and the resin was washed with CH₂Cl₂ (3×), then MeOH (3×) to remove unreacted reagents. After the plate was allowed to sit for 10 min, the bottom microtiter plate was sealed, NH₃ in MeOH (2 N. 1 ml) was added to each well, the microtiter plate was sealed, and then shaken at 25° C. for 1 h. Then the solutions were filtered thru a polypropylene frit into a 96-well collection plate. The wells of the top plate were then washed with MeOH (0.5 ml), and the plate removed. Then the resulting solutions in the collection plate were transferred into vials and the solvents removed in vacuo via a SpeedVac concentrator. The resulting samples were evaluated by LCMS and were 70%-90% pure. Yields: 60%-80%. Individual compounds were then resynthesized on a larger scale, as needed, using the same procedure as used for the conversion of compound 42 into Example 23.

| Ex. No. | Structure | MS (M + 1) |
|---|---|---|
| 26A | 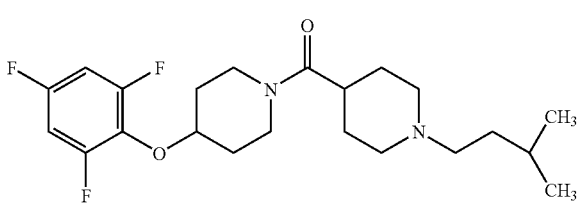 | 413 |

-continued

| Ex. No. | Structure | MS (M + 1) |
|---|---|---|
| 26B | 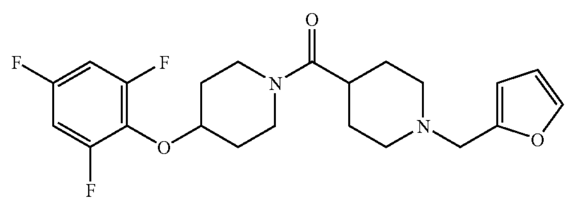 | 423 |
| 26C | 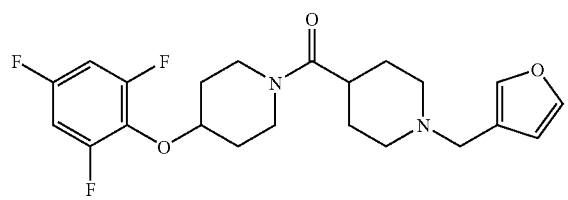 | 423 |
| 26D | 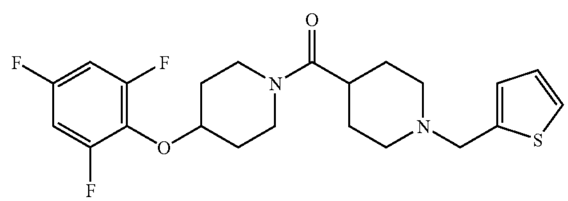 | 439 |
| 26E | 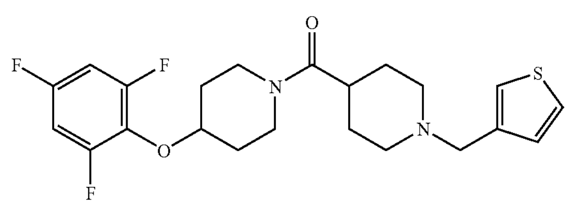 | 439 |
| 26F | 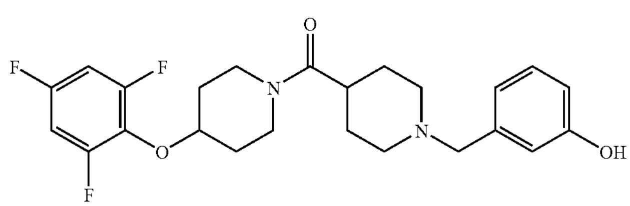 | 449 |
| 26G | 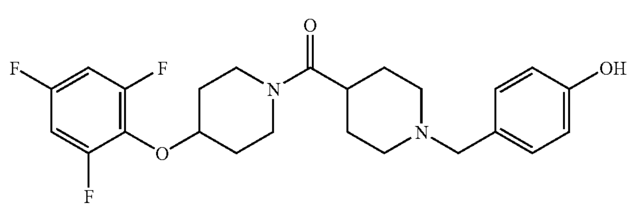 | 449 |
| 26H | 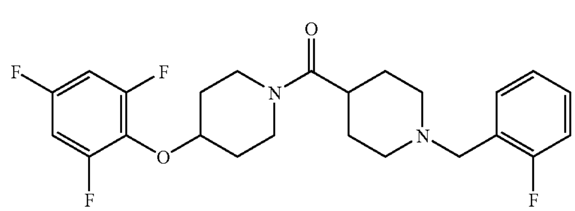 | 451 |

-continued
| Ex. No. | Structure | MS (M + 1) |
|---|---|---|
| 26I | 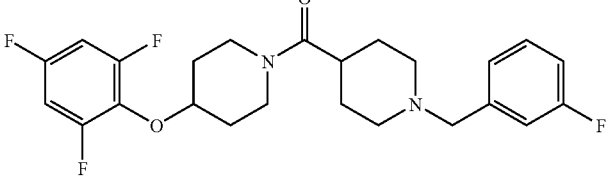 | 451 |
| 26J | 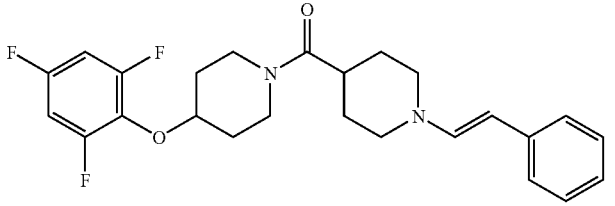 | 459 |
| 26K | 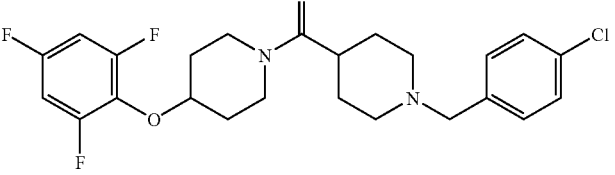 | 467 |
| 26L | 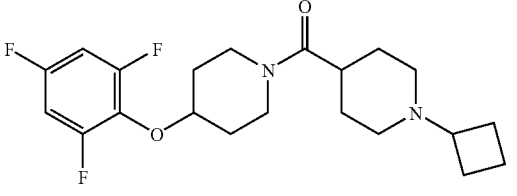 | 397 |
| 26M | 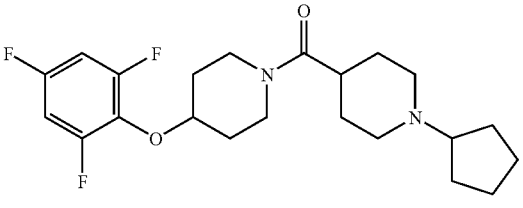 | 411 |
| 26N | 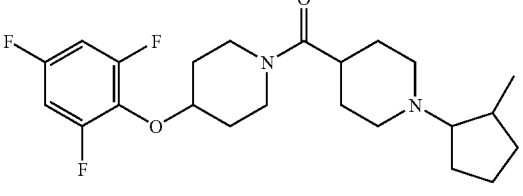 | 425 |
| 26O | 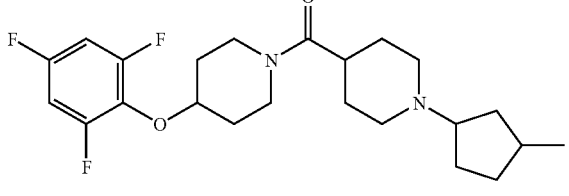 | 425 |

-continued

| Ex. No. | Structure | MS (M + 1) |
|---|---|---|
| 26P | 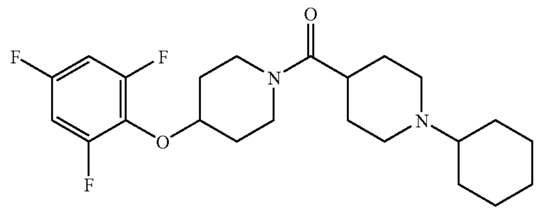 | 425 |
| 26Q | 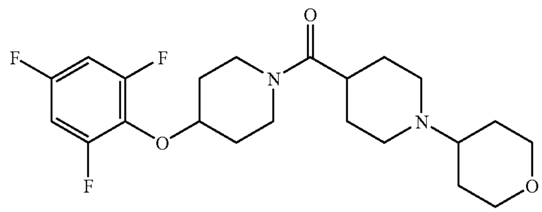 | 427 |
| 26R | 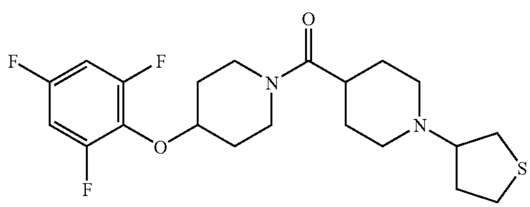 | 429 |
| 26S | 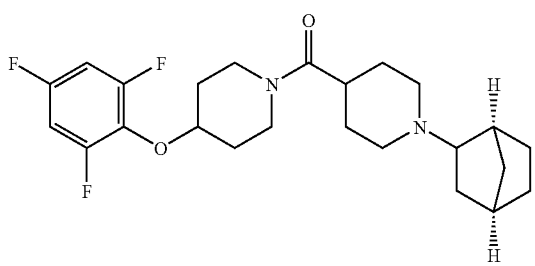 | 437 |
| 26T | 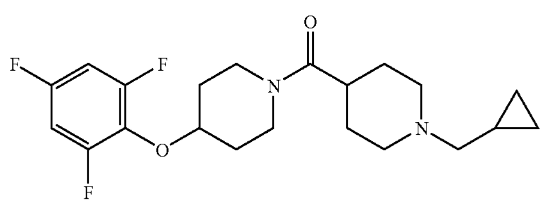 | 397 |
| 26U | 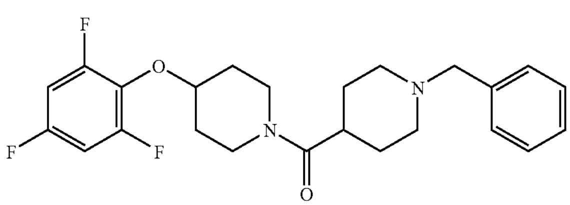 | 433 |

Example 27

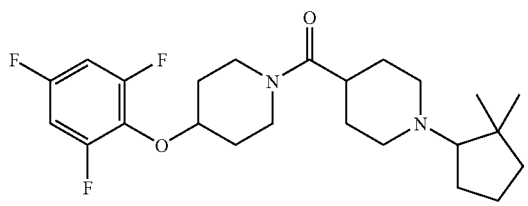

2,2-Dimethylcyclopentanone (0.10 g, 2.0 eq) was added to a 0.02 M solution of 47 in $CH_2Cl_2$. Titanium tetraisopropoxide (0.15 ml, 1.2 eq) was added and the resulting mixture was stirred at RT for 2.5 h, $NaBH(OAc)_3$ (0.18 g, 2.0 eq) was added and the stirring was continued for 15 h. The mixture was diluted with $CH_2Cl_2$ (50 ml) and washed with aq sat $K_2CO_3$ (50 ml). The layers were separated and the aq layer extracted with $CH_2Cl_2$ (2×50 ml). The combined organic phase was dried, the solvent evaporated in vacuo and the residue purified by column chromatography ($SiO_2$, $CH_2Cl_2$: 0.4 N $NH_3$ in MeOH 95:5) to give the title compound (0.016 g, 9%) as a yellow oil. MS: (M+1) 439.

Example 28

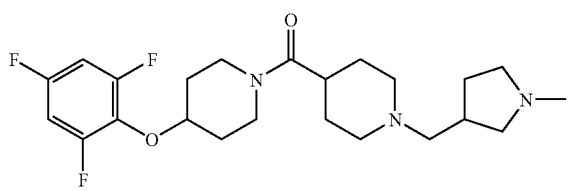

Step 1:

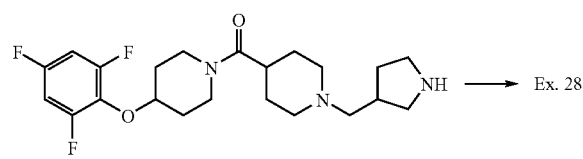

Ex. 28A

Example 28A was prepared from 47 using procedure of Example 23, followed by BOC-deprotection. MS: (M+1) 426.

Step 2: A solution of Example 28A (0.107 g), a mixture of 37% aq formaldehyde (2 ml) and formic acid (1 ml) was heated at reflux for 16 h, then diluted with $CH_2Cl_2$ (30 ml) and washed with aq sat $K_2CO_3$ (30 ml). The aq. layer was extracted with $CH_2Cl_2$ (2×30 ml), and the combined organic phase dried. The solvent was evaporated under vacuo and the residue purified by column chromatography ($SiO_2$, $CH_2Cl_2$: 0.4 N $NH_3$ in MeOH 3:1) to give Example 28 (0.052 g, 47%) as colorless crystals. MS: (M+1) 440.

Example 29

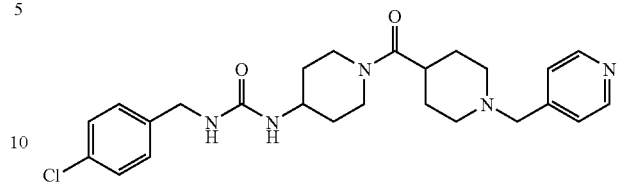

Step 1:

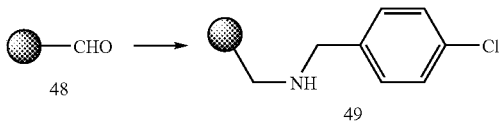

To a DCE solution (150 ml) of 2-(4-formyl-3-methoxy)phenoxyethylpolystyrene resin 48 (2.8 g, 2.184 mmol) at RT was added 4-chlorobenzylamine (43.68 mmol, 20 equiv) followed by $NaBH(OAc)_3$ (9.25 g, 20 equiv). The flask was capped and shaken at RT for 3 days. The reaction was quenched by the addition of 2M $NH_3$ in MeOH. The resin was then washed with MeOH (3×), THF (3×), and $CH_2Cl_2$ (3×) and then dried in vacuo to provide 49.

Step 2:

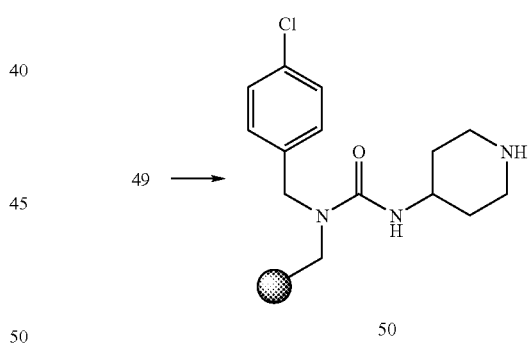

To a $CH_2Cl_2$ solution (6 ml) of 49 (70 mg, 0.0546 mmol) and $Et_3N$ (0.23 ml, 30 equiv) at 0° C. was added dropwise a $CH_2Cl_2$ (2 ml) solution of triphosgene (57 mg, 4 equiv). The solution was then capped and shaken at RT for 6.5 h. The resin was then washed with $CH_2Cl_2$ (3×) and dried in vacuo. To this resin in $CH_2Cl_2$ (6 ml) was added pyridine (0.022 ml, 5 equiv) and then 4-amino-1-trityl-piperidine (93.5 mg, 5 equiv). The suspension was sealed and heated at 60° C. for 12 h. The resin was then washed with MeOH (3×), THF, then $CH_2Cl_2$ and dried in vacuo. The resin was then treated multiple times (8-10) with 0.1 N TFA in $CH_2Cl_2$ containing 20% triethylsilane for 5-10 mins each. The resin was then washed with $CH_2Cl_2$ (4×) and dried in vacuo to provide resin 50.

51

Step 3:

50 ⟶

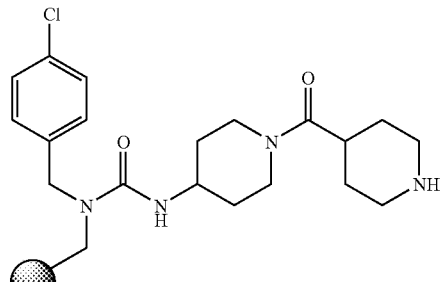

51

A CH₂Cl₂ solution of 50 (70 mg, 0.0546 mmol) and DIEA (0.19 ml, 20 equiv) was treated with a CH₂Cl₂ solution of the acid chloride of FMOC-isonipecotic acid (2 equiv). The suspension was shaken at RT for 20 h, then the resin was washed with MeOH (3×), then CH₂Cl₂ and dried in vacuo. The resin was then treated three times with 20% piperidine in DMF for 20 min each, then washed (3×) with DMF, THF and CH₂Cl₂, then dried in vacuo to provide 51.

52

Step 4:

51 ⟶

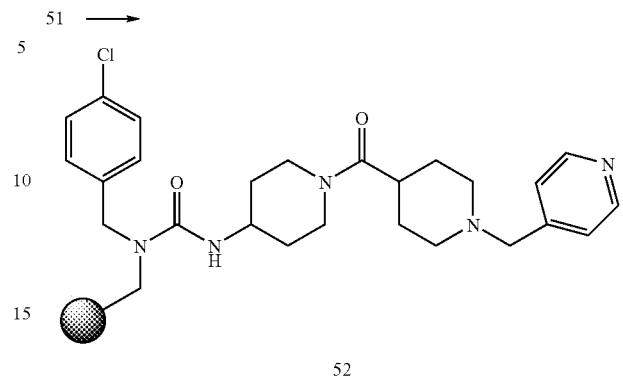

52

To a DCE solution (5 ml) of 51 (70 mg, 0.0546 mmol) at RT was added pyridine-4-carboxaldehyde (0.11 ml, 20 equiv), then NaBH(OAc)₃ (70 mg, 10 equiv). The flask was capped and shaken at RT for 2 days. The resin was then washed (3× each) with MeOH and CH₂Cl₂, then dried in vacuo to provide 52.

Step 5: The product was cleaved off the resin by treatment of 52 twice for 20 min each with 40% TFA in CH₂Cl₂; the solutions were transferred into vials and the solvent removed in vacuo via a SpeedVac to provide the title compound. MS: (M+1) 470.

Using analogous solid support synthesis procedures, the following compounds were prepared.

| EX. | Structure | MS (M + 1) |
|---|---|---|
| 29A | 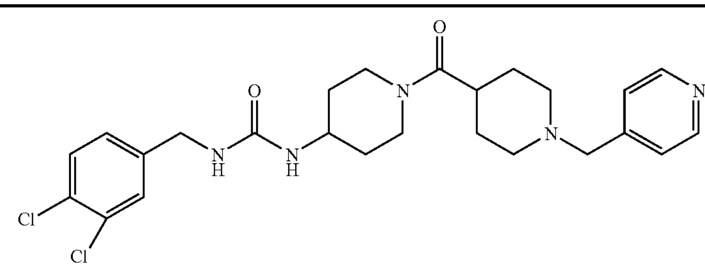 | 467 |
| 29B | 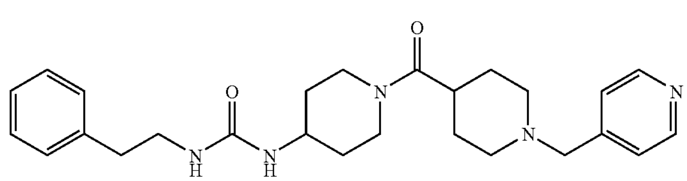 | 450 |
| 29C | 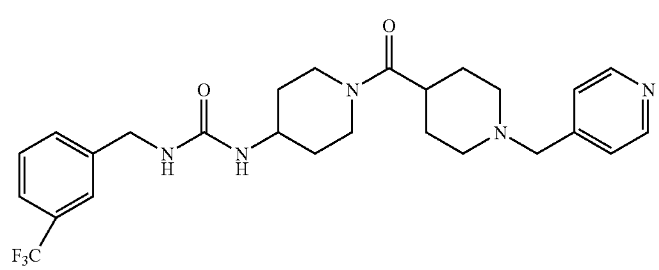 | 504 |

| EX. | Structure | MS (M + 1) |
|---|---|---|
| 29D | 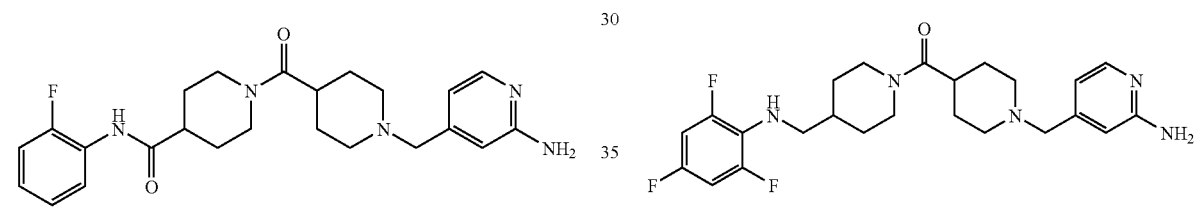 | 436 |
| 29E | 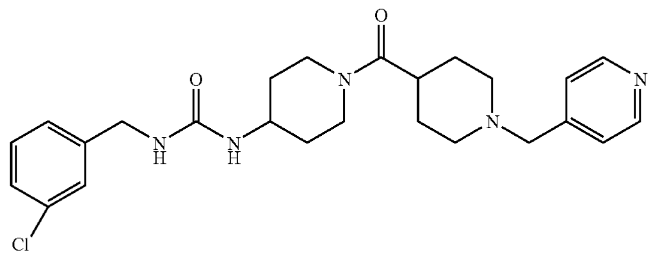 | 470 |

Example 30

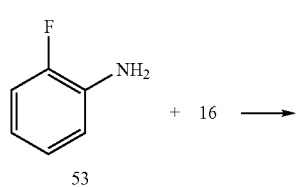

Step 1:

Compound 53 was converted into compound 54 using a procedure analogous to Step 3 of Example 1.

Step 2: Compound 54 was converted into the title compound using procedures analogous to Steps 2 to 4 in Example 1. MS: (M+1) 440.

Example 31

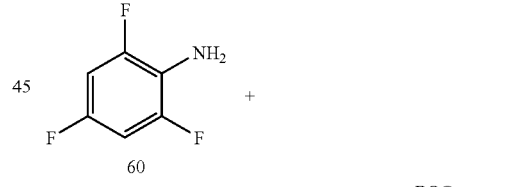

Step 1:

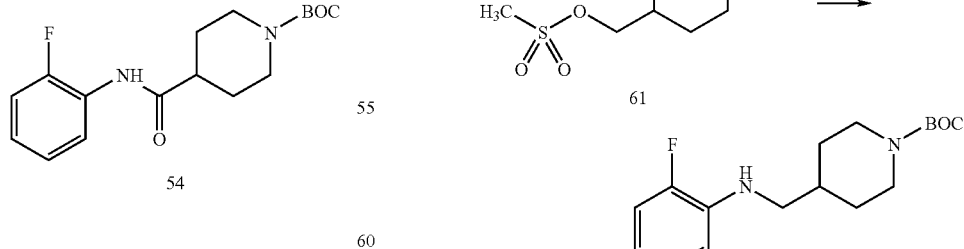

A 60% dispersion of NaH (480 mg, 12.0 mmol) was added to a solution of 60 (1.76 g, 12.0 mmol) in DMF at RT under N₂. After stirring at ambient temperature for 30 min, compound 61 (2.93 g; 10.0 mmol), prepared as described for compound 23 in Example 16, was added, and the resultant mixture was stirred at RT for 16 h. H$_2$O (20 ml) and EtOAc (50 ml) were added, and the organic layer was separated and washed with H$_2$O (20 ml), then dried over anhydrous MgSO$_4$ and concentrated under vacuum. The residue was purified by flash column chromatography (hexanes-EtOAc; 8:1), to obtain 62 as a yellow solid (1.72 g, 50%).

Step 2: Compound 62 was converted into the title compound using procedures analogous to Steps 2 to 4 in Example 1. MS: (M+1) 462.

Example 32

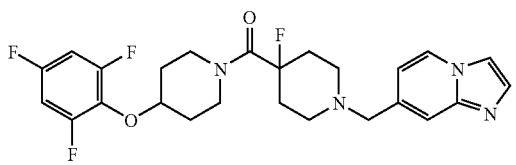

Step 1:

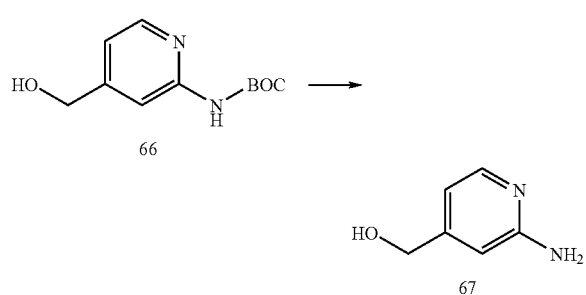

To a stirred, ice-cooled solution of compound 66 (3.68 g, 16.4 mmol), prepared as described in U.S. Pat. No. 6,720,328, in CH$_2$Cl$_2$ (50 ml) was added ice-cold TFA (6.07 ml, 9.38 g, 82.1 mmol) via syringe over a period of ~1 min. The resultant clear yellow solution was stirred at 0° C. for 10 min, then at RT for 25 h. Volatiles were removed under reduced pressure, and the residue was redissolved in CH$_2$Cl$_2$ (35 ml). To this solution was added portionwise (exothermic) 7N methanolic ammonia (5 ml, 35 mmol), making the solution basic to pH paper and resulting in the formation of a precipitate. Solvent was removed under reduced pressure, and the residue was triturated with EtOAc (30 ml). The mixture was filtered, the filtrate was stripped of solvent under reduced pressure, and the residue was purified via flash chromatography on silica gel, eluting with CH$_2$Cl$_2$-MeOH —NH$_3$ (90:9:0.25), to obtain compound 67 as an off-white powder (1.43 g; 70%).

Step 2:

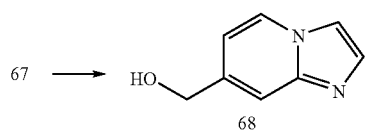

To a stirred solution of 67 (1.39 g, 11.2 mmol) in EtOH (46.5 ml)-water (6.5 ml) was added NaHCO$_3$ (1.88 g, 22.3 mmol), followed by a 50% w/w aqueous solution of chloroacetaldehyde (2.84 ml, 1.75 g, 22.4 mmol). The resultant suspension was stirred and refluxed for 2 h. The dark amber-colored reaction mixture was carefully concentrated (frothing) under reduced pressure to approximately half its original volume and then filtered. Collected solid was washed with MeOH. Combined filtrate and washings were concentrated in vacuo and yielded a dark, oily two-phase mixture. Treatment with EtOH produced a mixture of solid precipitate and a homogeneous liquid phase, which was filtered. The filtrate was concentrated under reduced pressure to a dark oil, which was purified via flash chromatography on silica gel, eluting with CH$_2$Cl$_2$—CH$_3$OH —NH$_4$OH (91.5:8.5:0.25), to obtain compound 68 as a pale yellow solid (1.34 g; 80%). To a solution of 68 (1.20 g, 8.10 mmol) in MeOH (5 ml) was added acetone (48 ml). A small amount of dark precipitate formed and was removed by filtration (0.45 µM syringe filter). To the clear yellow filtrate was added via syringe 1M ethereal HCl (8.1 ml, 8.1 mmol). The resultant mixture was stirred briefly and was then filtered. The hygroscopic solid thus isolated was washed rapidly with acetone and dried under vacuum at 50° C. to obtain the hydrochloride salt of 68 as a tan powder (1.34 g; 89%).

Step 3:

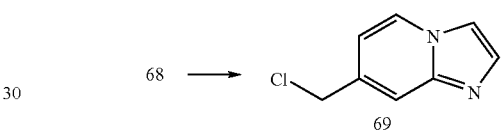

To a stirred suspension of the hydrochloride salt of 68 (1.32 g, 7.15 mmol) in CHCl$_3$ (13 ml), SOCl$_2$ (785 microliters, 1.28 g, 10.7 mmol) was added via syringe in three quick successive portions. The resultant cloudy brown mixture of liquid phases was stirred for 2 h at RT. Volatile components were removed under reduced pressure, and the solid residue was triturated twice with acetone (1×13 ml, 1×10 ml). Filtration and washing with acetone and diisopropyl ether yielded hydrochloride salt of 69 as a brown powder (1.27 g; 87%).

Step 4:

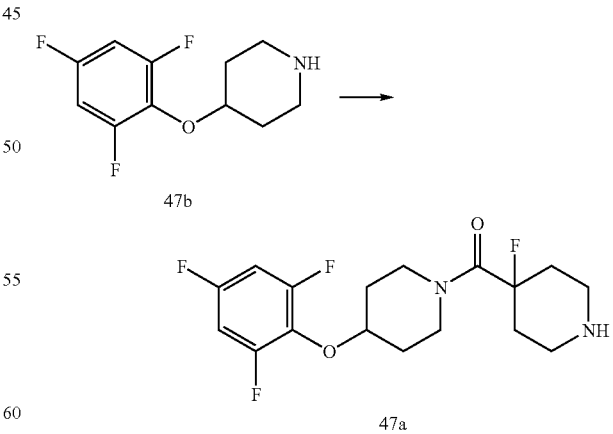

Compound 47b was prepared using the procedures analogous to those of steps 1 and 2 from example 1 and converted into 47a by using the procedure analogous to step 5 of example 296, followed by procedure analogous to step 3 of example 13.

Step 5:

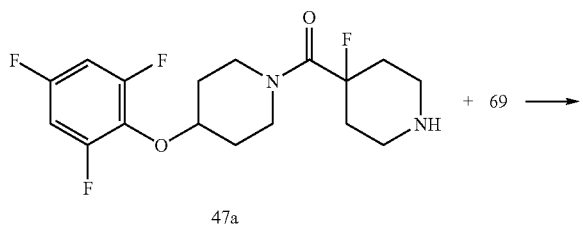

To a stirred solution of amine 47a (220 mg, 0.644 mmol) in DMF (7.5 ml) were added successively $K_2CO_3$ (297 mg, 2.15 mmol), KI (an unweighed catalytic quantity) and chloride 69 (150 mg, 0.741 mmol). The resultant yellow mixture was placed in a preheated oil bath and stirred for 12 h at 50° C. The reaction mixture was allowed to cool to RT and was then filtered through a pad of Celite on a sintered glass funnel. The pad was washed thoroughly with $CH_2Cl_2$, and filtrate and washings were stripped of solvent under reduced pressure. The residue was purified via flash chromatography on silica gel, eluting with $CH_2Cl_2$—$CH_3OH$—$NH_3$ (97:3:0.25), to obtain the title compound as an off-white powder (203 mg; 66%). MS: (M+1) 473.

Example 33

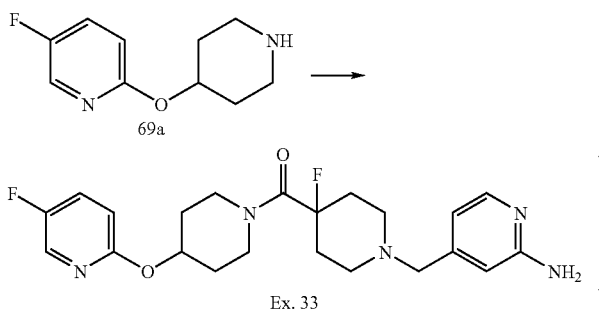

Compound 69a was prepared using the procedures described for the conversion of compound 24 into 25 in Example 15, followed by BOC-deprotection under the conditions described in Step 4 of Example 1.

Compound 69a was converted into the title compound using procedures analogous to Steps 2 to 4, followed by Step 4 of Example 298. MS: (M+1) 432.

Example 34

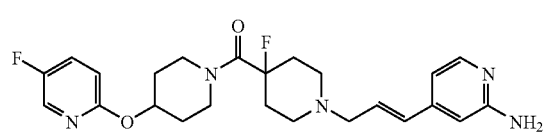

Step 1:

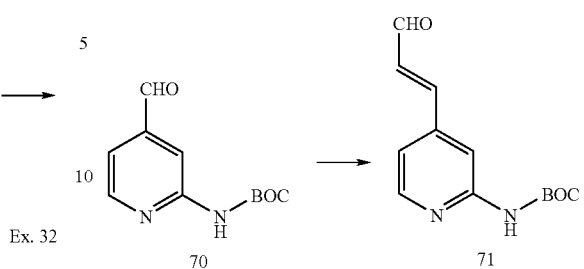

To a solution of 70 (5.0 g, 22.5 mmol) in 150 THF (150 ml) was added (triphenylphosphoranylidene)acetaldehyde (9.0 g, 30.0 mmol), and the mixture was stirred for 6 h at RT. The reaction mixture was diluted with water and aqueous $NH_4Cl$, and the pH was adjusted to 7. The mixture was then extracted with $CH_2Cl_2$, the organic phase was separated, dried ($Na_2SO_4$) and concentrated, and the residue was flash chromatographed ($CH_2Cl_2$) to produce 5.56 g of 71 as a yellowish solid.

Step 2:

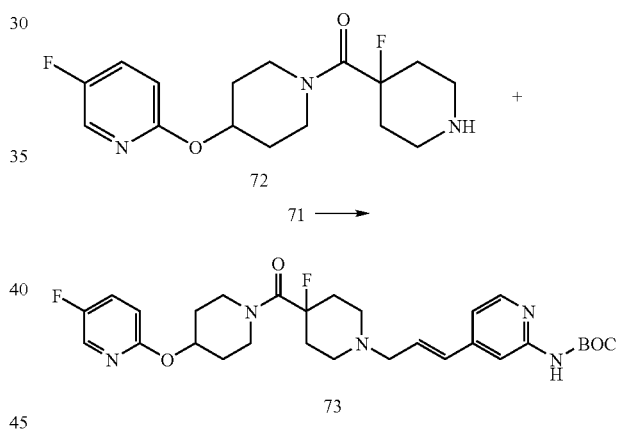

Compound 72 was prepared in two steps from compound 69a using procedures analogous to Steps 3 and 4 of Example 1. Conversion of 72 into 73 was accomplished using procedure of Step 3 in Example 1.

Step 3: Compound 73 was converted into the title compound using a procedure analogous to Step 4 of Example 1. MS: (M+1) 458.

Example 35

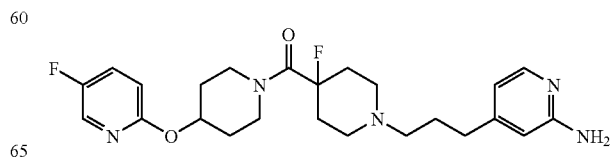

Step 1:

73 ⟶

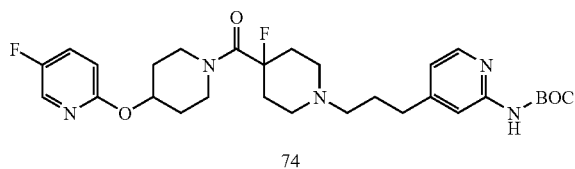

74

A solution of olefin 73 (0.28 g, 0.50 mmol) in MeoH (10 ml) was charged with 10% Pd/C (0.05 g), and the mixture was stirred under H₂ balloon (1 atm.) overnight. The catalyst was filtered off and washed with MeOH and the filtrate was concentrated to produce 0.26 g of 74 as a clear oil.

Step 2: Compound 74 was converted into the title compound using a procedure analogous to Step 4 of Example 1. MS: (M+1) 460.

Example 36

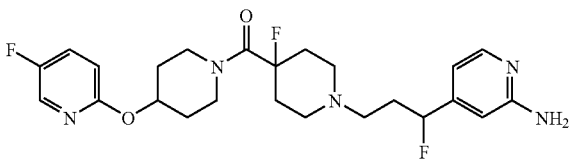

Step 1:

70 ⟶

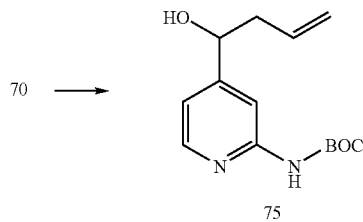

75

To a -78° C. solution of 70 (4.0 g, 18.0 mmol) in THF (120 ml) was slowly added a 1M ether solution of allylmagnesium bromide (45 ml). The reaction mixture was stirred at -78° C. for 2 h, then allowed to warm to RT. The reaction mixture was quenched with water, neutralized with AcOH and extracted with CH₂Cl₂. The organic phase was separated, dried (Na₂SO₄) and concentrated, and the residue was flash chromatographed (0-0.5% MeOH/CH₂Cl₂) to produce 3.83 g of alcohol 75 as a yellowish foam.

Step 2:

75 ⟶

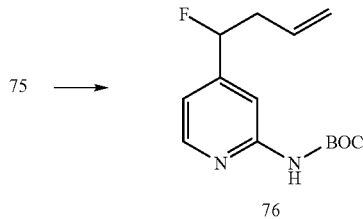

76

To a -78° C. solution of alcohol 75 (1.0 g, 3.78 mmol) in CH₂Cl₂ (25 ml) was added diethylaminosulfur trifluoride (DAST) (0.7 ml, 5.67 mmol). The reaction mixture was stirred for 1 h at -78° C., warmed up to RT, and diluted with water and aqueous NaHCO₃. The mixture was extracted with CH₂Cl₂. The organic phase was separated, dried (Na₂SO₄) and concentrated, and the residue was flash chromatographed (CH₂Cl₂) to produce 0.614 g of 76 as a clear oil.

Step 3:

76 ⟶

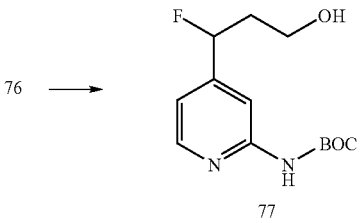

77

Ozone was passed through a -78° C. solution of 76 (1.0 g, 3.76 mmol) in a 1:1 mixture of MeOH—CH₂Cl₂ (20 ml) until the solution turned blue. The solution was purged for 5 min. with oxygen, after which NaBH₄ (0.7 g, 18.8 mmol) was added in portions, and reaction mixture was allowed to warm to RT. The reaction mixture was diluted with aqueous NH₄Cl and extracted with CH₂Cl₂. The organic phase was separated, dried (Na₂SO₄) and concentrated to produce 1.0 g of crude alcohol 77, which was used without purification.

Step 4:

77 ⟶

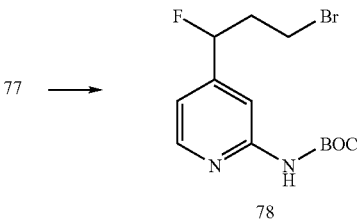

78

To a solution of crude alcohol 77 (1.0 g, 3.70 mmol) in a 1:1 mixture of CH₂Cl₂-CH₃CN (5 ml) was added dibromotriphenylphosphorane (2.34 g, 5.54 mmol). The reaction mixture was stirred at RT for 3 h, diluted with aqueous NaHCO₃ and extracted with CH₂Cl₂. The organic phase was separated, dried (Na₂SO₄) and concentrated, and the residue was flash chromatographed (0-0.5% MeOH/CH₂Cl₂) to produce 0.79 g of bromide 78 as a clear oil.

Step 5:

72 + 78 ⟶

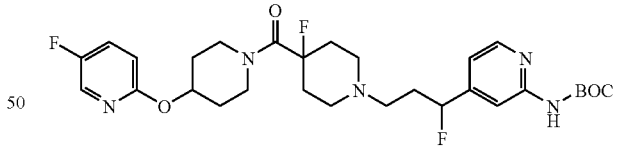

79

A mixture of 72 (0.038 g, 0.117 mmol), 78 (0.03 g, 0.090 mmol) and K₂CO₃ (0.025 g; 0.18 mmol) in DMF (2 ml) was stirred at RT for 2 days. DMF was removed under vacuum, and the mixture was partitioned between water and CH₂Cl₂. The organic phase was separated, dried (Na₂SO₄) and concentrated, and the residue was flash chromatographed (0-2% 2.3M NH₃ in MeOH/CH₂Cl₂) to produce 0.042 g of 79 as a clear oil.

Step 6: Compound 79 was converted into the title compound using a procedure analogous to Step 4 of Example 1. MS: (M+1) 478.

Using the procedures described above, the following compounds were prepared:

| Ex. No. | Structure | MS (M + H) |
|---|---|---|
| 39 | 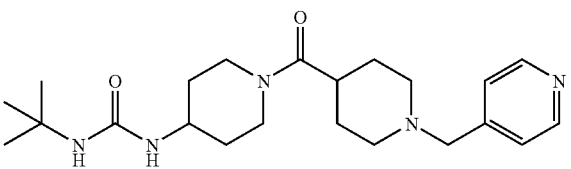 | 402 |
| 40 | 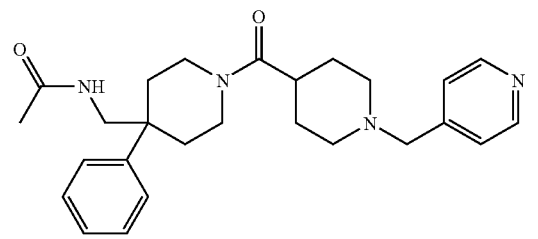 | 435 |
| 41 | 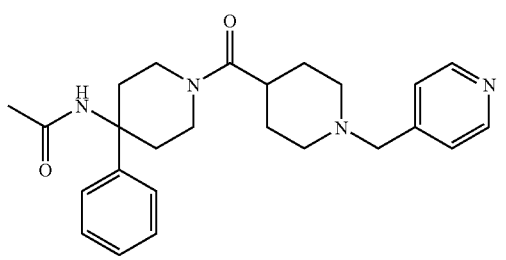 | 421 |
| 42 | 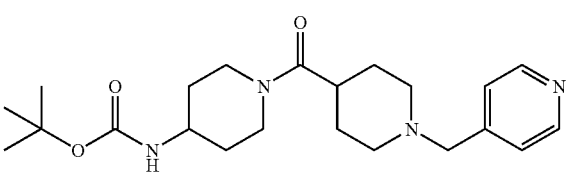 | 403 |
| 43 | 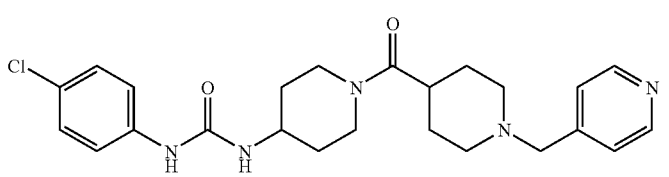 | 456 |
| 44 | 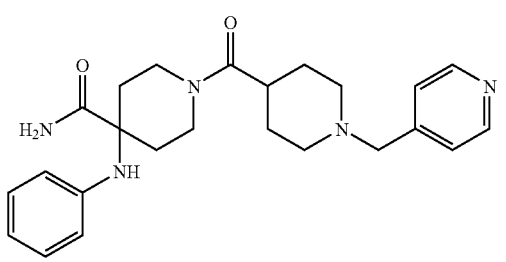 | 422 |
| 45 | 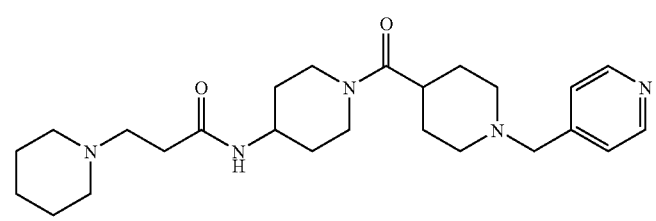 | 442 |

-continued
| Ex. No. | Structure | MS (M + H) |
|---|---|---|
| 46 | 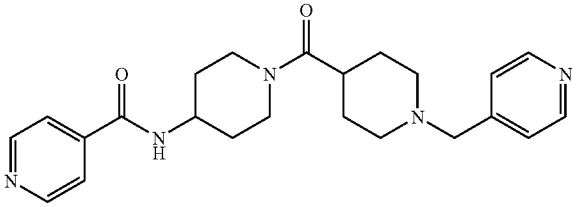 | 408 |
| 47 | 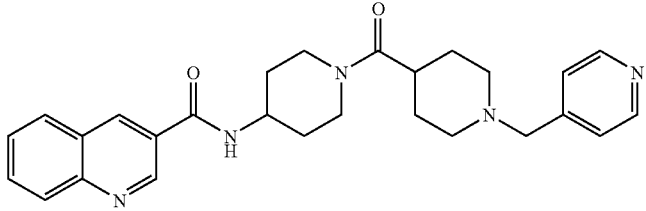 | 458 |
| 48 | 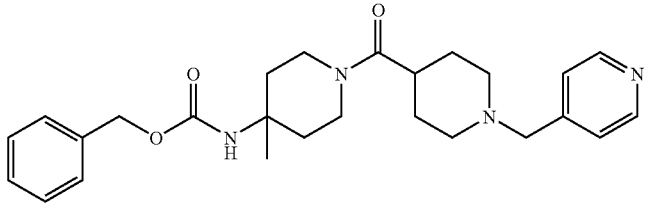 | 451 |
| 49 | 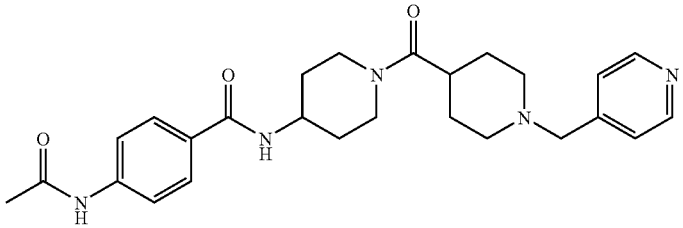 | 464 |
| 50 | 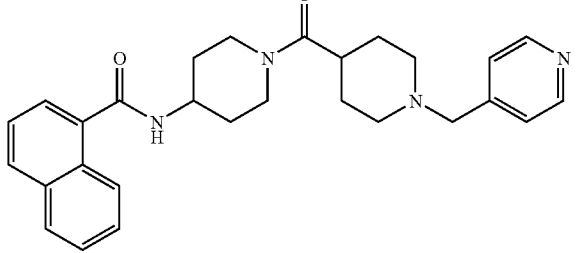 | 457 |
| 51 | 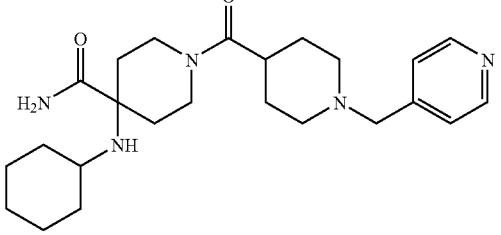 | 428 |

-continued

| Ex. No. | Structure | MS (M + H) |
|---|---|---|
| 52 | 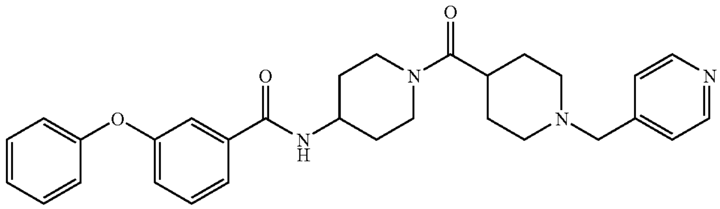 | 501 |
| 53 | 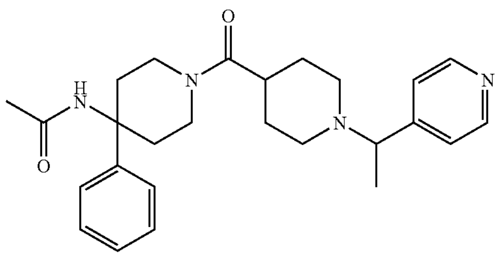 | 435 |
| 54 | 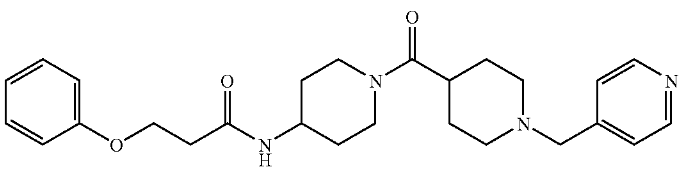 | 451 |
| 55 | 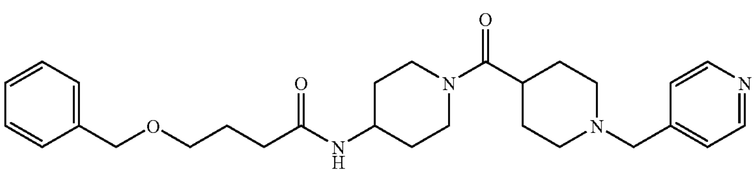 | 479 |
| 56 | 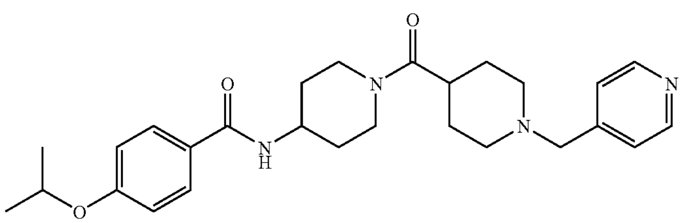 | 465 |
| 57 | 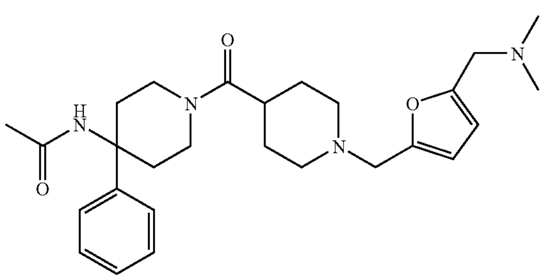 | 467 |
| 58 | 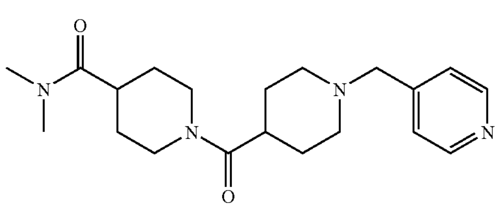 | 359 |

-continued
| Ex. No. | Structure | MS (M + H) |
|---|---|---|
| 59 | 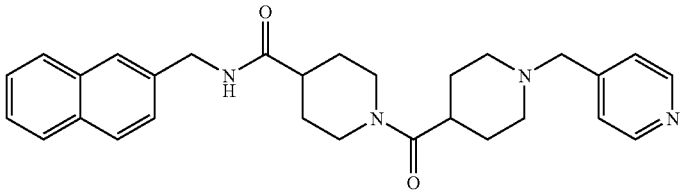 | 471 |
| 60 | 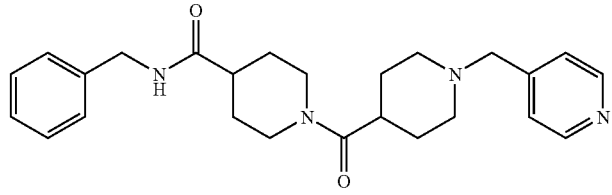 | 421 |
| 61 | 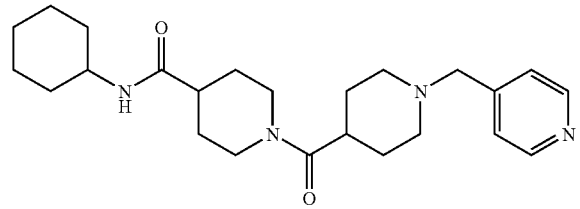 | 413 |
| 62 | 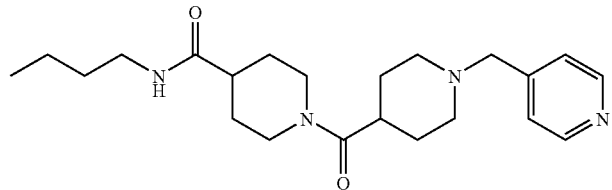 | 387 |
| 63 | 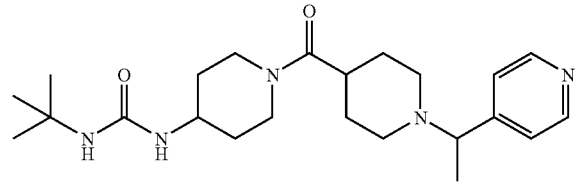 | 416 |
| 64 | 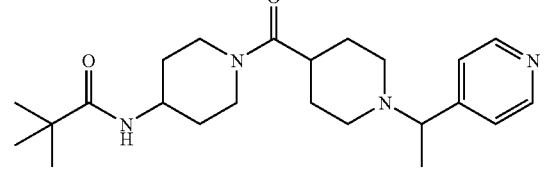 | 401 |
| 65 | 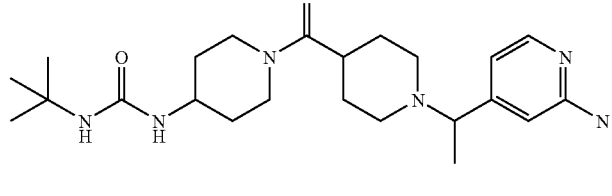 | 431 |

-continued
| Ex. No. | Structure | MS (M + H) |
|---|---|---|
| 66 | 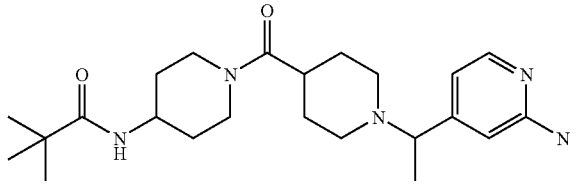 | 416 |
| 67 | 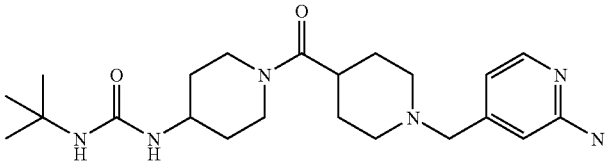 | 417 |
| 68 | 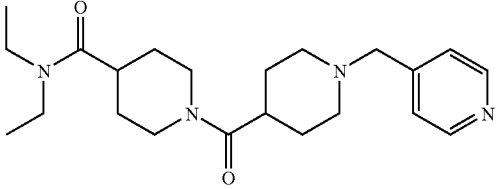 | 387 |
| 69 | 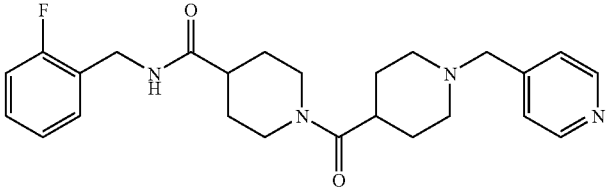 | 439 |
| 70 | 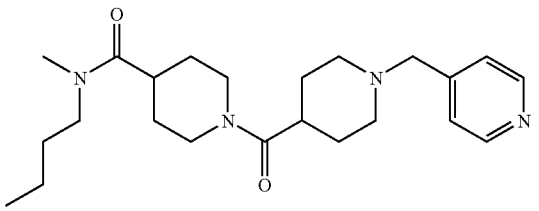 | 401 |
| 71 | 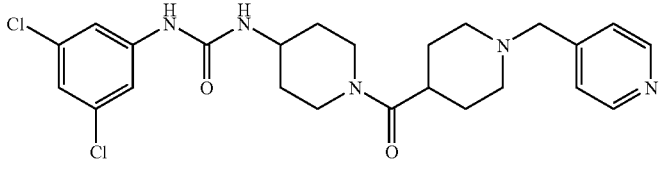 | 490 |
| 72 | 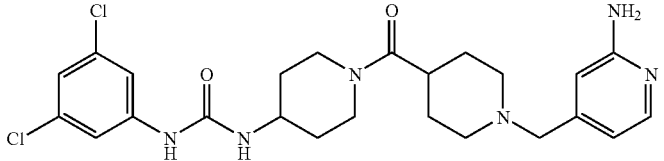 | 505 |

-continued

| Ex. No. | Structure | MS (M + H) |
|---|---|---|
| 73 | 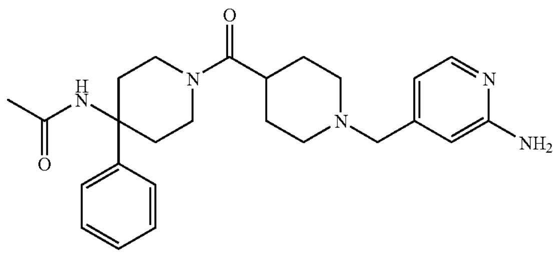 | 434 |
| 74 | 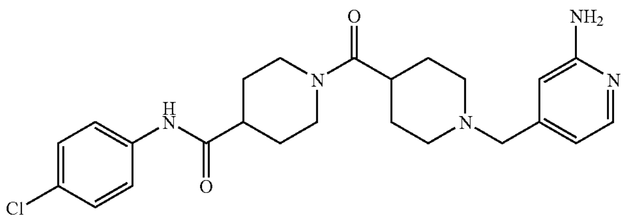 | 456 |
| 75 | 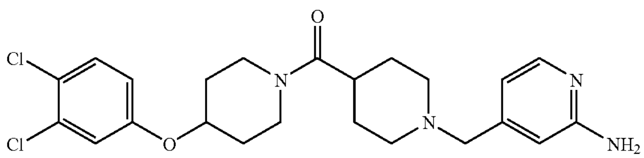 | 463 |
| 76 | 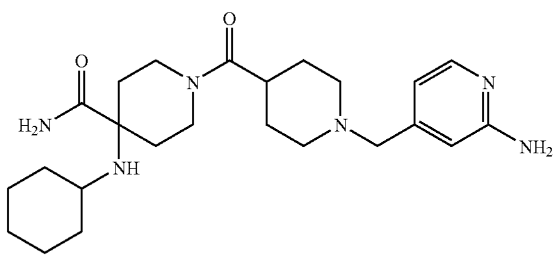 | 443 |
| 77 | 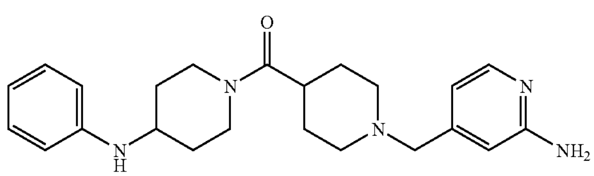 | 394 |
| 78 | 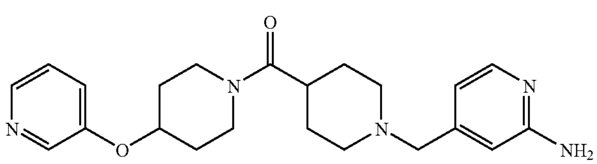 | 396 |
| 79 | 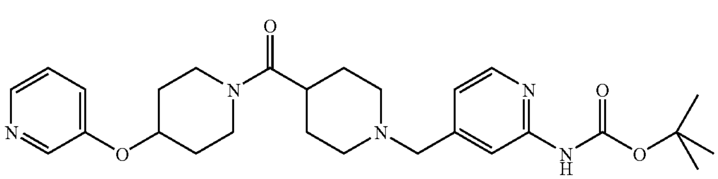 | 496 |

| Ex. No. | Structure | MS (M + H) |
|---|---|---|
| 80 | 2,4,6-trifluorophenoxy-piperidine-carbonyl-piperidine-CH2-(2-aminopyridin-4-yl) | 449 |
| 81 | pyridin-2-yloxy-piperidine-carbonyl-piperidine-CH2-(2-aminopyridin-4-yl) | 396 |
| 82 | 2-fluorophenyl-NH-C(O)-piperidine-carbonyl-piperidine-CH2-(pyridin-4-yl) | 425 |
| 83 | pyrimidin-2-yloxy-piperidine-carbonyl-piperidine-CH2-(2-aminopyridin-4-yl) | 397 |
| 84 | acetamido-phenyl-piperidine-carbonyl-piperidine-CH2-(2-Boc-aminopyridin-4-yl) | 536 |
| 85 | 6-chloropyrazin-2-yloxy-piperidine-carbonyl-piperidine-CH2-(pyridin-4-yl) | 416 |
| 86 | pyrazin-2-yloxy-piperidine-carbonyl-piperidine-CH2-(2-aminopyridin-4-yl) | 431 |
| 87 | pyridin-2-ylamino-piperidine-C(O)-piperidine-CH2-(2-aminopyridin-4-yl) | 397 |

-continued
| Ex. No. | Structure | MS (M + H) |
|---|---|---|
| 88 | 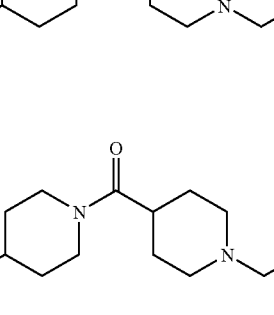 | 423 |
| 89 | 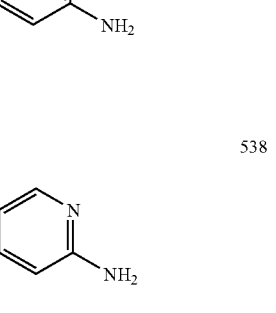 | 538 |
| 90 | 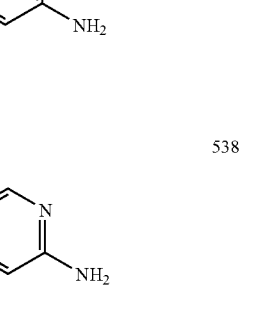 | 395 |
| 91 | 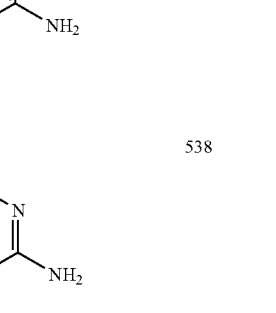 | 476 |
| 92 | 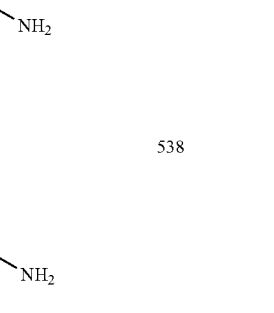 | 469 |
| 93 | 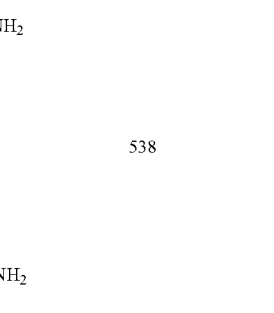 | 346 |

-continued
| Ex. No. | Structure | MS (M + H) |
|---|---|---|
| 94 | 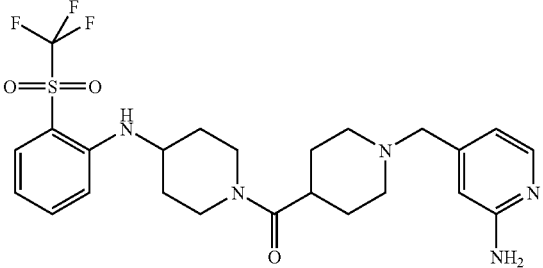 | 526 |
| 95 | 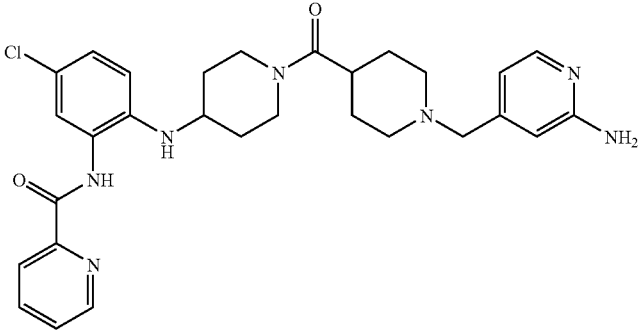 | 548 |
| 96 | 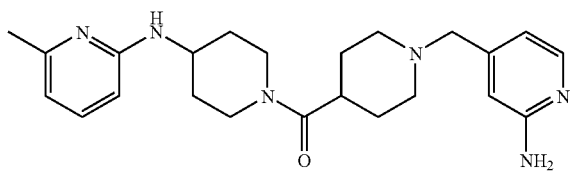 | 503 |
| 97 | 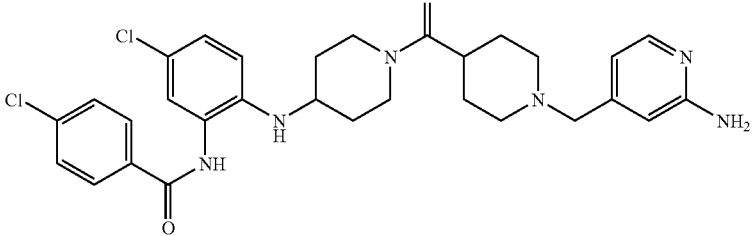 | 581 |
| 98 | 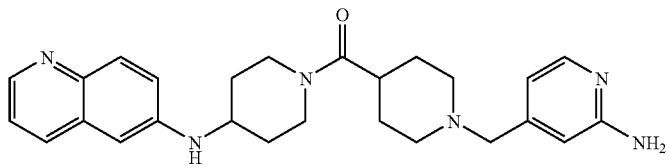 | 445 |
| 99 | 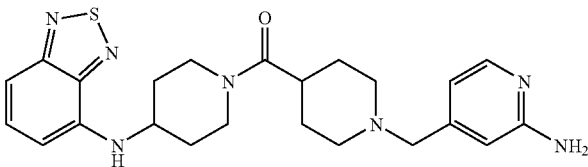 | 452 |

-continued

| Ex. No. | Structure | MS (M + H) |
|---|---|---|
| 100 | 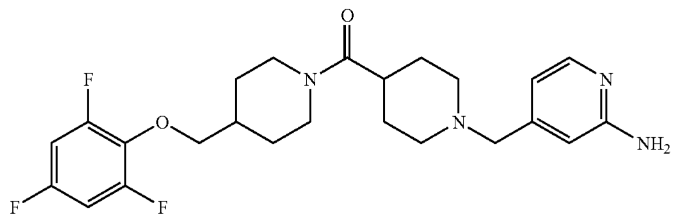 | 463 |
| 101 | 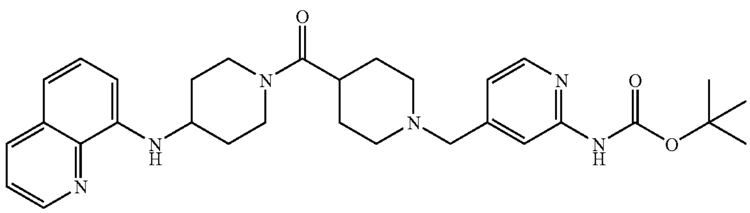 | 545 |
| 102 | 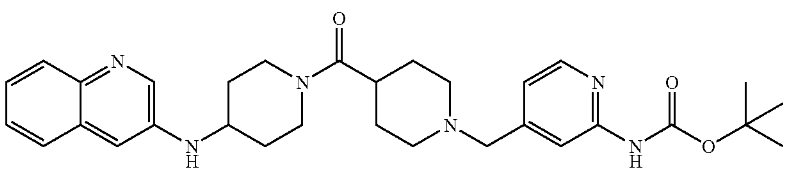 | 545 |
| 103 | 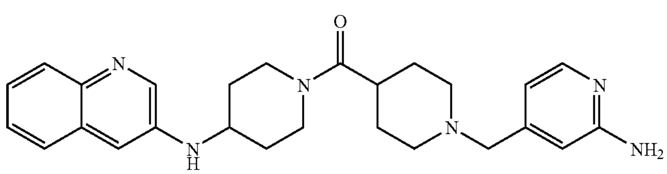 | 445 |
| 104 | 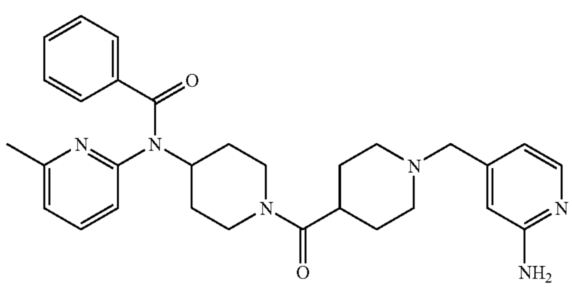 | 513 |
| 105 | 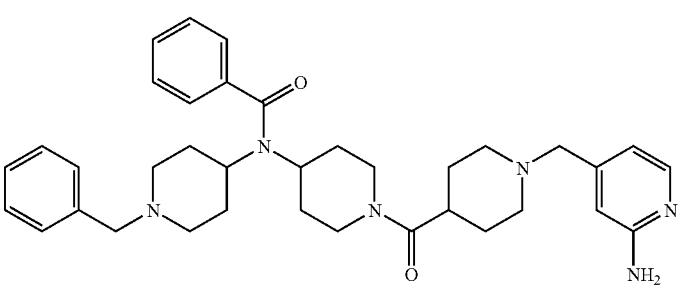 | 595 |

-continued

| Ex. No. | Structure | MS (M + H) |
|---|---|---|
| 106 | 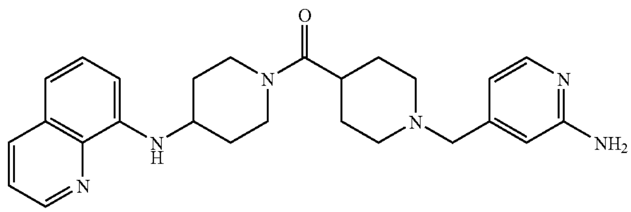 | 445 |
| 107 | 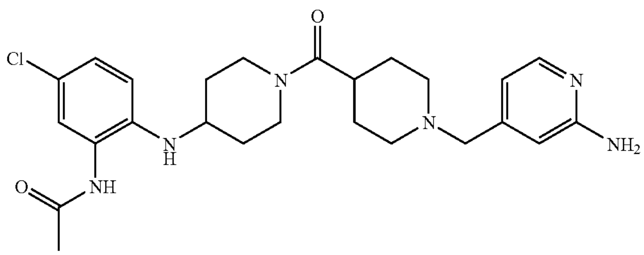 | 485 |
| 108 | 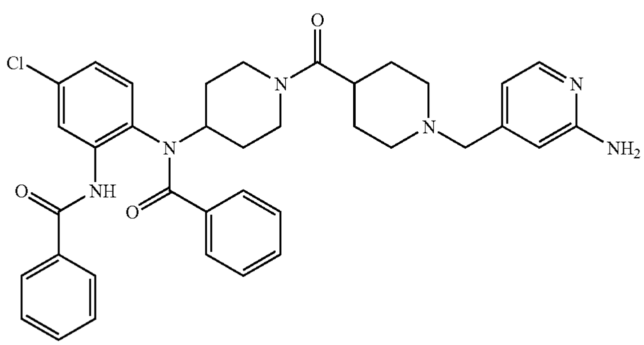 | 547 |
| 109 | 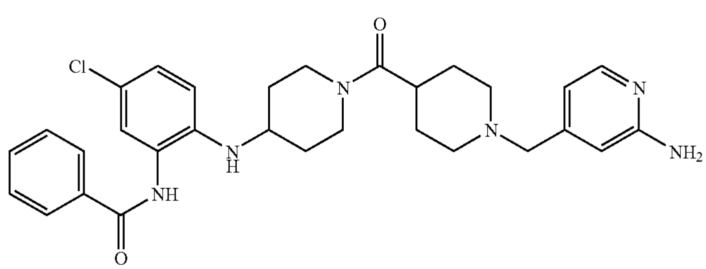 | 651 |
| 110 | 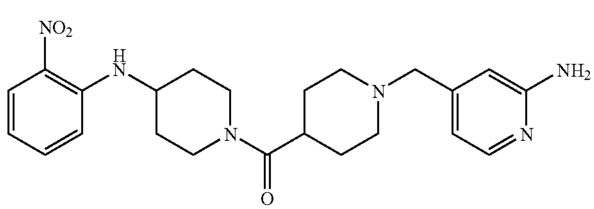 | 439 |

-continued

| Ex. No. | Structure | MS (M + H) |
|---|---|---|
| 111 | 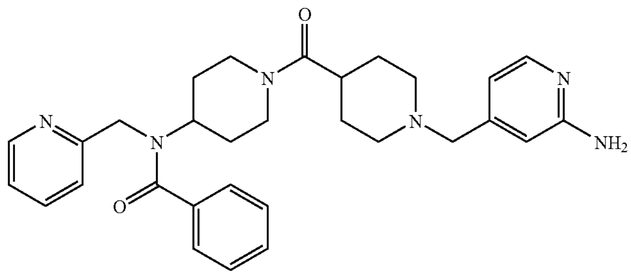 | 513 |
| 112 | 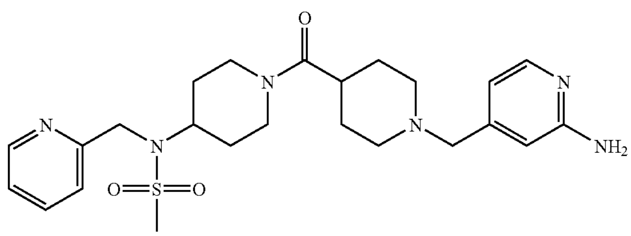 | 487 |
| 113 | 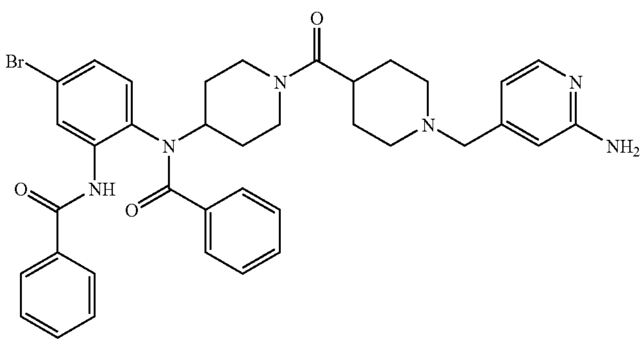 | 697 |
| 114 | 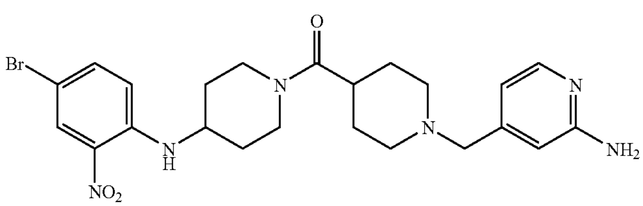 | 519 |
| 115 | 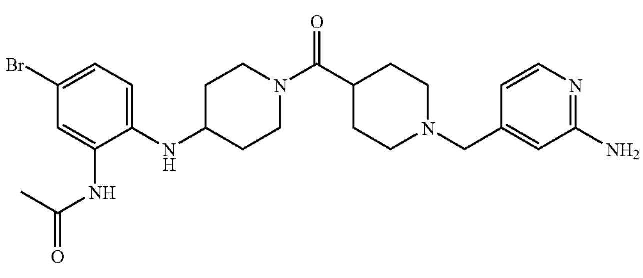 | 531 |
| 116 | 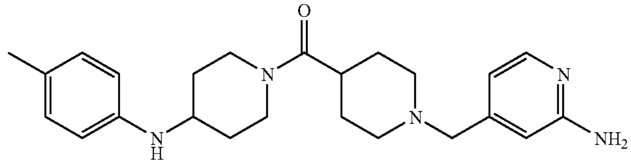 | 408 |

| Ex. No. | Structure | MS (M + H) |
|---|---|---|
| 117 | 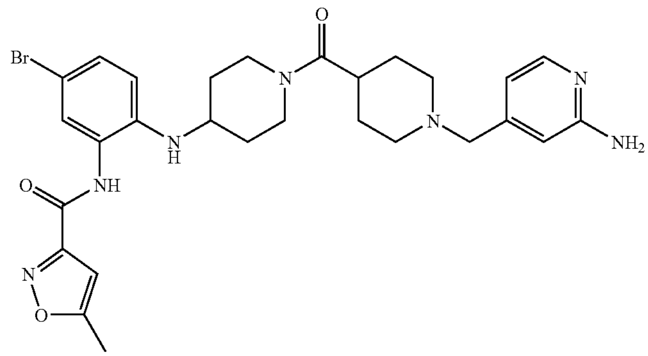 | 598 |
| 118 | 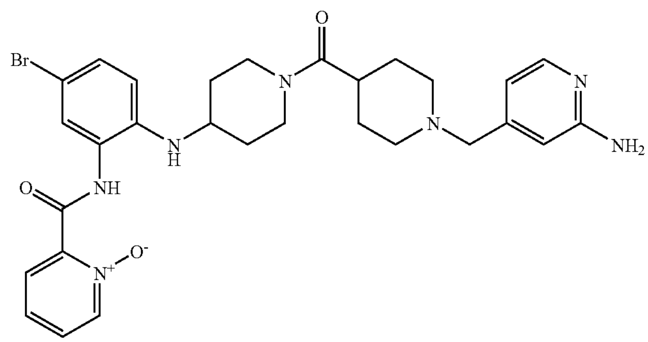 | 608 |
| 119 | 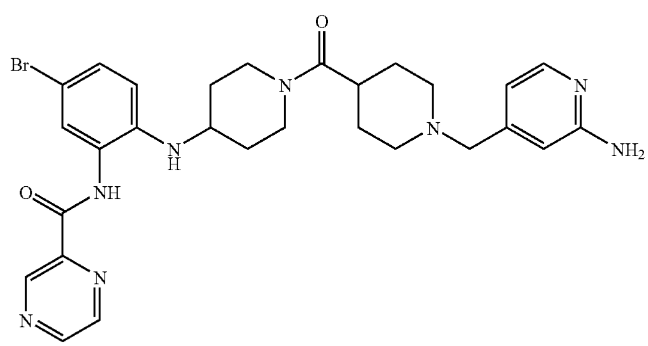 | 595 |
| 120 | 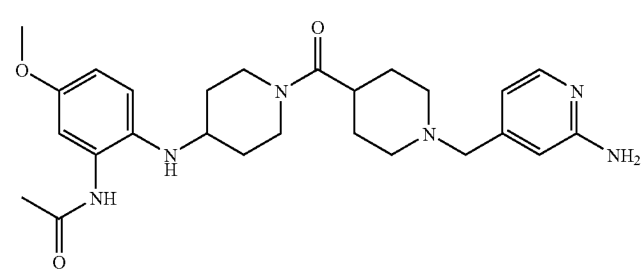 | 481 |

-continued
| Ex. No. | Structure | MS (M + H) |
|---|---|---|
| 121 | 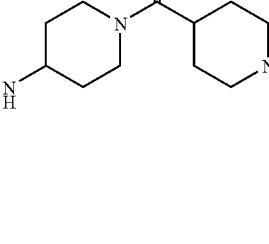 | 548 |
| 122 | 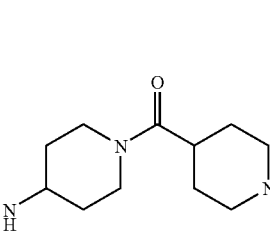 | 629 |
| 123 | 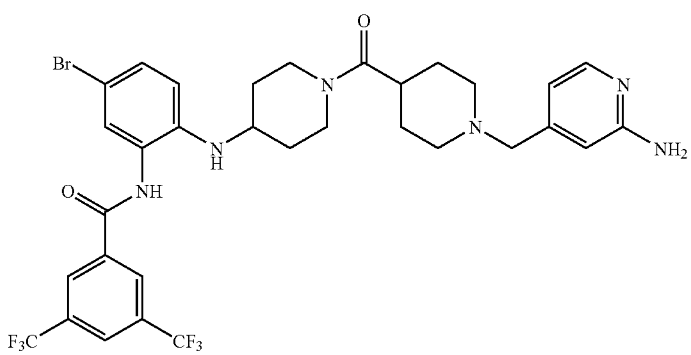 | 729 |
| 124 | 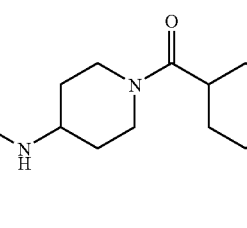 | 536 |

| Ex. No. | Structure | MS (M + H) |
|---|---|---|
| 125 | 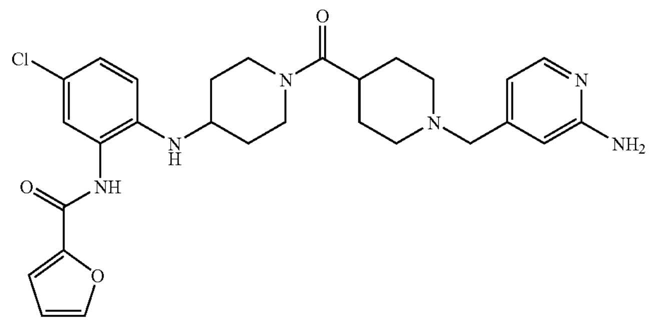 | 537 |
| 126 | 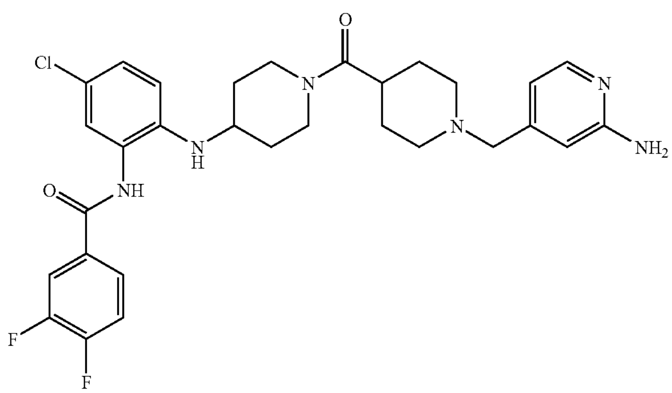 | 583 |
| 127 | 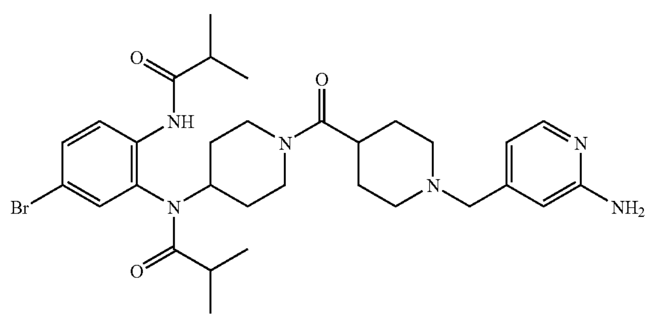 | 557 |
| 128 | 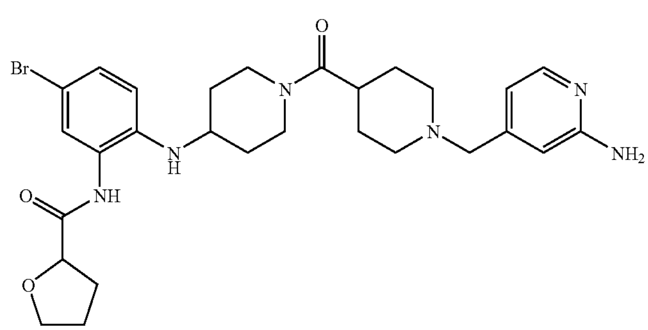 | 585 |

| Ex. No. | Structure | MS (M + H) |
|---|---|---|
| 129 | 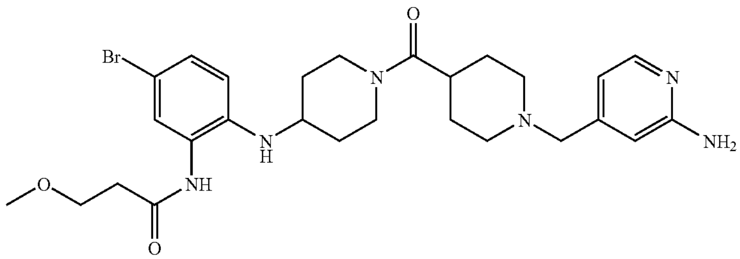 | 575 |
| 130 | 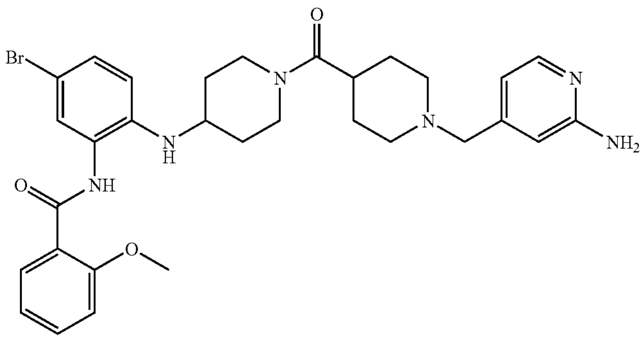 | 623 |
| 131 | 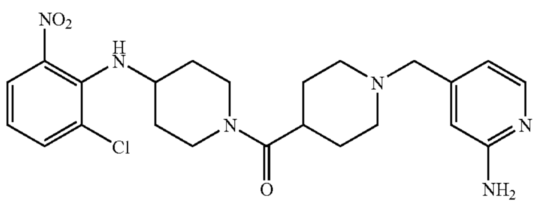 | 473 |
| 132 | 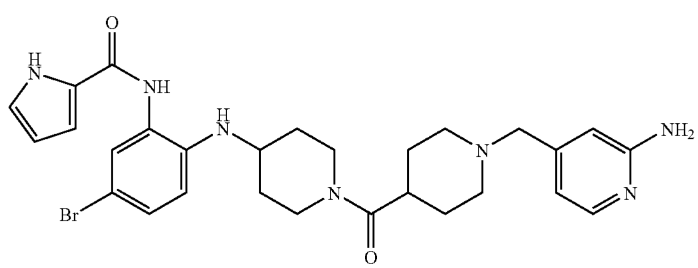 | 582 |
| 133 | 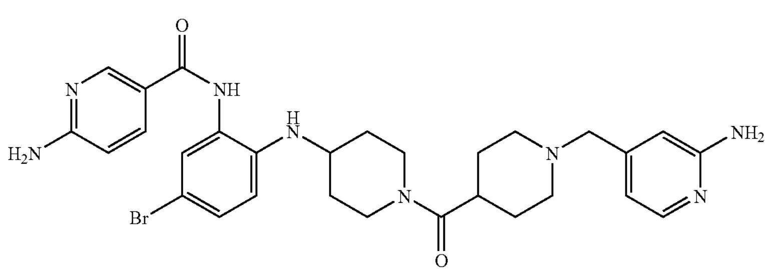 | 607 |

-continued
| Ex. No. | Structure | MS (M + H) |
|---|---|---|
| 134 | 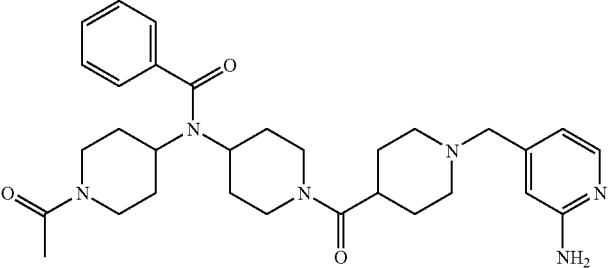 | 547 |
| 135 | 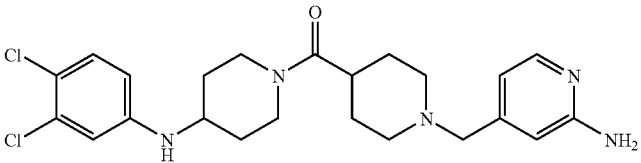 | 463 |
| 136 | 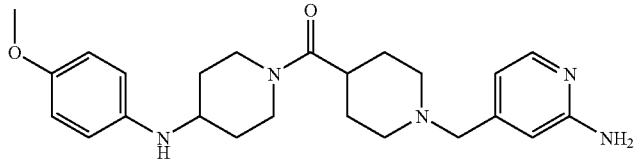 | 424 |
| 137 | 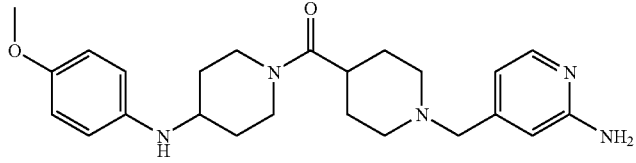 | 428 |
| 138 | 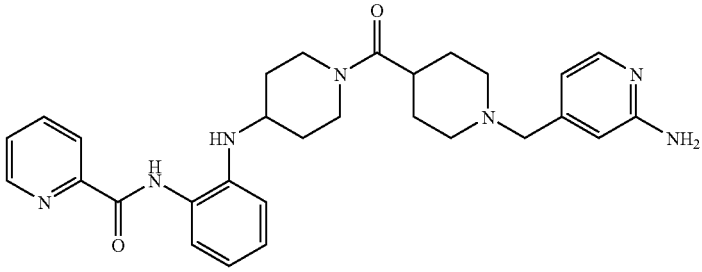 | 514 |
| 139 | 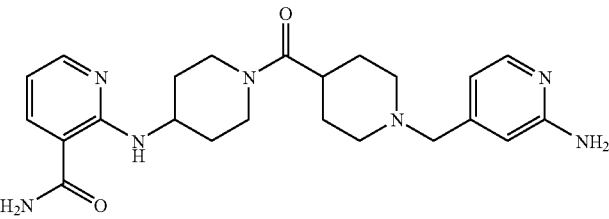 | 438 |
| 140 | 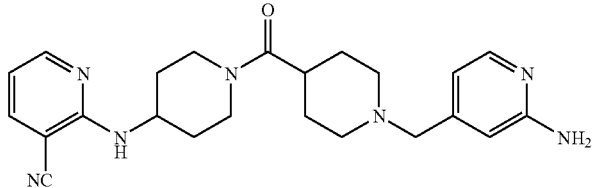 | 420 |

| Ex. No. | Structure | MS (M + H) |
|---|---|---|
| 141 | 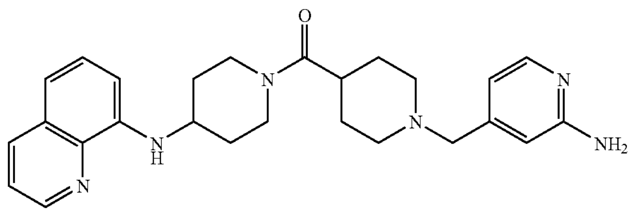 | 445 |
| 142 | 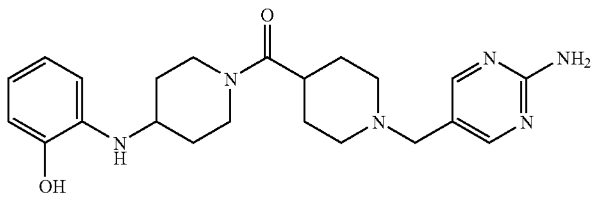 | 411 |
| 143 | 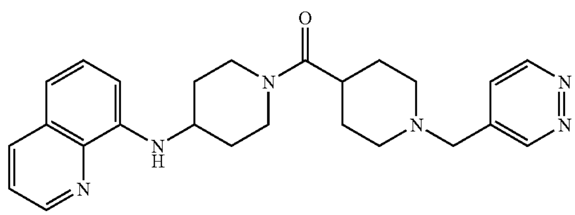 | 431 |
| 144 | 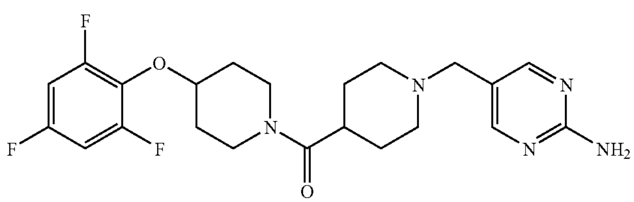 | 450 |
| 145 | 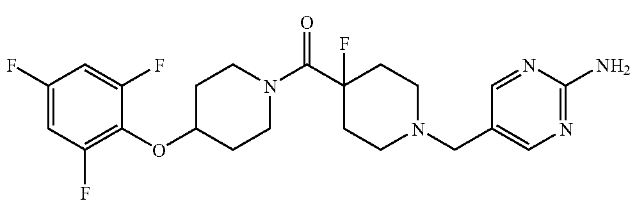 | 468 |
| 146 | 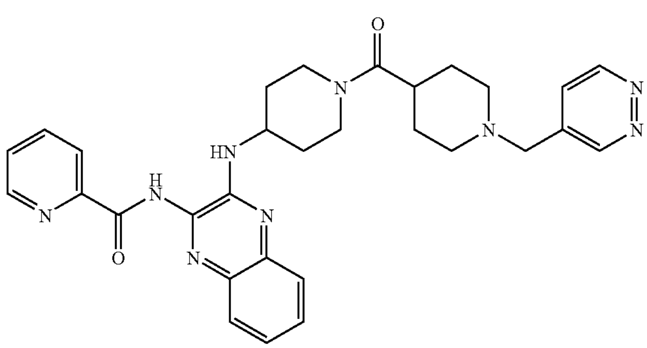 | 552 |

-continued

| Ex. No. | Structure | MS (M + H) |
|---|---|---|
| 147 | 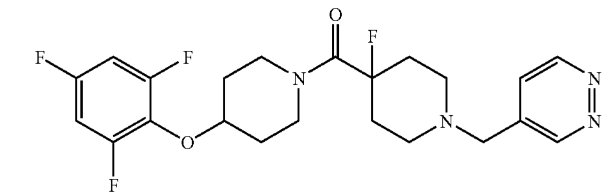 | 453 |
| 148 | 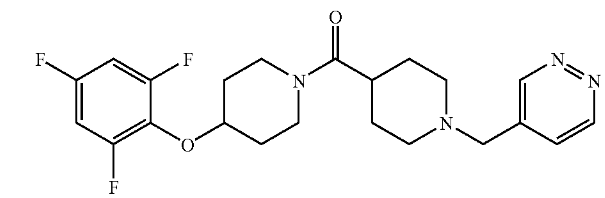 | 435 |
| 149 | 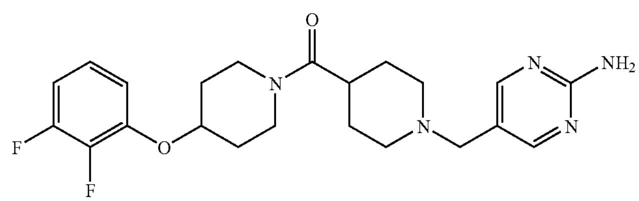 | 432 |
| 150 | 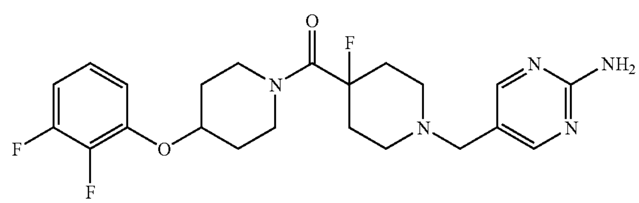 | 450 |
| 151 | 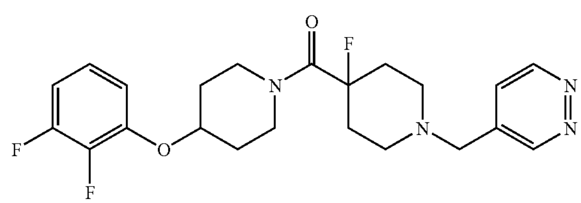 | 435 |
| 152 | 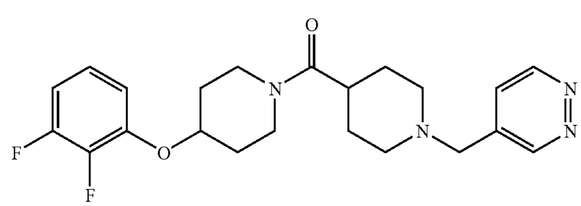 | 417 |
| 153 | 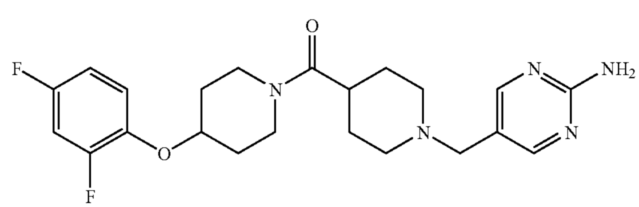 | 432 |

-continued

| Ex. No. | Structure | MS (M + H) |
|---|---|---|
| 154 | 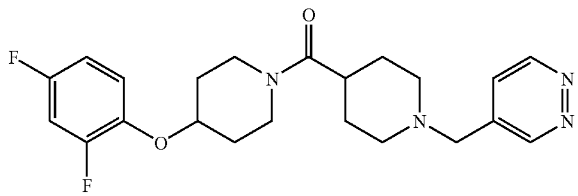 | 417 |
| 155 | 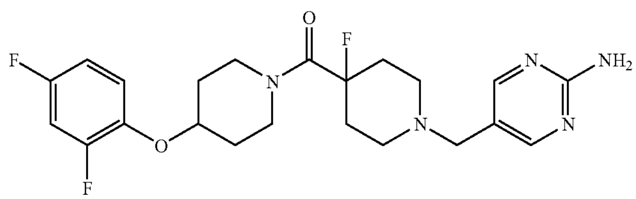 | 450 |
| 156 | 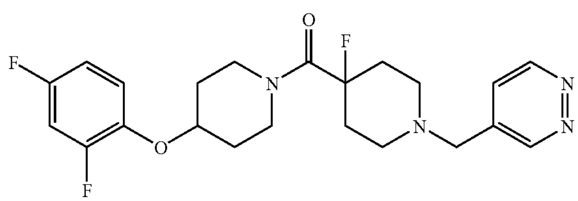 | 435 |
| 157 | 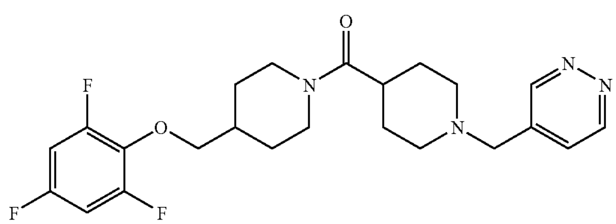 | 449 |
| 158 | 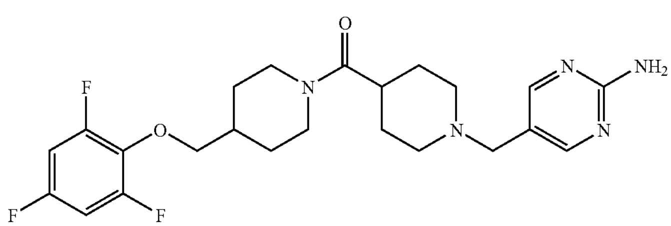 | 464 |
| 159 | 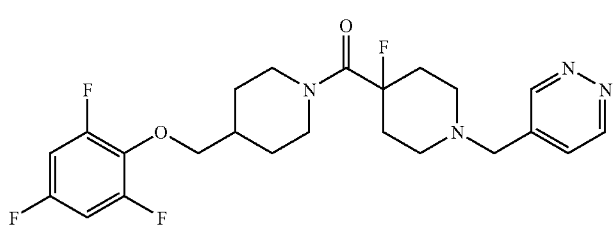 | 467 |
| 160 | 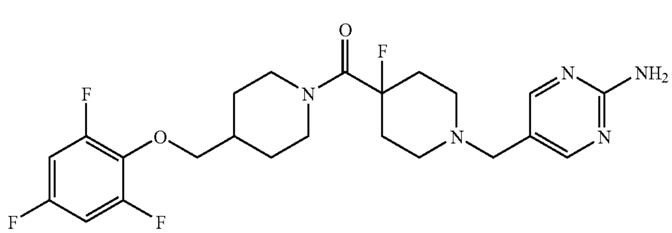 | 482 |

-continued

| Ex. No. | Structure | MS (M + H) |
|---|---|---|
| 161 | 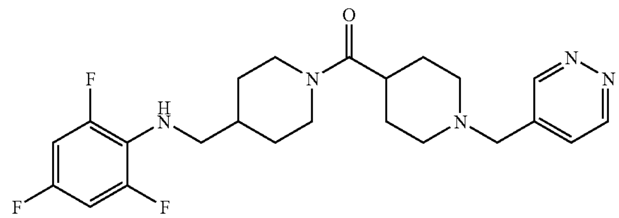 | 448 |
| 162 | 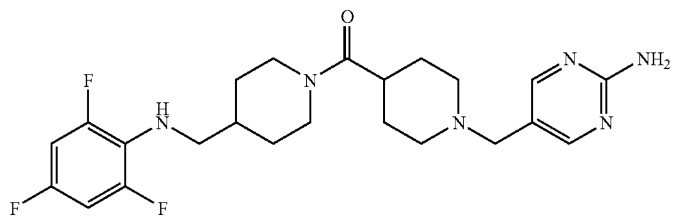 | 463 |
| 163 | 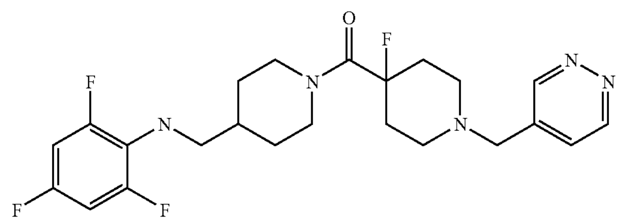 | 466 |
| 164 | 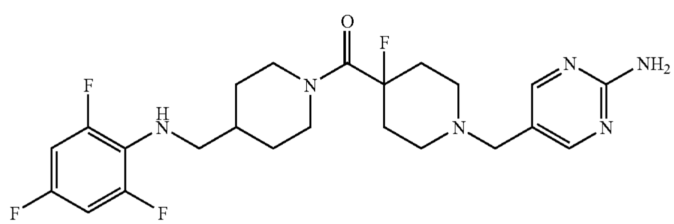 | 481 |
| 165 | 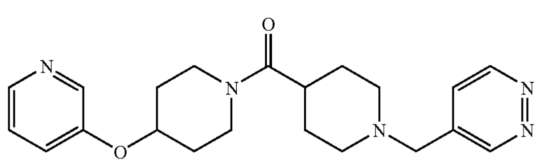 | 382 |
| 166 | 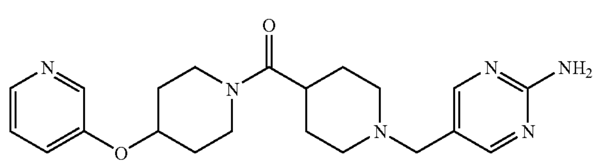 | 397 |
| 167 | 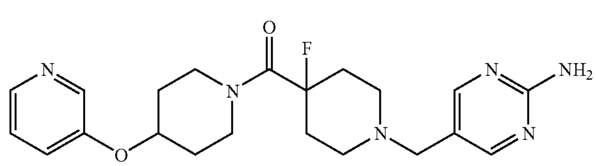 | 415 |
| 168 | 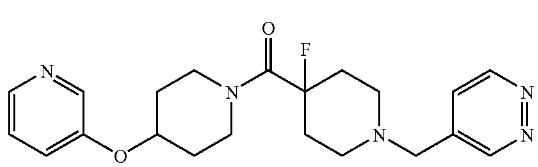 | 400 |

-continued
| Ex. No. | Structure | MS (M + H) |
|---|---|---|
| 169 | 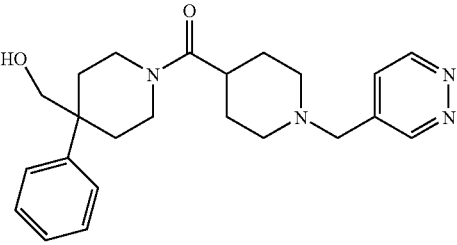 | 395 |
| 170 | 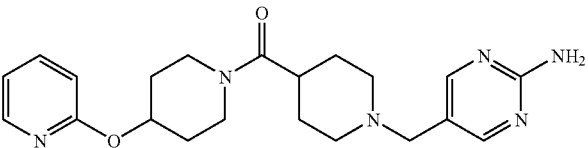 | 397 |
| 172 | 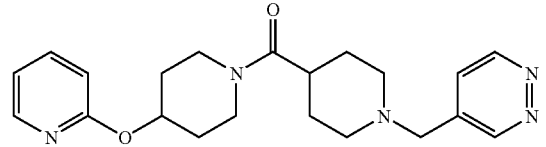 | 382 |
| 173 | 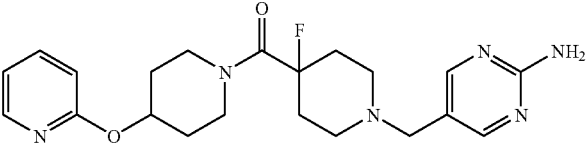 | 415 |
| 174 | 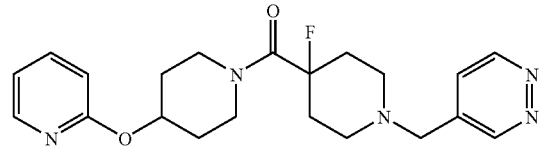 | 400 |
| 175 | 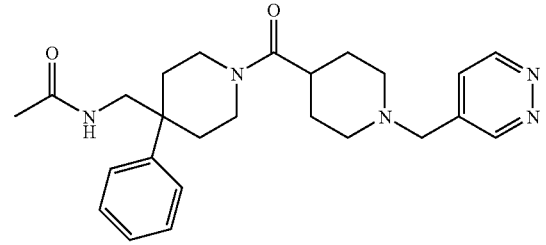 | 436 |
| 176 | 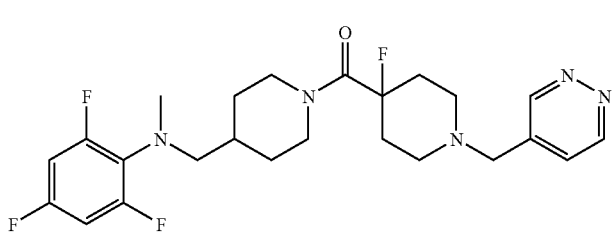 | 480 |

-continued

| Ex. No. | Structure | MS (M + H) |
|---|---|---|
| 177 | 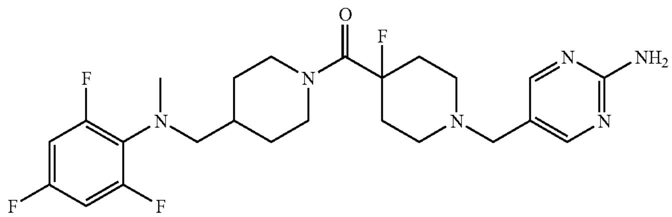 | 495 |
| 178 | 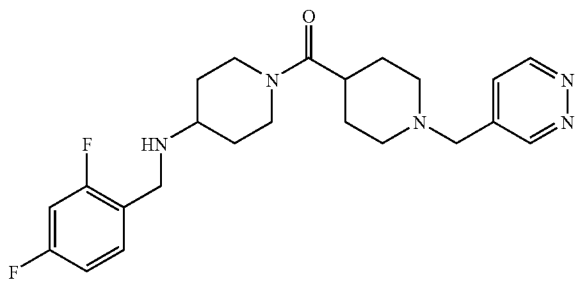 | 430 |
| 179 | 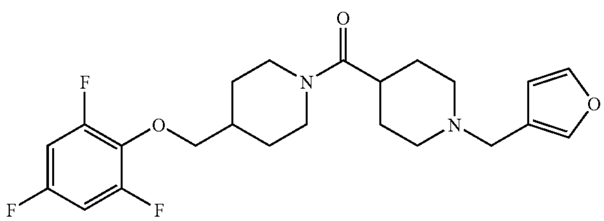 | 437 |
| 180 | 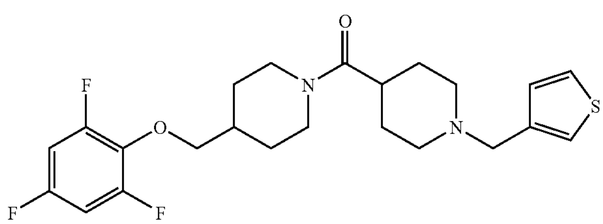 | 453 |
| 181 | 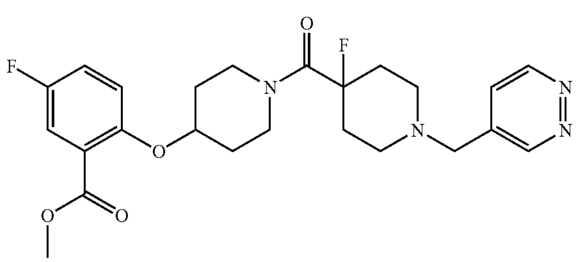 | 475 |
| 182 | 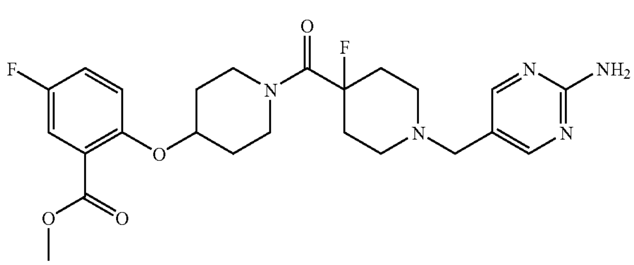 | 490 |

-continued
| Ex. No. | Structure | MS (M + H) |
|---|---|---|
| 183 | 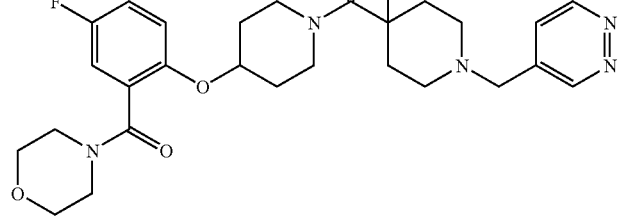 | 530 |
| 184 | 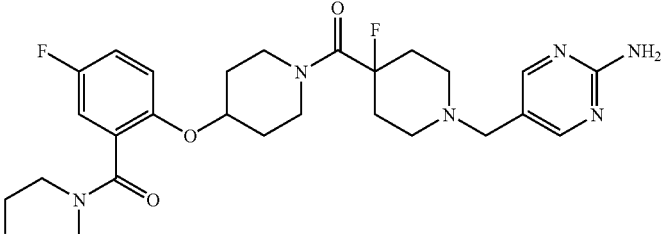 | 545 |
| 185 | 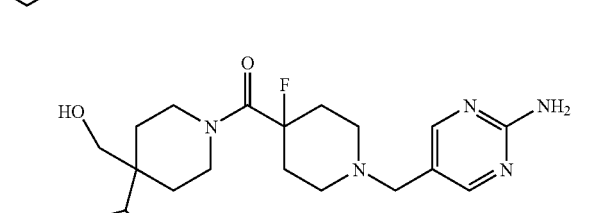 | 428 |
| 186 | 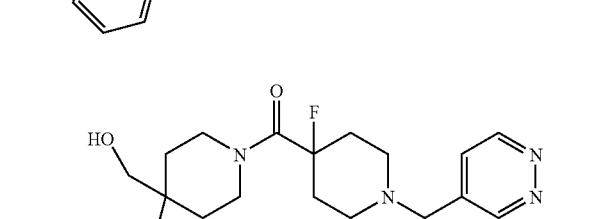 | 413 |
| 187 | 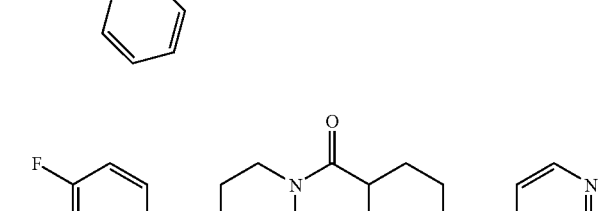 | 457 |

-continued
| Ex. No. | Structure | MS (M + H) |
|---|---|---|
| 188 | 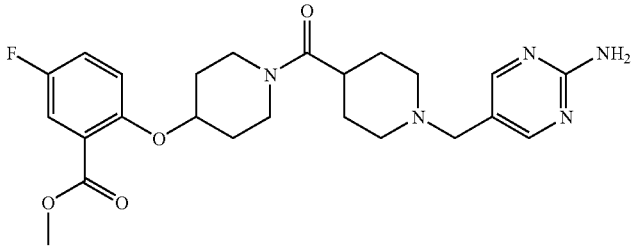 | 472 |
| 189 | 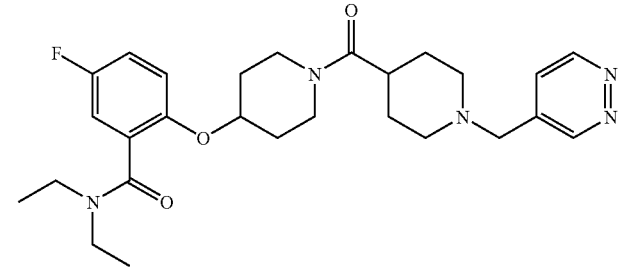 | 498 |
| 190 | 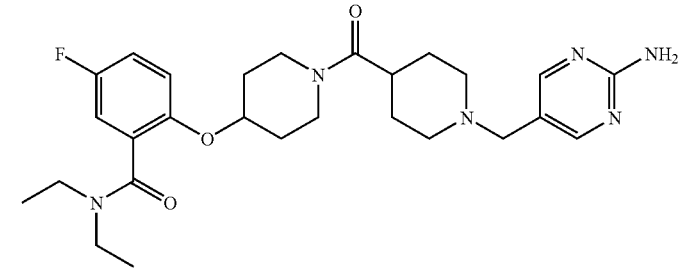 | 513 |
| 191 | 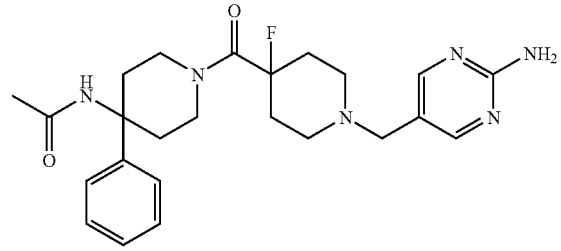 | 455 |
| 192 | 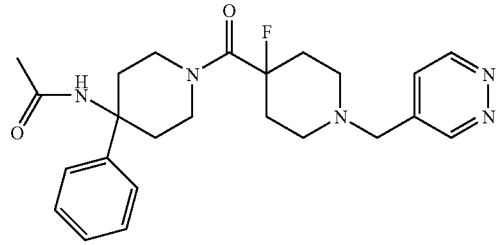 | 430 |
| 193 | 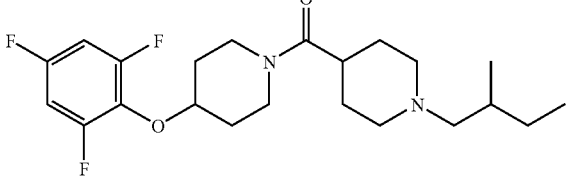 | 413 |

| Ex. No. | Structure | MS (M + H) |
|---|---|---|
| 194 | 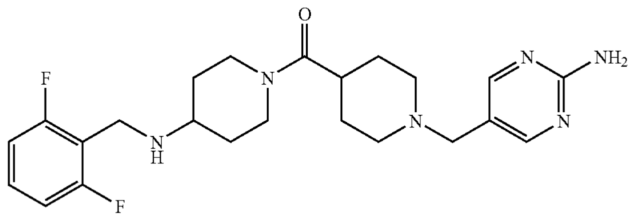 | 445 |
| 195 | 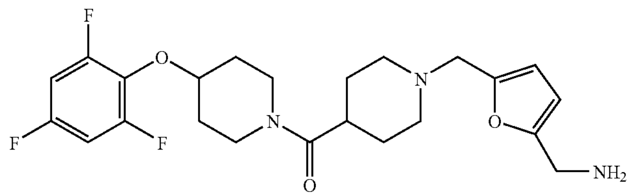 | 452 |
| 196 | 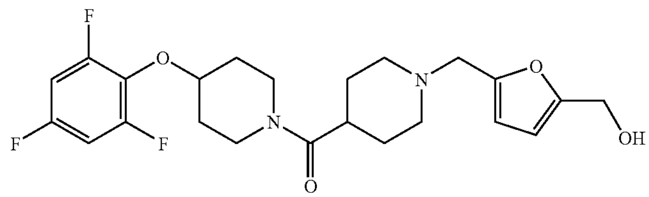 | 453 |
| 197 | 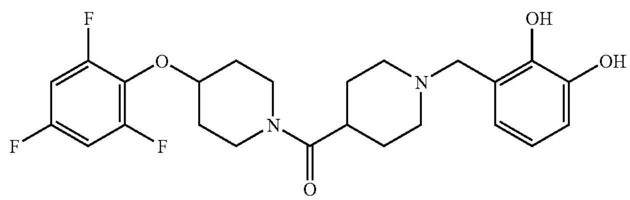 | 465 |
| 198 | 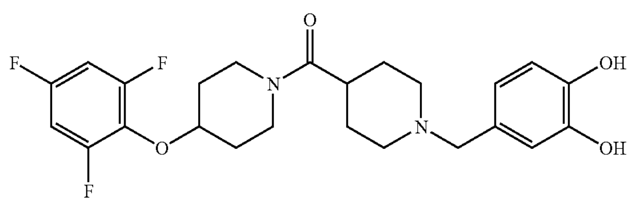 | 465 |
| 199 | 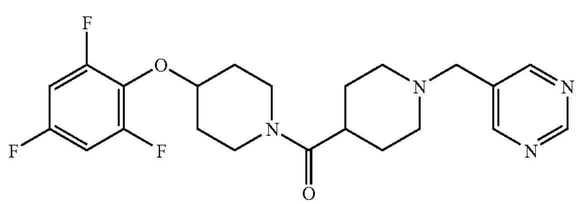 | 435 |
| 200 | 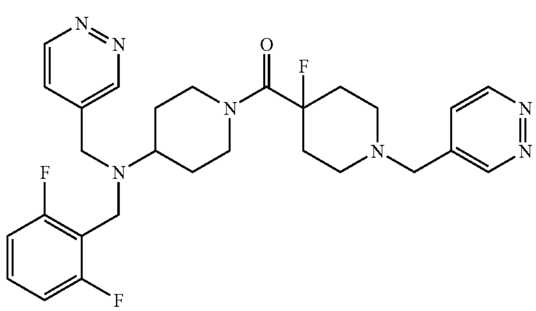 | 540 |

-continued
| Ex. No. | Structure | MS (M + H) |
|---|---|---|
| 201 | 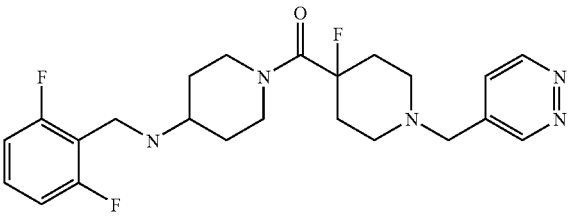 | 448 |
| 202 | 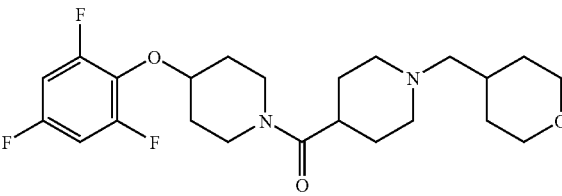 | 441 |
| 203 | 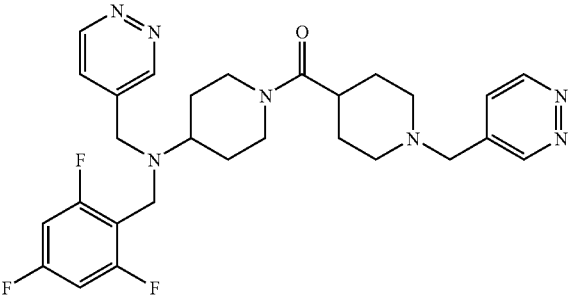 | 540 |
| 204 | 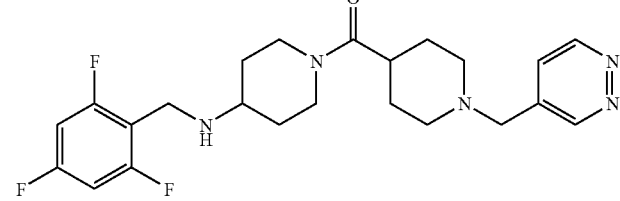 | 448 |
| 205 | 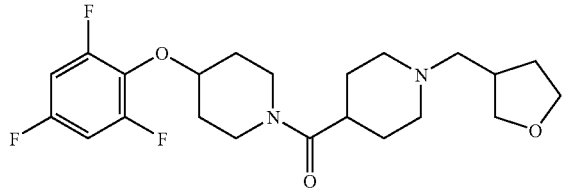 | 427 |
| 206 | 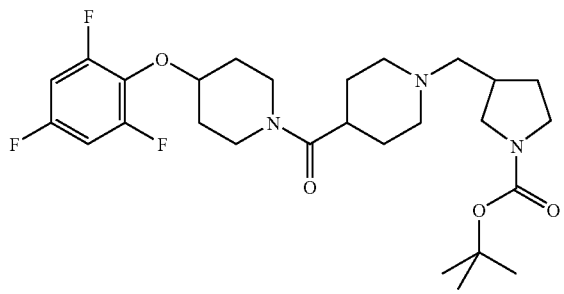 | 526 |

-continued

| Ex. No. | Structure | MS (M + H) |
|---|---|---|
| 207 | 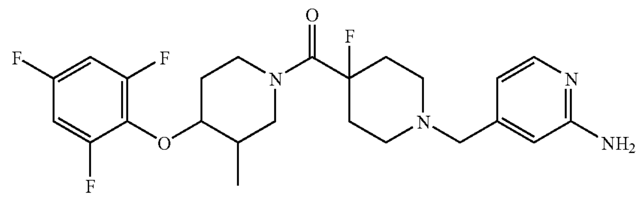 | 481 |
| 208 | 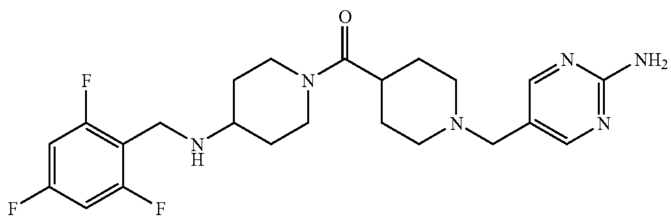 | 463 |
| 209 | 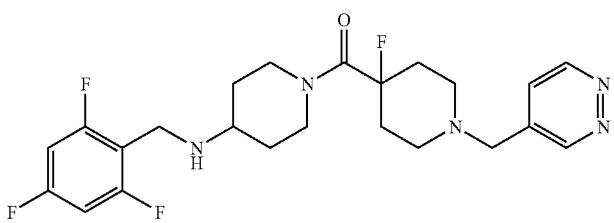 | 466 |
| 210 | 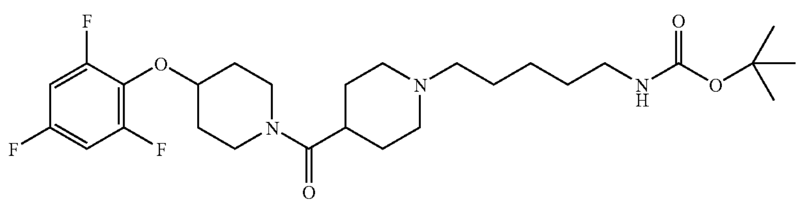 | 528 |
| 211 | 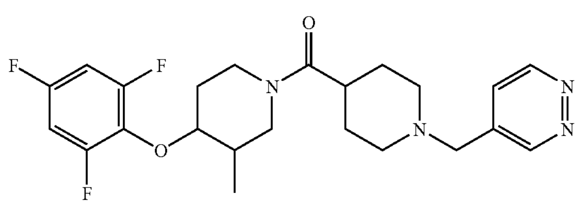 | 449 |
| 212 | 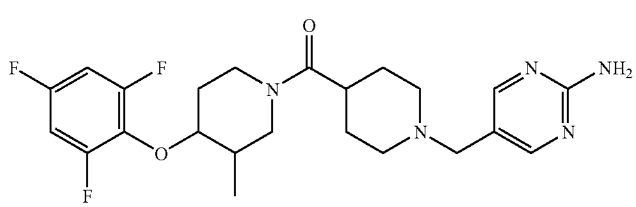 | 464 |
| 213 | 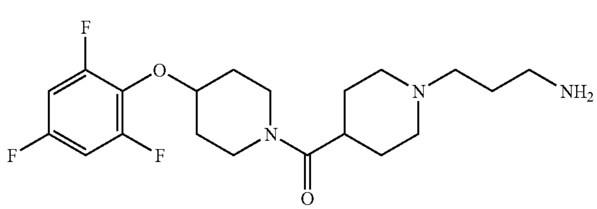 | 400 |

-continued

| Ex. No. | Structure | MS (M + H) |
|---|---|---|
| 214 | 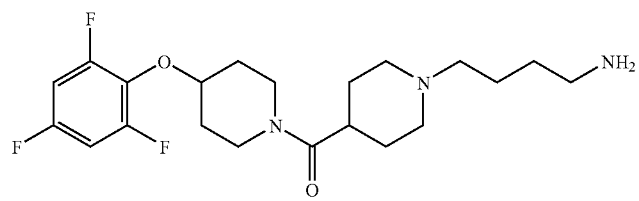 | 414 |
| 215 | 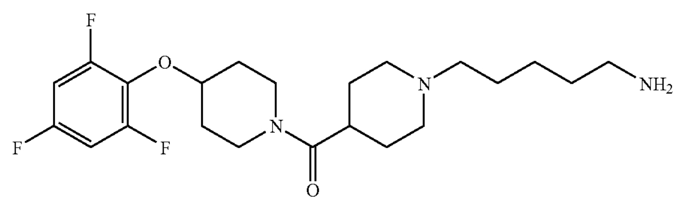 | 428 |
| 216 | 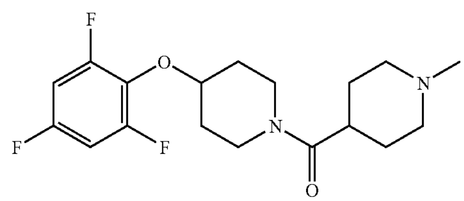 | 357 |
| 217 | 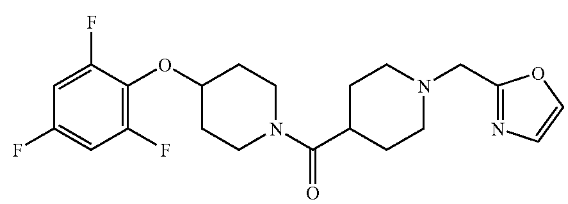 | 424 |
| 218 | 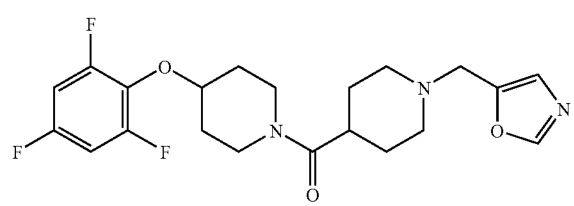 | 424 |
| 219 | 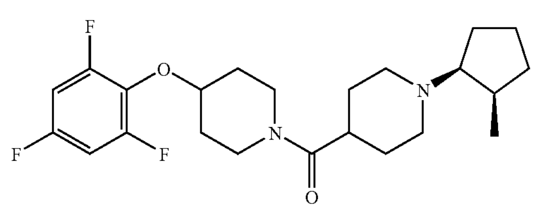 | 425 |
| 220 | 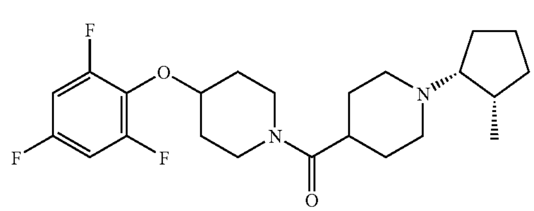 | 425 |

-continued
| Ex. No. | Structure | MS (M + H) |
|---|---|---|
| 221 | 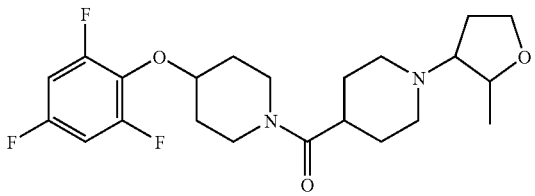 | 427 |
| 222 | 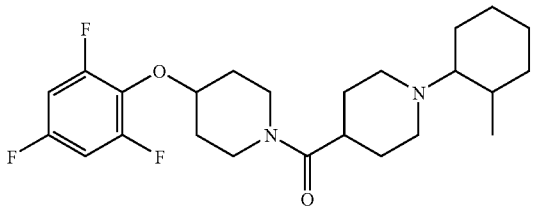 | 439 |
| 223 | 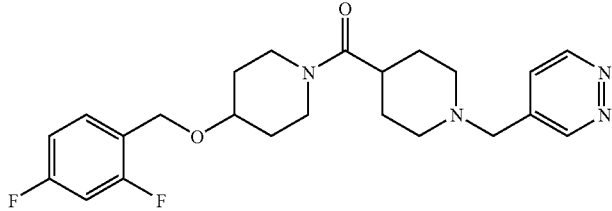 | 431 |
| 224 | 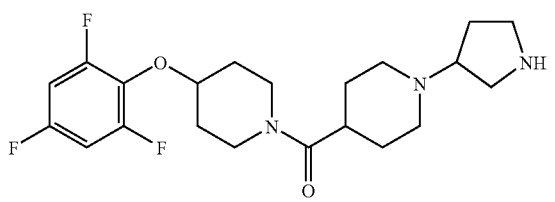 | 412 |
| 225 | 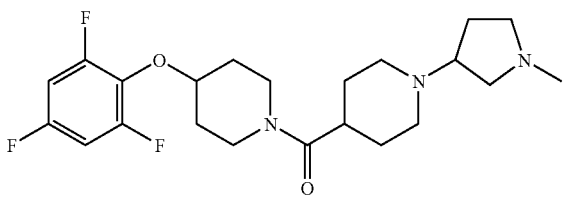 | 426 |
| 226 | 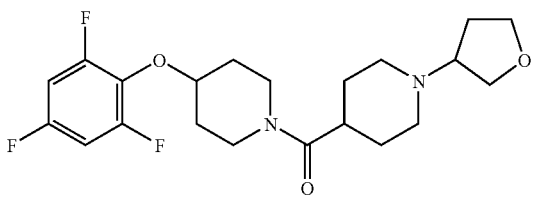 | 413 |
| 227 | 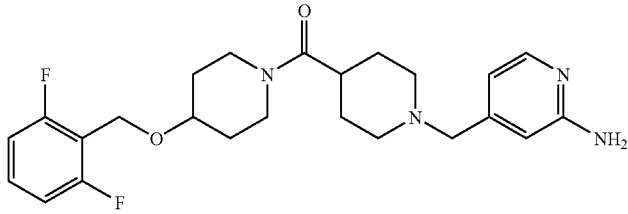 | 445 |

| Ex. No. | Structure | MS (M + H) |
|---|---|---|
| 228 | 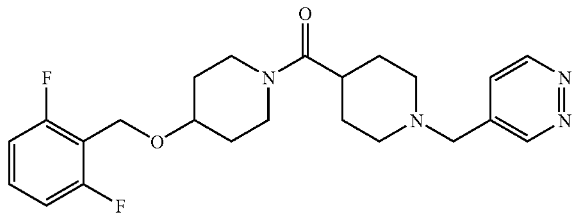 | 431 |
| 229 | 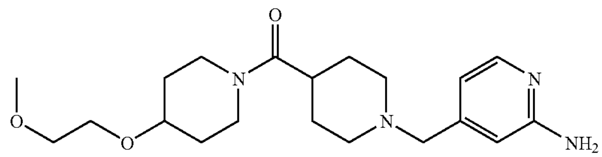 | 377 |
| 230 | 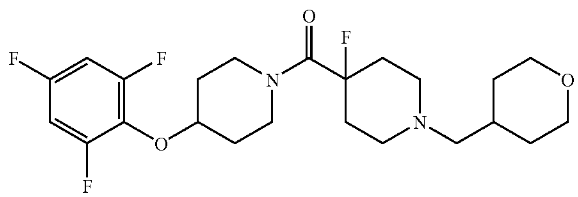 | 459 |
| 231 | 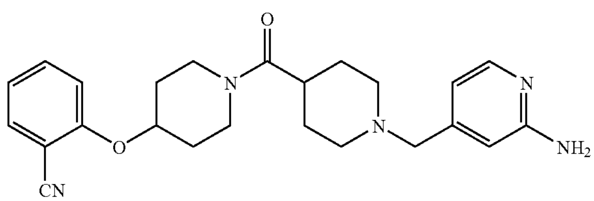 | 420 |
| 232 | 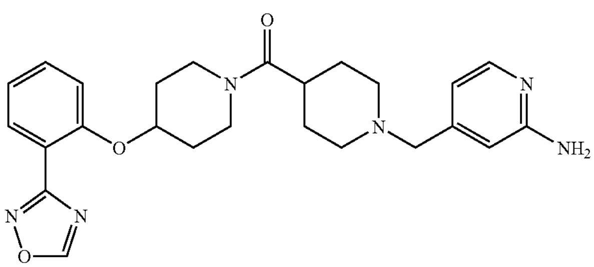 | 463 |
| 233 | 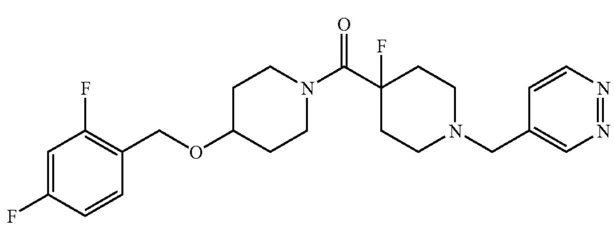 | 449 |
| 234 | 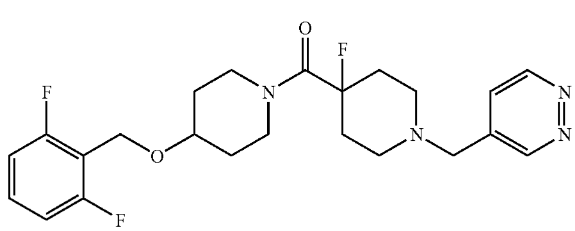 | 449 |

-continued

| Ex. No. | Structure | MS (M + H) |
|---|---|---|
| 235 | 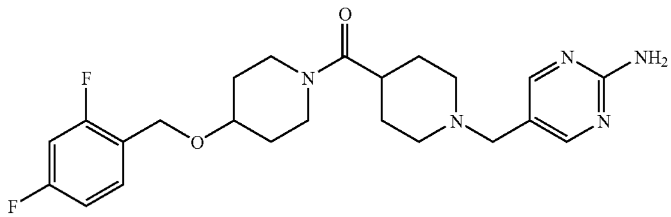 | 445 |
| 236 | 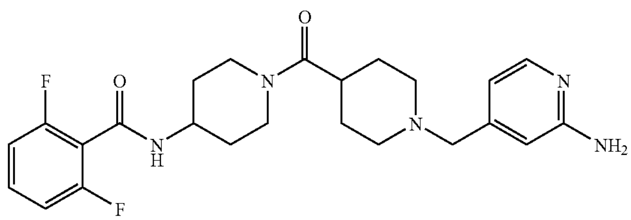 | 458 |
| 237 | 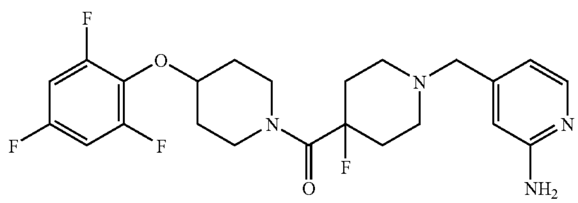 | 467 |
| 238 | 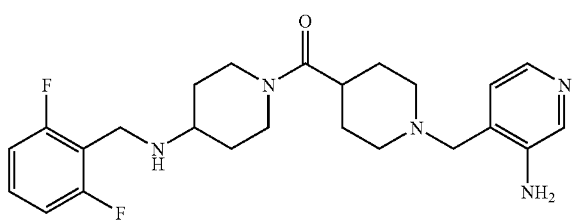 | 444 |
| 239 | 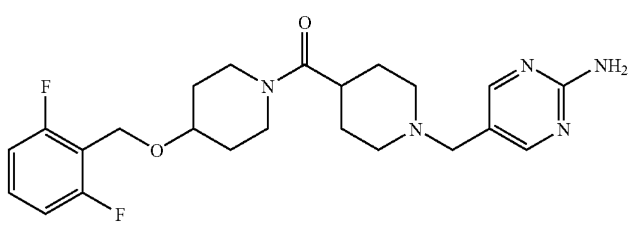 | 446 |
| 240 | 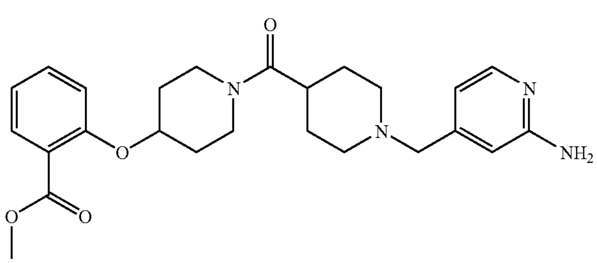 | 453 |

-continued
| Ex. No. | Structure | MS (M + H) |
|---|---|---|
| 241 | 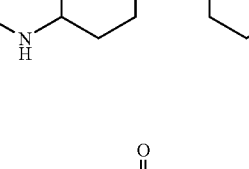 | 462 |
| 242 | 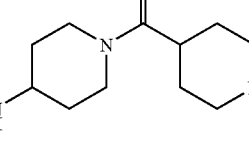 | 444 |
| 243 | 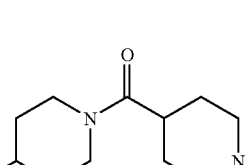 | 463 |
| 244 | 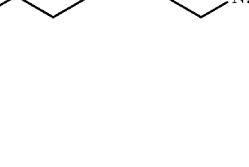 | 449 |
| 245 | 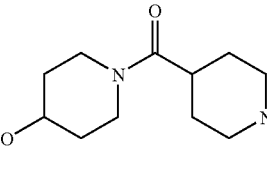 | 464 |
| 246 | 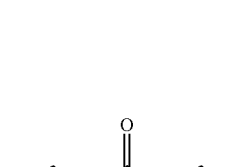 | 471 |

-continued

| Ex. No. | Structure | MS (M + H) |
|---|---|---|
| 247 | 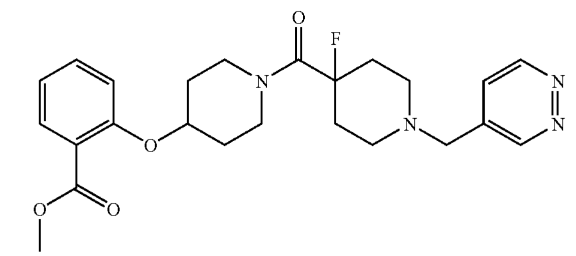 | 457 |
| 248 | 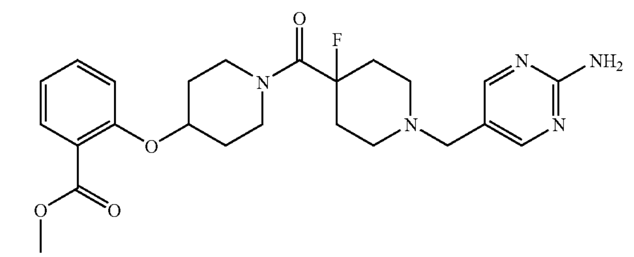 | 472 |
| 249 | 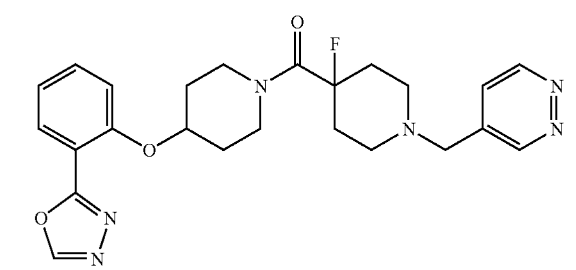 | 467 |
| 250 | 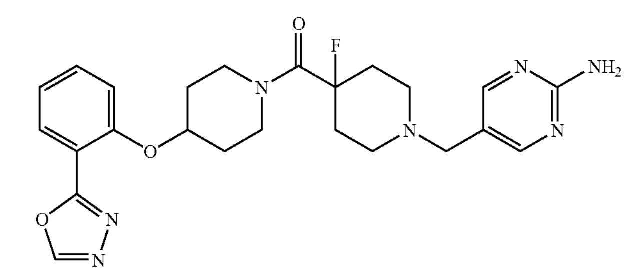 | 482 |
| 251 | 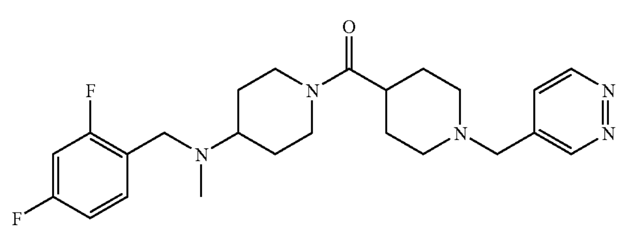 | 444 |
| 252 | 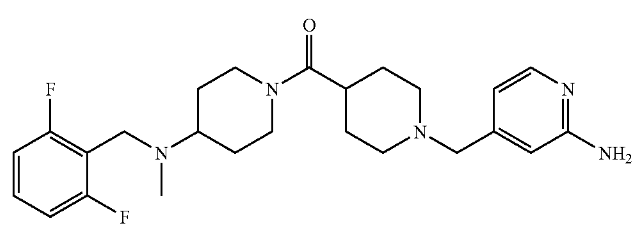 | 458 |

-continued

| Ex. No. | Structure | MS (M + H) |
|---|---|---|
| 253 | 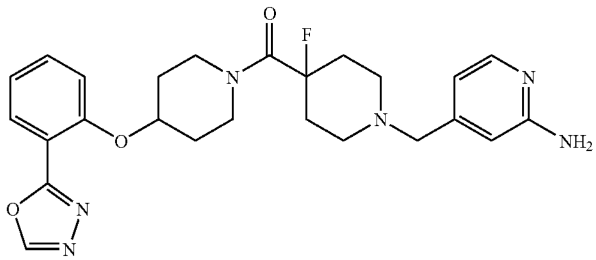 | 481 |
| 254 | 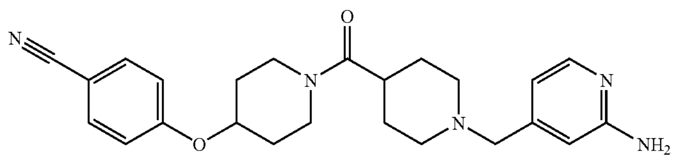 | 420 |
| 255 | 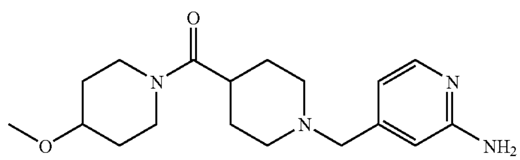 | 333 |
| 256 | 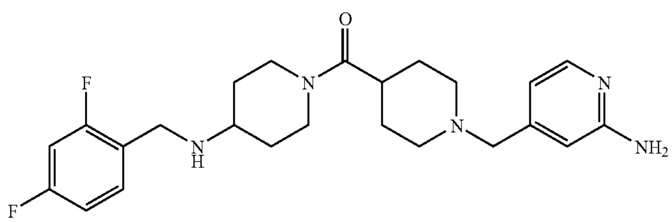 | 444 |
| 257 | 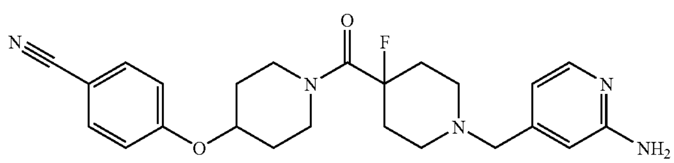 | 438 |
| 258 | 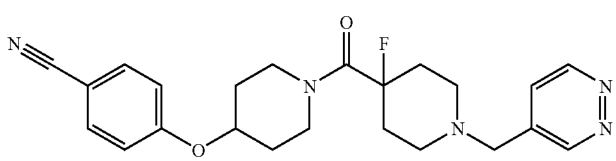 | 424 |
| 259 | 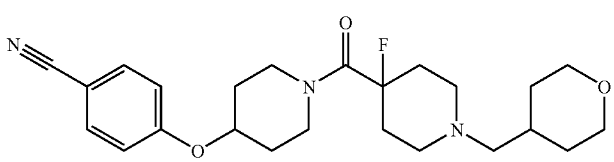 | 430 |
| 260 | 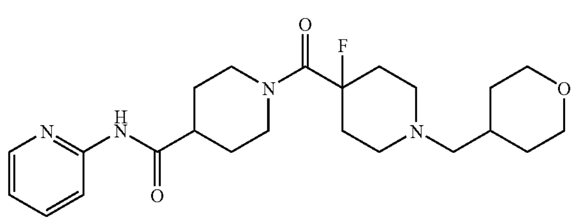 | 433 |

-continued
| Ex. No. | Structure | MS (M + H) |
|---|---|---|
| 261 | 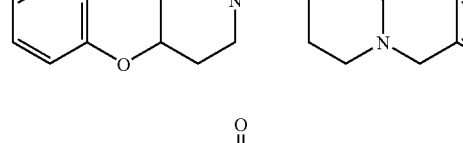 | 439 |
| 262 | 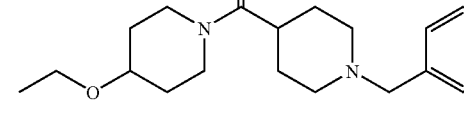 | 333 |
| 263 | 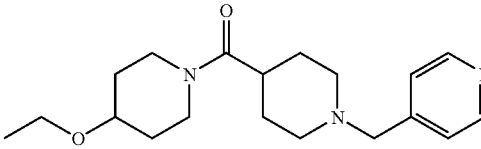 | 347 |
| 264 | 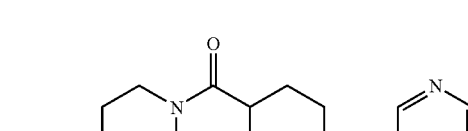 | 348 |
| 265 | 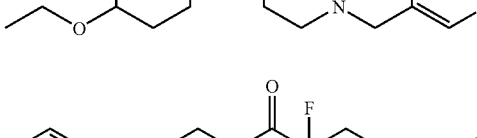 | 448 |
| 266 | 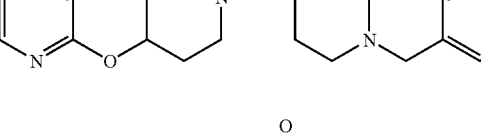 | 440 |
| 267 | 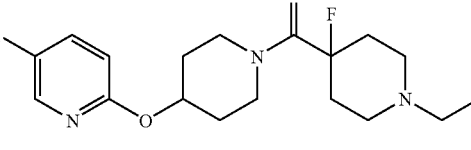 | 461 |
| 268 | 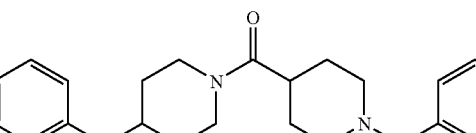 | 473 |

| Ex. No. | Structure | MS (M + H) |
|---|---|---|
| 269 | 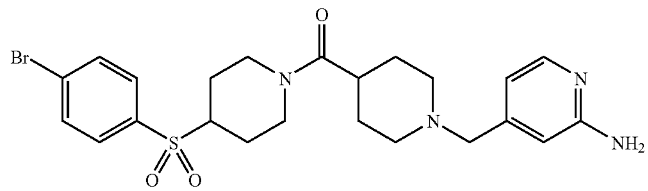 | 443 |
| 270 | 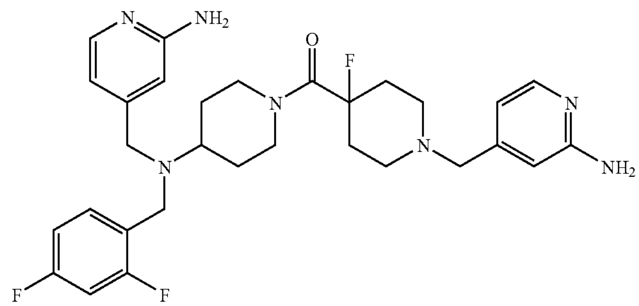 | 568 |
| 271 | 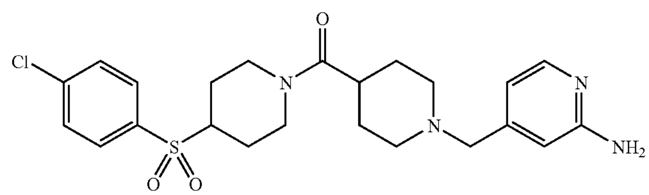 | 477 |
| 272 | 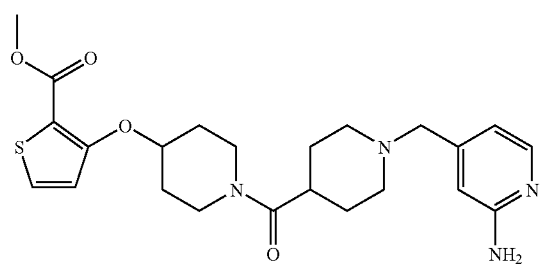 | 459 |
| 273 | 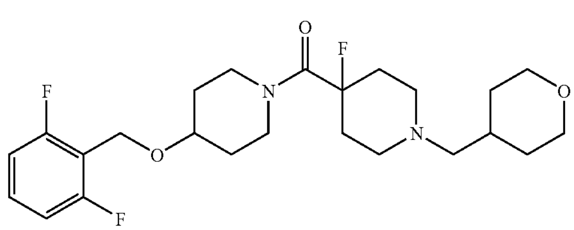 | 455 |
| 274 | 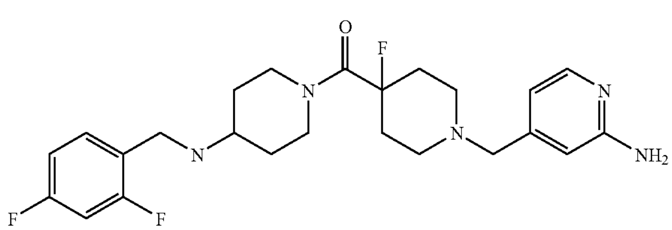 | 462 |

| Ex. No. | Structure | MS (M + H) |
|---|---|---|
| 275 | 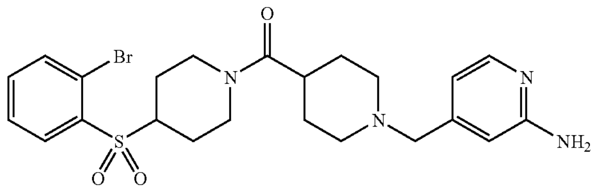 | 521 |
| 276 | 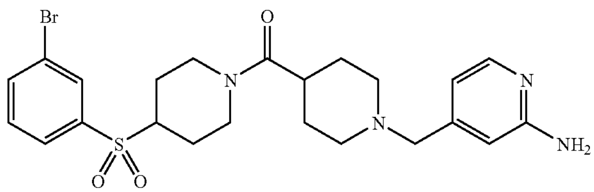 | 521 |
| 277 | 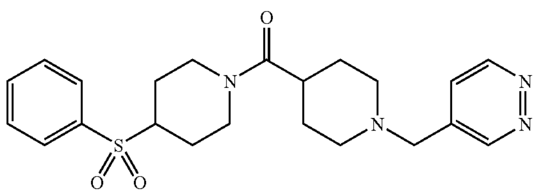 | 429 |
| 278 | 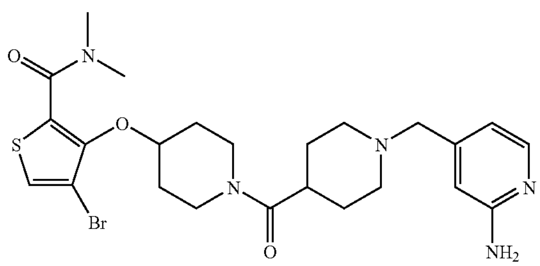 | 550 |
| 279 | 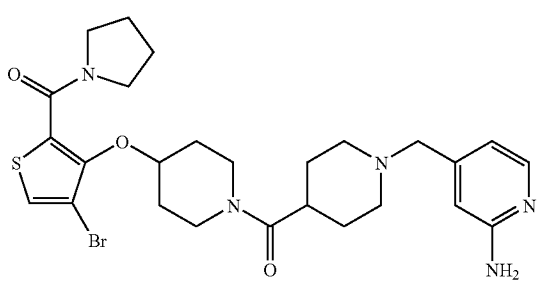 | 576 |
| 280 | 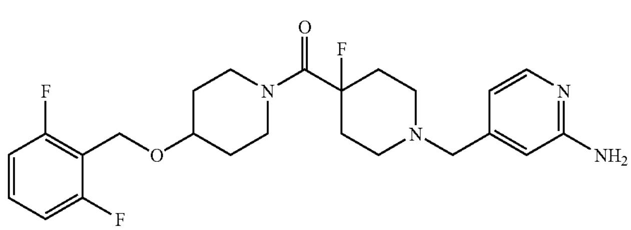 | 463 |

-continued

| Ex. No. | Structure | MS (M + H) |
|---|---|---|
| 281 | 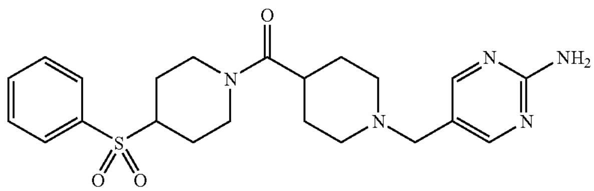 | 444 |
| 282 | 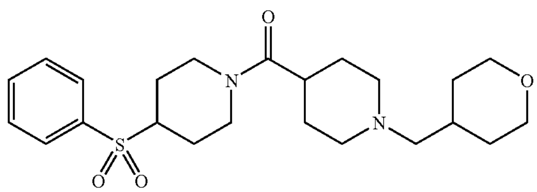 | 435 |
| 283 | 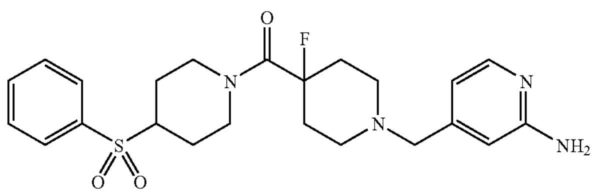 | 461 |
| 284 | 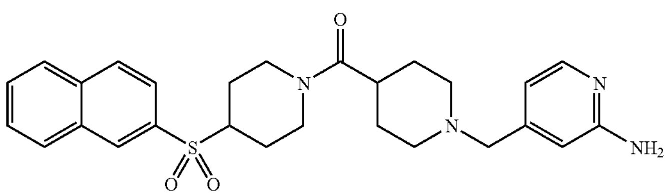 | 493 |
| 285 | 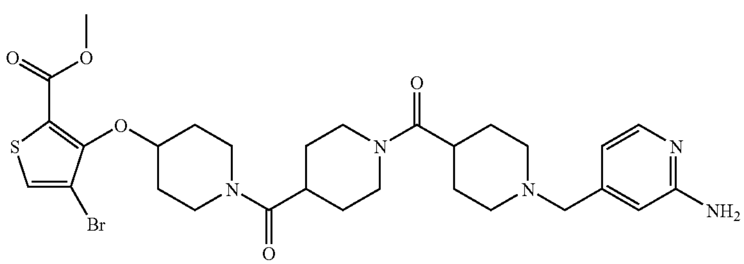 | 648 |
| 286 | 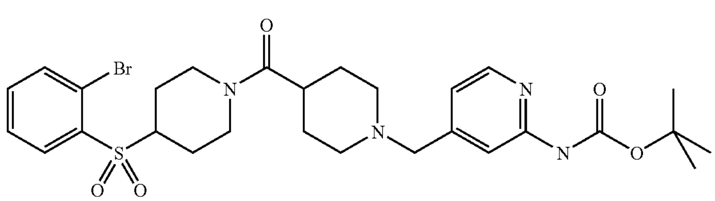 | 521 |
| 287 | 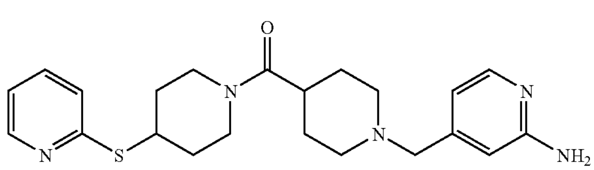 | 412 |

-continued
| Ex. No. | Structure | MS (M + H) |
|---|---|---|
| 288 | 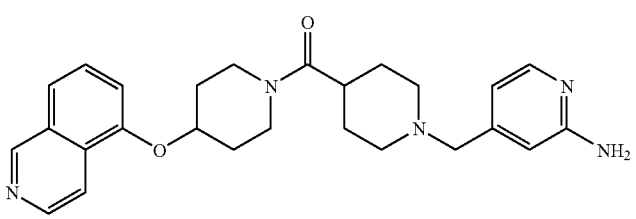 | 546 |
| 289 | 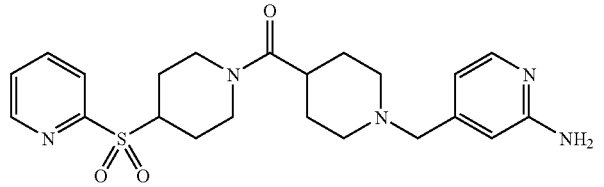 | 444 |
| 290 | 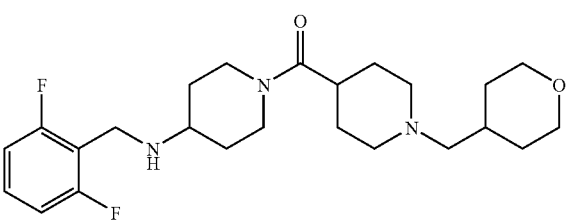 | 436 |
| 291 | 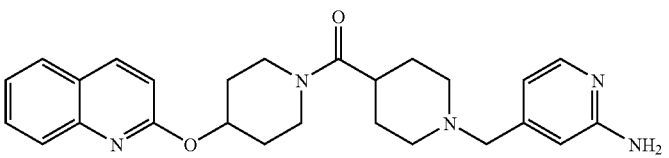 | 446 |
| 292 | 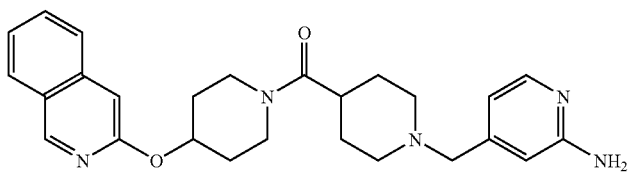 | 446 |
| 293 | 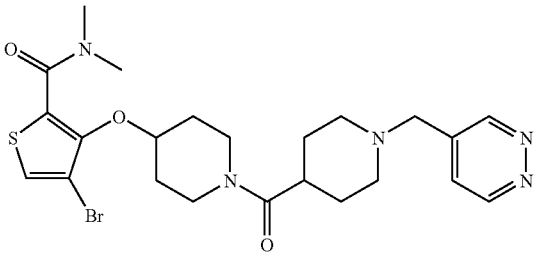 | 536 |
| 294 | 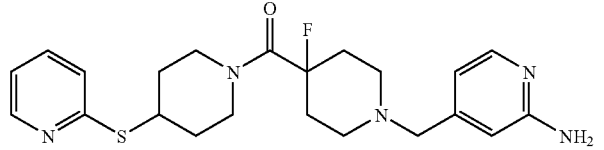 | 430 |

| Ex. No. | Structure | MS (M + H) |
|---|---|---|
| 295 | 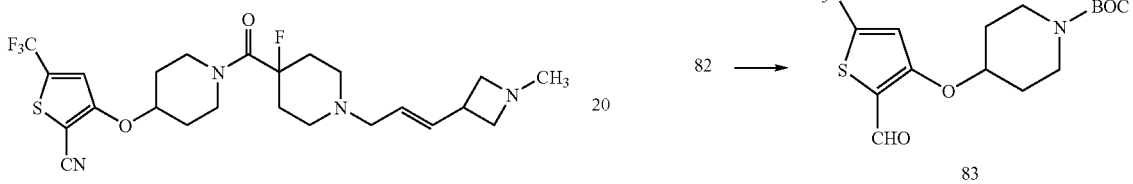 | 498 |

Example 296

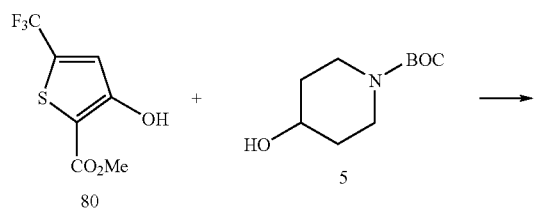

Step 1:

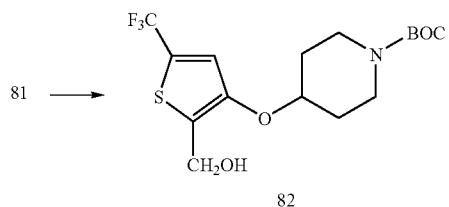

Compound 81 was prepared using the procedure for the preparation of compound 18 in step 2 of Example 13.

Step 2:

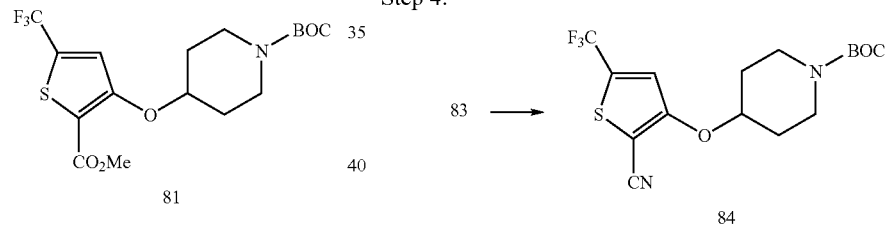

To a stirred solution of ether 81 (1.56 g, 3.81 mmol) in CH$_2$Cl$_2$ (35 ml) at −78° C. was added dropwise a 1.0 M solution of diisobutylaluminum hydride (11.5 ml, 11.5 mmol) in CH$_2$Cl$_2$. The reaction was continued over night and the temperature was increased to RT. A saturated aqueous NH$_4$Cl solution was added. The mixture was stirred for 30 min, filtered through a 1-in Celite pad, rinsing with CH$_2$Cl$_2$. The two layers of filtrate were separated. The aqueous layer was extracted with CH$_2$Cl$_2$ (2×). The combined organic layers were washed with brine, dried (Na$_2$SO$_4$), and concentrated in vacuo to give 1.65 g of alcohol 82 as a colorless oil.

Step 3:

82 →  (structure 83)

Crude 82 (1.65 g, 3.81 mmol) was dissolved in CH$_2$Cl$_2$ (40 ml) and 4-methyl-morpholine-N-oxide (1.12 g, 9.56 mmol), followed by a catalytic amount of tetra-propylammonium perruthenate (TPAP) was added. Reaction was continued at RT over night. The mixture was filtered through a 1-in silica gel pad, rinsing with EtOAc. The filtrate was concentrated in vacuo to give 1.07 g of 83 (74% over two steps) as a light yellow solid.

Step 4:

83 → (structure 84)

83 (1.07 g, 2.79 mmol) was dissolved in CH$_3$CN (30 ml). Hydroxyamine-O-sulfonic acid (0.95 g, 8.36 mmol) was added. The mixture was heated to reflux and heating continued for 4 days. After cooling to RT, the mixture was treated with 1.0M NaOH aqueous solution (50 ml), and extracted with CH$_2$Cl$_2$ (75 ml×2) and EtOAc (75 ml). The organic extracts were washed with brine, dried over Na$_2$SO$_4$, and concentrated in vacuo to give 0.95 g of 84 as a bright yellow solid.

Step 5:

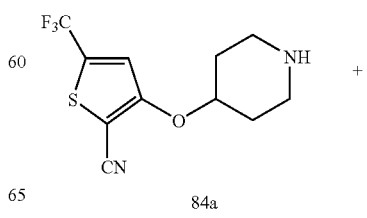

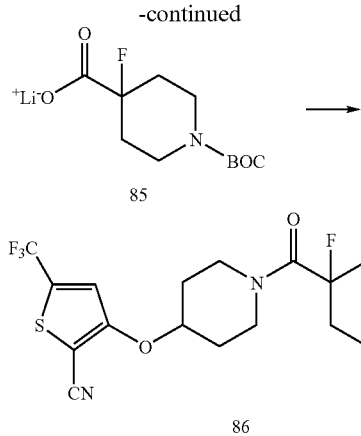

Compound 84a was prepared from 84 using procedure analogous to step 3 of example 13.

Preparation of compound 85 was previously described in WO 2002032893.

Compound 86 was prepared from 84a following the procedure for preparation of compound 17 in step 1 of Example 13.

Step 6:

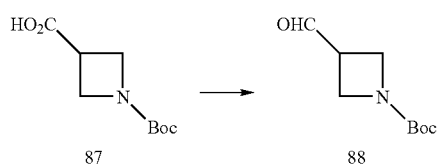

To a stirred solution of 87 (5.00 g, 24.8 mmol) in THF (200 ml) at ~20° C. was added dropwise a 1.0 M solution of borane-THF complex in THF (50 ml, 50 mmol). The cooling bath was removed after 2 h. Reaction was continued overnight. The mixture was poured carefully into an ice-cooled saturated $NH_4Cl$ aqueous solution (400 ml). The aqueous mixture was extracted with $CH_2Cl_2$ (150 ml×4). The combined organic extracts were washed with brine, dried by $Na_2SO_4$, and concentrated in vacuo to give 4.87 g of N-Boc-3-hydroxymethyl-1-azetidine.

The N-Boc-3-hydroxymethyl-1-azetidine was dissolved in $CH_2Cl_2$ (150 ml) and Dess-Martin periodinane (14.2 g, 33.48 mmol) was added. The mixture was stirred at RT for 1 day. Ether (300 ml) was added and the mixture was washed with a 1.0 M NaOH aqueous solution (100 ml×3) and brine (100 ml). The aqueous washings were combined and re-extracted with ether (100 ml×2). The combined organic extracts were dried with $MgSO_4$ and filtered through a Celite pad. The filtrate was concentrated in vacuo to give 3.51 g (76% over two steps) of 88 as a light yellow oil.

Step 7:

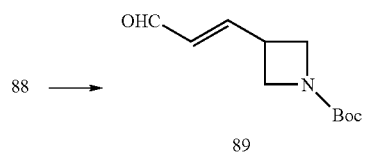

88 (3.51 g, 18.91 mmol) was dissolved in THF (100 ml). Triphenylphos-phoranylidene aldehyde (11.51 g, 37.82 mmol) was added. The mixture was stirred for 2 days, then filtered through a Celite pad, rinsing with $CH_2Cl_2$. The filtrate was concentrated in vacuo to a dark yellow oil, purified by flash column chromatography, eluting with $CH_2Cl_2$-MeOH (400:1, 200:1, 135:1, v/v). Removal of solvents afforded 1.86 g (47%) of 89 as a yellow oil.

Step 8:

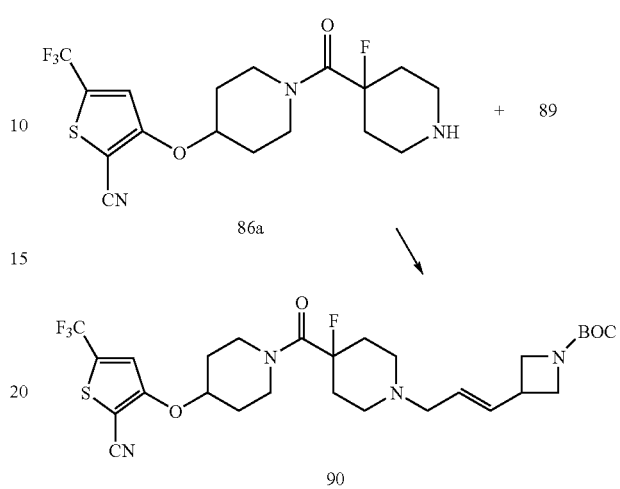

Compound 86a was prepared from 86 using the procedure described for the conversion of compound 18 into 19 in step 3 of Example 13. Compound 86a was converted into 90 using the procedure described for the conversion of compound 19 into 20 in step 4 of Example 13.

Step 9:

90 (58 mg, 0.097 mmol) was dissolved in $CH_2Cl_2$ (2 ml) and cooled in a −20° C. bath. Iodotrimethylsilane (35 μl, 0.25 mmol) was added dropwise. The reaction was continued for 4 h and the temperature was increased to 0° C. A 1.0 M NaOH aqueous solution (20 ml) was added. The mixture was extracted with $CH_2Cl_2$ (30 ml×3). The organic extracts were washed with brine, dried by $Na_2SO_4$, and concentrated in vacuo to give 57 mg of the crude deprotected intermediate as a light yellow solid. This intermediate was dissolved in $CH_2Cl_2$ (2 ml) and treated with formalin (0.1 ml, 1.34 mmol) and $NaBH(OAc)_3$ (60 mg, 0.28 mmol). Two drops of AcOH were added. The reaction was continued overnight, and quenched with a saturated $NaHCO_3$ aqueous solution (30 ml). The aqueous mixture was extracted with $CH_2Cl_2$ (30 ml×3). The extracts were washed with brine, dried over $Na_2SO_4$, and concentrated in vacuo to a yellow oil, purified by preparative TLC($CH_2Cl_2$-7N $NH_3$ in MeOH=20:1, v/v) to afford 13 mg (26.5%) of the title compound as a near colorless solid ($MH^+$=515.3).

Example 297

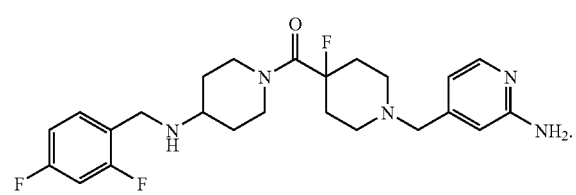

Step 1:

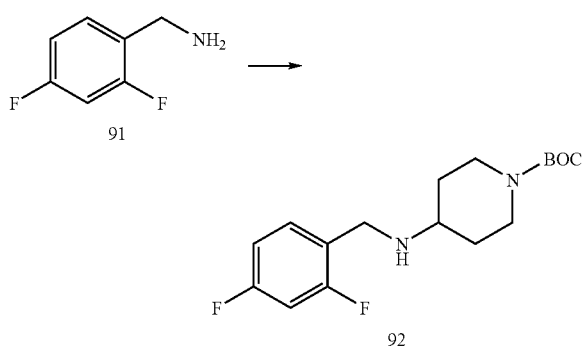

Compound 92 was prepared following the procedure described for compound 37 in step 1 of Example 20.

Compound 92 was converted into title compound as described for Example 23, except that N-Boc-2-aminopyridine-4-carbaldehyde was used in place of pyridazine-4-carbaldehyde.

Example 298

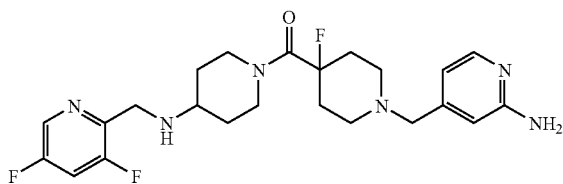

Step 1

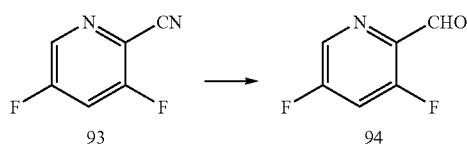

To a −78° C. solution of 2-cyano-3,5-difluoropyridine 93 (1.75 g; 12.5 mmol) in 20 mL of THF was added 20.6 mL of 20% wt toluene DIBAL solution (25.0 mmol). Reaction mixture was stirred for 3 h at −78° C., followed by overnight stirring at room temperature. The mixture was quenched with EtOAc, followed by aqueous NH$_4$Cl, followed by aqueous sodium potassium tartrate solution. The mixture was stirred for 2 h at room temperature, and partitioned between water and EtOAc. Organic phase was separated, dried and concentrated, and the residue was flash chromatographed (CH$_2$Cl$_2$) to produce 340 mg of aldehyde 94 as a white solid.

Step 2

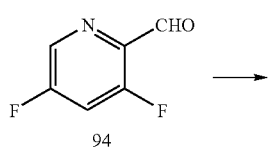

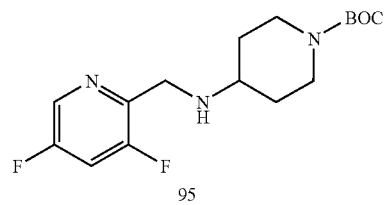

A mixture of aldehyde 94 (340 mg; 2.38 mmol), 4-amino-N-Boc-piperidine (400 mg; 2.00 mmol) and NaBH(OAc)$_3$ (848 mg; 4.00 mmol) was stirred overnight at room temperature. The mixture was subjected to aqueous NaHCO$_3$ work-up —CH$_2$Cl$_2$ extraction. Organic phase was separated, dried and concentrated to produce 620 mg of amine 95.

Step 3

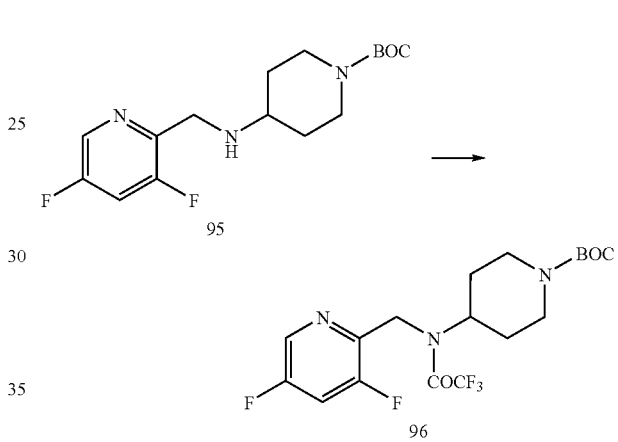

To a solution of amine 95 (620 mg; 1.90 mmol) in 25 mL of CH$_2$Cl$_2$ was added TFAA (0.54 mL; 3.82 mmol) and triethylamine (0.8 mL; 5.72 mmol). Reaction mixture was stirred overnight, diluted with water, basified with 1 N NaOH and extracted with CH$_2$Cl$_2$. Flash chromatography produced 600 mg of 96 as a clear oil.

Step 4

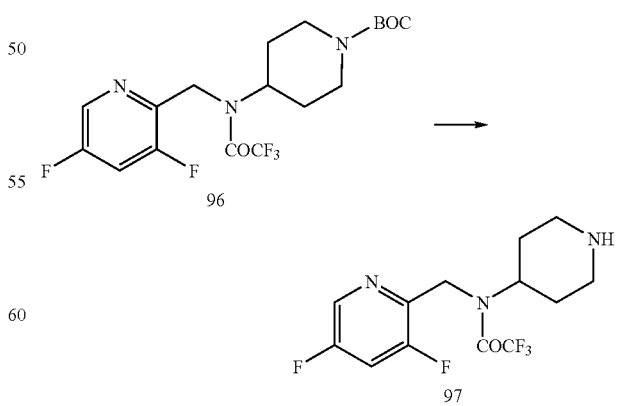

Boc-protected amine 96 was stirred in 20% TFA/CH$_2$Cl$_2$ overnight at room temperature. TFA was removed under vacuum, and the residue was subjected to aqueous NaHCO₃ work-up —CH₂Cl₂ extraction to produce 426 mg of amine 97 as a white solid.

Step 5

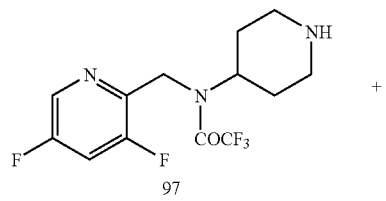

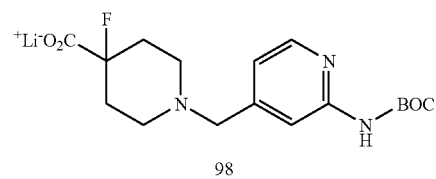

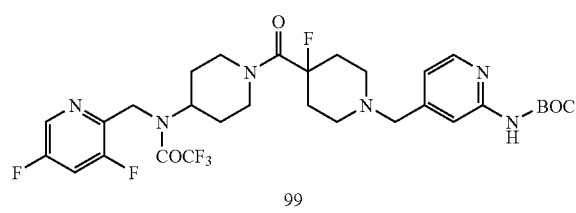

Compound 98 was prepared as described in WO 2002032893, steps 14 of Example 3.

A mixture of amine 97 (227 mg; 0.70 mmol), acid lithium salt 98 (303 mg; 0.84 mmol), EDC (201 mg; 1.05 mmol), HOBT (142 mg; 1.05 mmol) and triethylamine (0.24 mL; 1.75 mmol) in 6 mL of DMF was stirred overnight at 65° C. DMF was removed under vacuum, the residue was partitioned between 1 N aqueous NaOH and CH₂Cl₂. Organic phase was separated, dried and concentrated, and the residue was flash chromatographed (1-2% 2.3M NH₃ in MeOH/CH₂Cl₂) to produce 210 mg of 99 as a clear oil.

Step 6

Boc-protected amine 99 was stirred in 20% TFA/CH₂Cl₂ overnight at room temperature. TFA was removed under vacuum, and the residue was subjected to aqueous NaHCO₃ work-up —CH₂Cl₂ extraction. Organic phase was concentrated, and the residue was treated with 7M NH₃ in MeOH overnight at 90° C. Flash chromatography (1-2% 2.3M NH₃ in MeOH/CH₂Cl₂) produced 110 mg of the title compound Example 298. MH⁺=463

Example 299

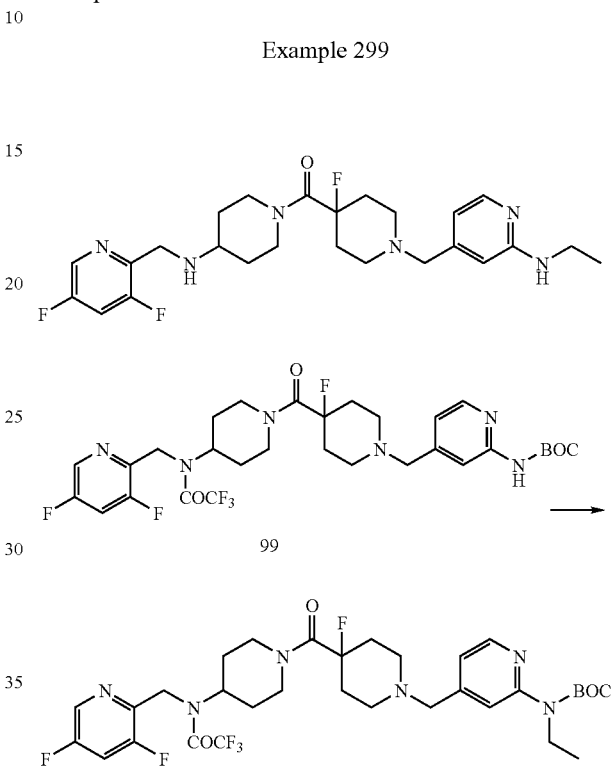

To a solution of amine 99 (186 mg; 0.28 mmol) in 5 mL of THF was added 0.025 mL (0.31 mmol) of ethyl iodide and 17 mg (0.70 mmol) of NaH. Gas evolution was observed. Reaction mixture was stirred at 70° C. overnight, diluted with water, neutralized with aqueous NH₄Cl and extracted with CH₂Cl₂. Organic phase was dried and concentrated to produce 180 mg of 100 as a clear oil.

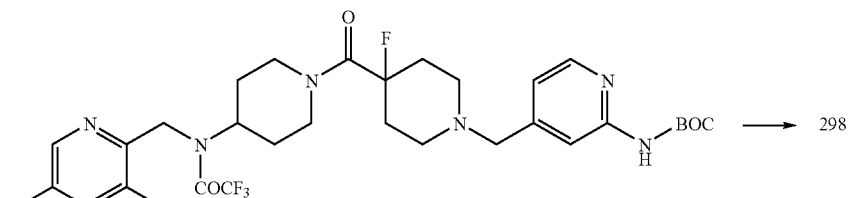

Compound 100 was converted into the title compound Example 299 using the same procedures as in step 6 of Example 298. MH+=491

Example 300

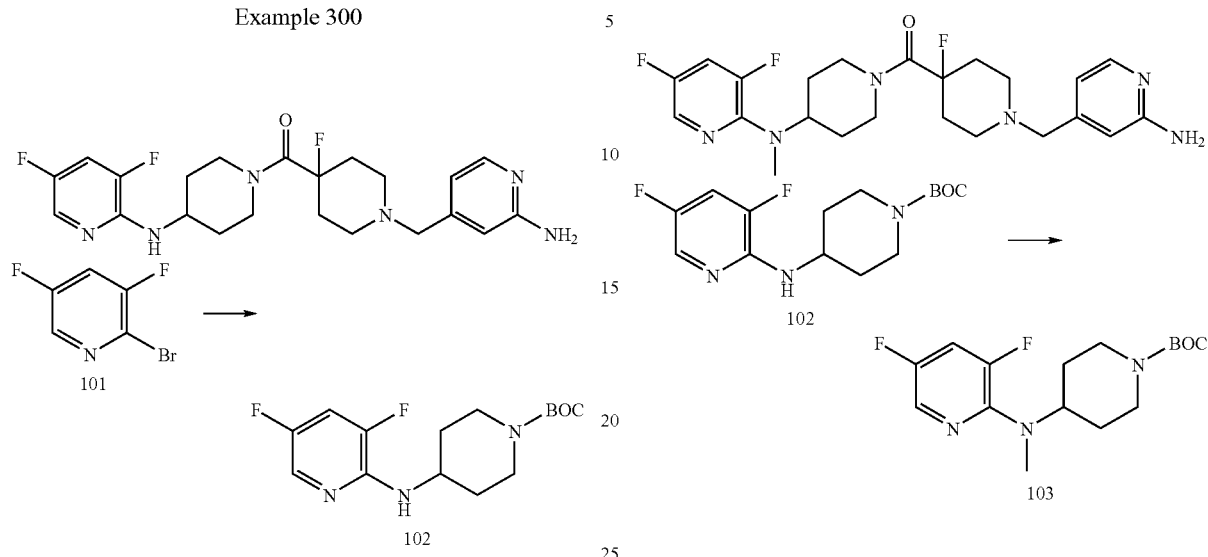

To a solution of bromopyridine 101 (2.00 g; 10.3 mmol) in 30 mL of toluene was added Pd$_2$(dba)$_3$ (0.94 g; 1.0 mmol), PBu$^t_3$ (0.33 g; 1.65 mmol) sodium tert-butoxide (1.48 g; 15.5 mmol), followed by 4-amino-N-Boc-piperidine (3.10 g; 15.5 mmol). Reaction mixture was stirred for 48 h at room temperature, diluted with CH$_2$Cl$_2$ and filtered through Celite. The filtrate was subjected to aqueous work-up —CH$_2$Cl$_2$ extraction. Organic phase was separated, dried and concentrated, and the residue was flash chromatographed (0-0.5% MeOH/CH$_2$Cl$_2$) to produce 2.21 g of 102 as a yellow solid.

Compound 102 was converted into the title compound Example 300 using the same procedures as described for steps 4-6 in Example 298. MH+=449.

Example 301

To a solution of amine 102 (150 mg; 0.48 mmol) in 4 mL of DMF was added NaH (29 mg; 1.2 mmol) and methyl iodide (45 µL; 0.72 mmol). Reaction mixture was stirred at room temperature overnight. DMF was removed under vacuum. The residue was partitioned between CH$_2$Cl$_2$ and water. Organic phase was separated, dried and concentrated to produce 160 mg of crude 103 as brown oil, which was used directly.

Compound 103 was converted into the title compound Example 301 using the same procedures as described for steps 4-6 in Example 298. MH+=463

Using the various procedures described above the following compounds were prepared:

| Ex. | Structure | (M + H)+ |
|---|---|---|
| 302 | 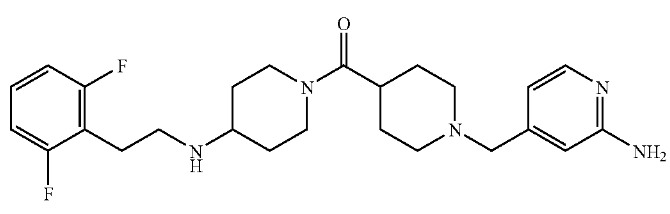 | 458 |
| 303 | 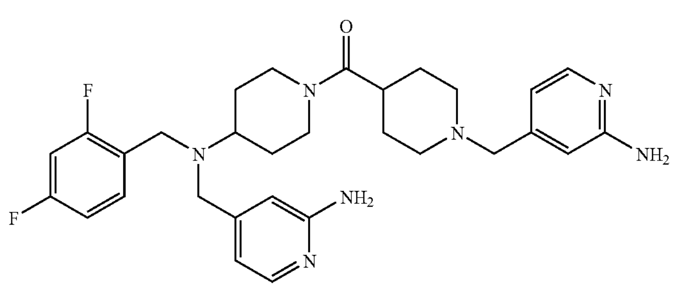 | 564 |

-continued

| Ex. | Structure | (M + H)+ |
|---|---|---|
| 304 | 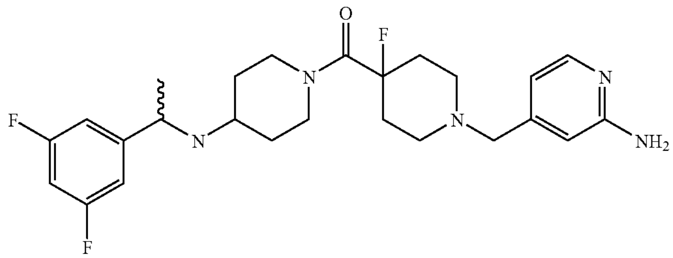 | 476 |
| 305 | 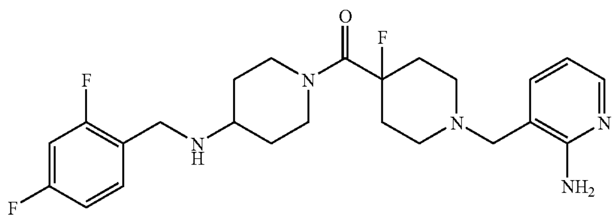 | 462 |
| 306 | 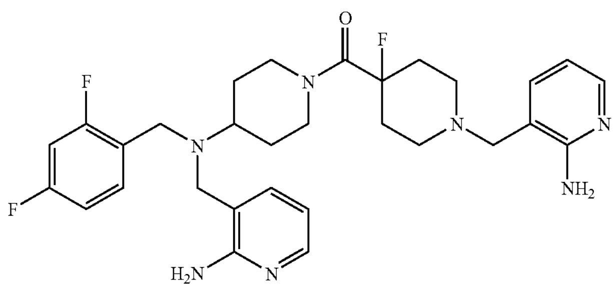 | 568 |
| 307 | 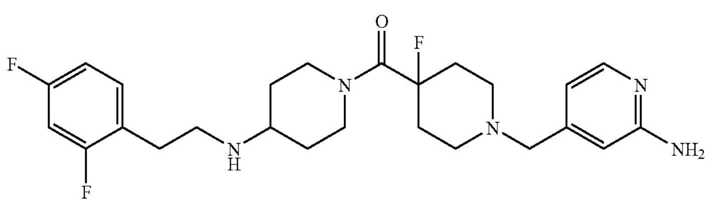 | 476 |
| 308 | 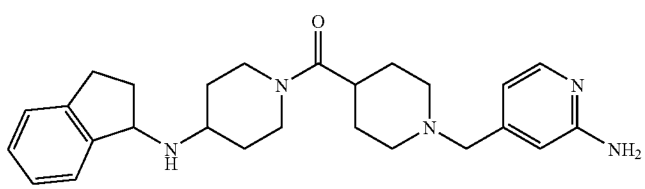 | 434 |
| 309 | 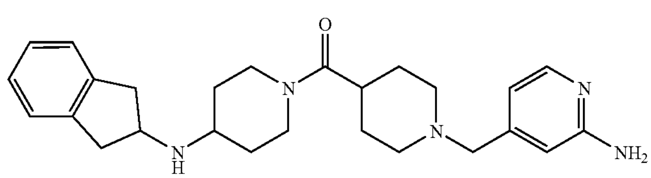 | 434 |
| 310 | 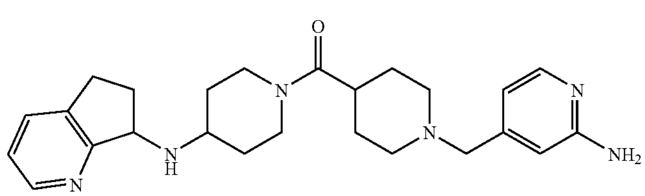 | 435 |

| Ex. | Structure | (M + H)+ |
|---|---|---|
| 311 | 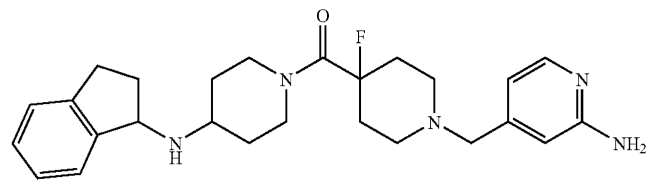 | 452 |
| 312 | 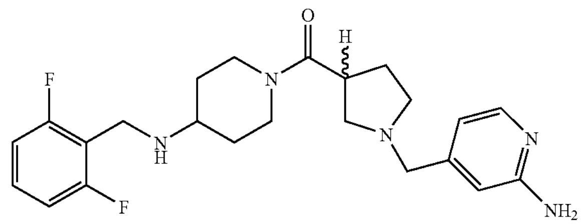 | 430 |

General Procedure for $H_3$-Receptor Binding Assay

The source of the $H_3$ receptors in this experiment was guinea pig brain. Alternatively, the source of $H_3$ receptors was recombinant human receptor, expressed in HEK-293 (human embryonic kidney) cells.

The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein, 5 μg in the case of recombinant human receptor) to the reaction tubes. The reaction was started by the addition of 3 nM [$^3$H]R-α-methyl histamine (8.8 Ci/mmol) or 3 nM [$^3$H]Na$^\alpha$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds of formula I have a $K_i$ within the range of about 1 to about 10000 nM. Preferred compounds of formula I have a $K_i$ within the range of about 0.2 to about 100 nM. More preferred compounds of formula I have a $K_i$ within the range of about 0.2 to about 20 nM. The compound of Example 11 has a $K_i$ of 0.2 nM in the guinea pig receptor assay, while the compound of Example 256 has a $K_i$ of 0.7 nM in the recombinant human receptor assay.

In this specification, the term "at least one compound of formula I" means that one to three different compounds of formula I may be used in a pharmaceutical composition or method of treatment. Preferably one compound of formula I is used. Similarly, "at least one $H_1$ receptor antagonist" or "at least one other compound (or agent) for treating obesity, metabolic syndrome or cognition deficit disorders" means that one to three different $H_1$ antagonists or other compounds may be used in a pharmaceutical composition or method of treatment. Preferably, one $H_1$ antagonist or one other compound for treating obesity, metabolic syndrome or cognition deficit disorders is used in the combinations.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of $H_3$ antagonist and $H_1$ antagonist compounds, the two active components may be co-administered simultaneously or sequentially, or a single pharmaceutical composition comprising a $H_3$ antagonist and an $H_1$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the $H_1$ antagonist can be determined from published material, and may range from 1 to 1000 mg per dose. When used in combination, the dosage levels of the individual components are preferably lower than the recommended individual dosages because of the advantageous effect of the combination.

When separate $H_3$ and $H_1$ antagonist pharmaceutical compositions are to be administered, they can be provided in a kit comprising in a single package, one container comprising an $H_3$ antagonist in a pharmaceutically acceptable carrier, and a separate container comprising an $H_1$ antagonist in a pharmaceutically acceptable carrier, with the $H_3$ and $H_1$ antagonists being present in amounts such that the combination is therapeutically effective. A kit is advantageous for administering a combination when, for example, the components must be administered at different time intervals or when they are in different dosage forms.

Similarly, when the invention comprises a combination of $H_3$ antagonist and at least one other compound for treating obesity, metabolic syndrome, cognition deficit disorders, NAFLD, hepatic steatosis, NASH, cirrhosis, or hepatacellular carcinoma the two active components may be co-administered simultaneously or sequentially, or a single pharmaceutical composition comprising a $H_3$ antagonist and another compound in a pharmaceutically acceptable carrier can be administered. The components of the combination can be administered individually or together in any conventional dosage form such as capsule, tablet, powder, cachet, suspension, solution, suppository, nasal spray, etc. The dosage of the other compound for treating obesity, metabolic syndrome or cognition deficit disorders can be determined from published material, and may range from 1 to 1000 mg per dose.

When separate pharmaceutical compositions comprising an $H_3$ antagonist and at least one other compound for treating obesity, metabolic syndrome or cognition deficit disorders are to be administered, they can be provided in a kit comprising in a single package, one container comprising an $H_3$ antagonist in a pharmaceutically acceptable carrier, and a separate container or containers comprising at least one other compound for treating obesity, metabolic syndrome, cognition deficit disorders NAFLD, hepatic steatosis, NASH, cirrhosis, or hepatacellular carcinoma in a pharmaceutically acceptable carrier, with the $H_3$ antagonists and other compounds being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for treating cognition deficit disorder in a patient suffering from Alzheimer's disease or schizophrenia comprising administering to the patient in need of such treatment an effective amount of a compound which is selected from the group consisting of:

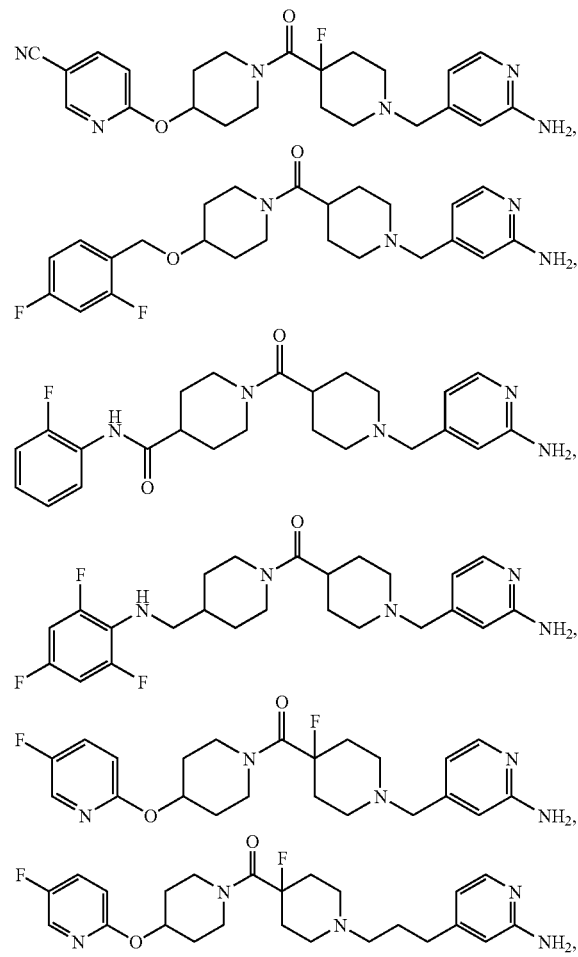

-continued
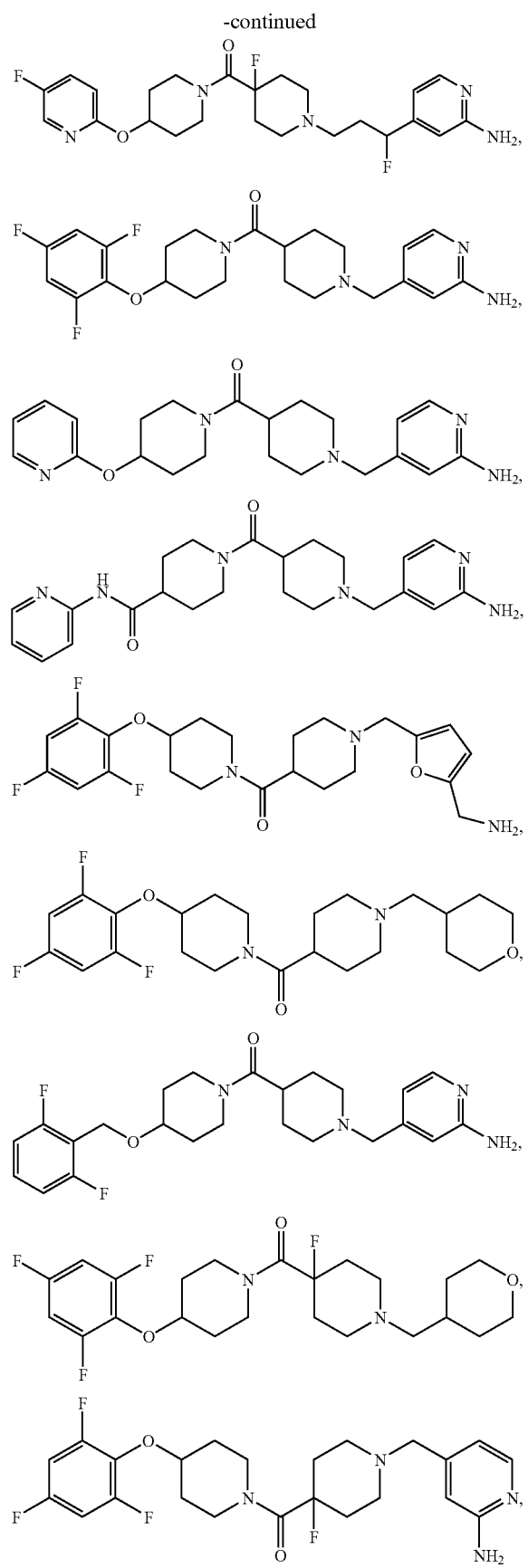
-continued
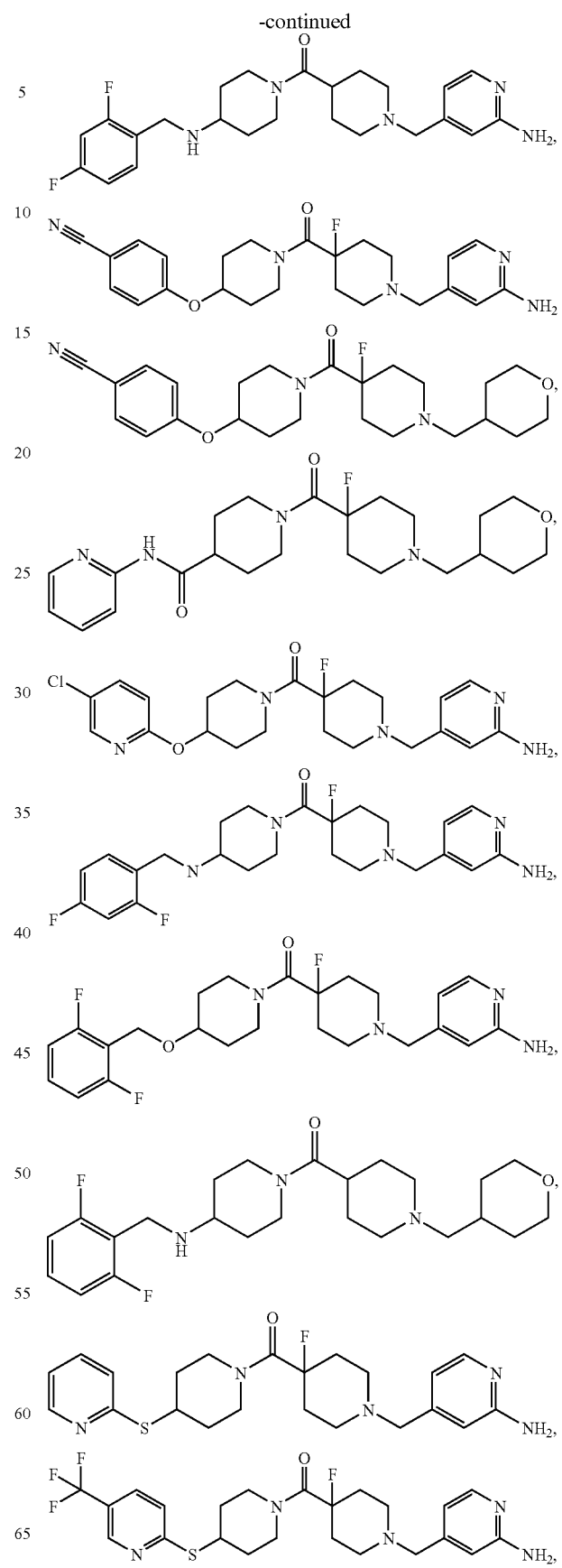

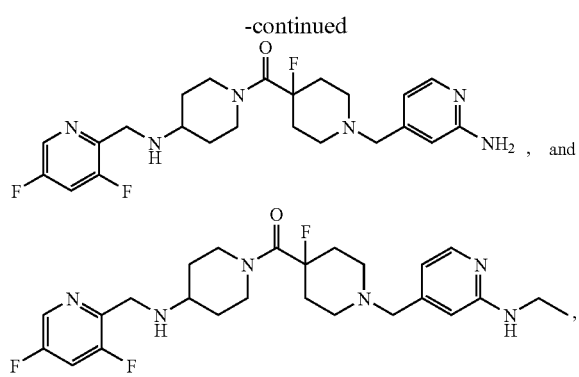
or a pharmaceutically acceptable salt thereof.
2. A method for treating cognition deficit disorder in a patient suffering from Alzheimer's disease or schizophrenia comprising administering to the patient in need of such treatment an effective amount of a compound which is:
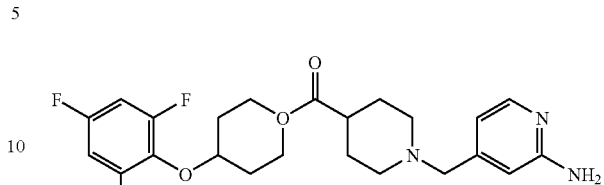
or a pharmaceutically acceptable salt thereof.
* * * * *